United States Patent
Iadonato et al.

(10) Patent No.: US 9,937,230 B2
(45) Date of Patent: Apr. 10, 2018

(54) OPHTHALMIC USES OF TOXIN-BASED THERAPEUTIC PEPTIDES AND PHARMACEUTICAL COMPOSITIONS THEREOF

(71) Applicant: Kineta One, LLC, Seattle, WA (US)

(72) Inventors: Shawn P. Iadonato, Seattle, WA (US); Ernesto J. Munoz, Seattle, WA (US)

(73) Assignee: Kineta One, LLC, Seattle, WA (US)

( * ) Notice: Subject to any disclaimer, the term of this patent is extended or adjusted under 35 U.S.C. 154(b) by 0 days.

(21) Appl. No.: 14/907,102

(22) PCT Filed: Jul. 22, 2014

(86) PCT No.: PCT/US2014/047691
§ 371 (c)(1),
(2) Date: Jan. 22, 2016

(87) PCT Pub. No.: WO2015/013330
PCT Pub. Date: Jan. 29, 2015

(65) Prior Publication Data
US 2016/0151457 A1    Jun. 2, 2016

Related U.S. Application Data

(60) Provisional application No. 61/857,157, filed on Jul. 22, 2013.

(51) Int. Cl.
| | | |
|---|---|---|
| *A61K 38/00* | (2006.01) | |
| *A61P 9/10* | (2006.01) | |
| *A61P 27/02* | (2006.01) | |
| *A61K 38/17* | (2006.01) | |
| *G01N 33/68* | (2006.01) | |
| *A61K 9/00* | (2006.01) | |
| *A61K 47/02* | (2006.01) | |
| *A61K 47/22* | (2006.01) | |

(52) U.S. Cl.
CPC ........ *A61K 38/1767* (2013.01); *A61K 9/0019* (2013.01); *A61K 9/0048* (2013.01); *A61K 47/02* (2013.01); *A61K 47/22* (2013.01); *G01N 33/6872* (2013.01); *G01N 2333/52* (2013.01); *G01N 2800/52* (2013.01)

(58) Field of Classification Search
CPC .... A61K 38/1767; A61K 47/02; A61K 47/22; A61K 9/0019; A61K 9/0048; G01N 2333/52; G01N 2800/52; G01N 33/6872
See application file for complete search history.

(56) References Cited

U.S. PATENT DOCUMENTS

| | | | |
|---|---|---|---|
| 8,080,523 B2 * | 12/2011 | Beeton | A61K 47/48261 514/17.4 |
| 9,381,261 B2 * | 7/2016 | Iadonato | A61K 38/1767 |
| 2008/0221024 A1 * | 9/2008 | Chandy | A61K 47/48261 514/4.8 |

FOREIGN PATENT DOCUMENTS

| | | | | |
|---|---|---|---|---|
| WO | 98/236739 A2 | 6/1998 | | |
| WO | WO2012/170392 | * | 6/2012 | ............. A61K 38/16 |

OTHER PUBLICATIONS

Chu et al. Sympathetic ophthalmia: to the twenty-first century and beyond. J Ophthalmic Inflammation and Infection, 2013, vol. 3, No. 49, pp. 1-9.*
Castaneda, O., et al., "Characterization of a Potassium Channel Toxin from the Caribbean Sea Anemone *Stichodactyla helianthus*," Toxicon 33(5):603-613, May 1995.
International Search Report and Written Opinion dated Jan. 30, 2015, issued in corresponding International Application No. PCT/US2014/047691, filed Jul. 22, 2014, 11 pages.

* cited by examiner

*Primary Examiner* — Marcela M Cordero Garcia
(74) *Attorney, Agent, or Firm* — Christensen O'Connor Johnson Kindness PLLC

(57) ABSTRACT

Disclosed herein are methods of treating ophthalmic conditions such as dry eye and uveitis by administering a pharmaceutical composition including a toxin-based therapeutic peptide. The peptide can include an acid or amide at the C-terminus and can be attached to an organic or inorganic chemical entity that has an anionic charge.

12 Claims, 7 Drawing Sheets

SEQUENCE LISTING

```
<160> NUMBER OF SEQ ID NOS: 256

<210> SEQ ID NO 1
<211> LENGTH: 35
<212> TYPE: PRT
<213> ORGANISM: Stichodactyla helianthus

<400> SEQUENCE: 1

Arg Ser Cys Ile Asp Thr Ile Pro Lys Ser Arg Cys Thr Ala Phe Gln
 1               5                  10                  15

Cys Lys His Ser Met Lys Tyr Arg Leu Ser Phe Cys Arg Lys Thr Cys
            20                  25                  30

Gly Thr Cys
        35

<210> SEQ ID NO 2
<211> LENGTH: 35
<212> TYPE: PRT
<213> ORGANISM: Artificial Sequence
<220> FEATURE:
```

<223> OTHER INFORMATION: ShK-Based Peptide

<400> SEQUENCE: 2

Arg Ser Cys Ile Asp Thr Ile Pro Lys Ser Arg Cys Thr Ala Phe Gln
1               5                   10                  15

Ser Lys His Ser Met Lys Tyr Arg Leu Ser Phe Cys Lys Thr Ser
            20                  25                  30

Gly Thr Cys
        35

<210> SEQ ID NO 3
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 3

Arg Ser Ser Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Ser
        35

<210> SEQ ID NO 4
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 4

Ser Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 5
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MISC_FEATURE
<222> LOCATION: (1)..(1)
<223> OTHER INFORMATION: N-acetylarginine

<400> SEQUENCE: 5

Xaa Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 6
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 6

Ser Cys Ile Asp Thr Ile Pro Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 7
<211> LENGTH: 33
<212> TYPE: PRT
<213> ORGANISM: Artificial Sequence
<220> FEATURE:
<223> OTHER INFORMATION: ShK-Based Peptide

<400> SEQUENCE: 7

Cys Ile Asp Thr Ile Pro Lys Ser Arg Cys Thr Ala Phe Gln Cys Lys
1               5                   10                  15

His Ser Met Lys Tyr Arg Leu Ser Phe Cys Arg Lys Thr Cys Gly Thr
            20                  25                  30

Cys

<210> SEQ ID NO 8
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 8

Ala Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 9
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 9

Gln Cys Ile Asp Thr Ile Pro Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 10
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 10

Ala Cys Ile Asp Thr Ile Pro Lys Ser Arg Cys Thr Ala Phe Gln Cys

```
1               5                   10                  15
Lys His Ser Met Lys Tyr Arg Leu Ser Phe Cys Arg Lys Thr Cys Gly
            20                  25                  30

Thr Cys

<210> SEQ ID NO 11
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 11

Thr Cys Ile Asp Thr Ile Pro Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 12
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 12

Arg Gln Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 13
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 13

Arg Ala Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 14
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 14

Arg Thr Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30
```

```
<210> SEQ ID NO 15
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 15

Ala Gln Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 16
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 16

Ala Ala Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 17
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 17

Ala Thr Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 18
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 18

Arg Ser Cys Ala Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

```
<210> SEQ ID NO 19
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 19

Arg Ser Cys Ala Asp Thr Ile Pro Lys Ser Arg Cys Thr Ala Ala Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 20
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 20

Arg Ser Cys Ala Asp Thr Ile Pro Lys Ser Arg Cys Thr Ala Ala Gln
1               5                   10                  15

Cys Lys His Ser Met Lys Tyr Arg Ala Ser Phe Cys Arg Lys Thr Cys
            20                  25                  30

Gly Thr Cys
        35

<210> SEQ ID NO 21
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 21

Arg Ser Cys Ile Asp Ala Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 22
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (35)..(35)
<223> OTHER INFORMATION: AMIDATION

<400> SEQUENCE: 22

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35
```

<210> SEQ ID NO 23
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 23

Arg Ser Cys Ile Asp Tyr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 24
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 24

Arg Ser Cys Ile Asp Leu Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 25
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 25

Arg Ser Cys Ile Asp Thr Ala Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 26
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 26

Arg Ser Cys Ala Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 27

```
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 27

Arg Ser Cys Ile Asp Thr Ile Ala Lys Ser Arg Cys Thr Ala Phe Gln
1               5                   10                  15

Cys Lys His Ser Met Lys Tyr Arg Leu Ser Phe Cys Lys Thr Cys
            20                  25                  30

Gly Thr Cys
        35

<210> SEQ ID NO 28
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 28

Arg Ser Cys Ile Asp Thr Ile Pro Ala Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 29
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 29

Arg Ser Cys Ile Asp Thr Ile Pro Glu Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 30
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 30

Arg Ser Cys Ile Asp Thr Ile Pro Gln Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 31
<211> LENGTH: 35
<212> TYPE: PRT
<213> ORGANISM: Artificial Sequence
```

```
<220> FEATURE:
<223> OTHER INFORMATION: ShK-Based Peptide

<400> SEQUENCE: 31

Arg Ser Cys Ile Asp Thr Ile Pro Lys Ala Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 32
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 32

Arg Ser Cys Ile Asp Thr Ile Pro Lys Ser Ala Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 33
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 33

Arg Ser Cys Ile Asp Thr Ile Pro Lys Ser Glu Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 34
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 34

Arg Ser Cys Ile Asp Thr Ile Pro Lys Ser Gln Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 35
<211> LENGTH: 35
<212> TYPE: PRT
<213> ORGANISM: Artificial Sequence
<220> FEATURE:
<223> OTHER INFORMATION: ShK-Based Peptide
```

```
<400> SEQUENCE: 35

Arg Ser Cys Ile Asp Thr Ile Pro Lys Ser Arg Cys Ala Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 36
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 36

Arg Ser Cys Ile Asp Thr Ile Pro Lys Ser Arg Cys Thr Ala Ala Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 37
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 37

Arg Ser Cys Ile Asp Thr Ile Pro Lys Ser Arg Cys Thr Ala Trp Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 38
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (15)..(15)
<223> OTHER INFORMATION: Any nonfunctional amino acid residue

<400> SEQUENCE: 38

Arg Ser Cys Ile Asp Thr Ile Pro Lys Ser Arg Cys Thr Ala Xaa Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 39
<211> LENGTH: 35
<212> TYPE: PRT
<213> ORGANISM: Artificial Sequence
<220> FEATURE:
<223> OTHER INFORMATION: ShK-Based Peptide
```

<400> SEQUENCE: 39

Arg Ser Cys Ile Asp Thr Ile Pro Lys Ser Arg Cys Thr Ala Ala Gln
1               5                   10                  15

Cys Lys His Ser Met Lys Tyr Arg Ala Ser Phe Cys Arg Lys Thr Cys
            20                  25                  30

Gly Thr Cys
        35

<210> SEQ ID NO 40
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 40

Arg Ser Cys Ile Asp Thr Ile Pro Lys Ser Arg Cys Thr Ala Phe Ala
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 41
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 41

Arg Ser Cys Ile Asp Thr Ile Pro Lys Ser Arg Cys Thr Ala Phe Glu
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 42
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 42

Arg Ser Cys Ile Asp Thr Ile Pro Lys Ser Arg Cys Thr Ala Phe Gln
1               5                   10                  15

Cys Ala His Ser Met Lys Tyr Arg Leu Ser Phe Cys Arg Lys Thr Cys
            20                  25                  30

Gly Thr Cys
        35

<210> SEQ ID NO 43
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 43

-continued

Arg Ser Cys Ile Asp Thr Ile Pro Lys Ser Arg Cys Thr Ala Phe Gln
1               5                   10                  15

Cys Glu His Ser Met Lys Tyr Arg Leu Ser Phe Cys Lys Thr Cys
            20                  25                  30

Gly Thr Cys
        35

<210> SEQ ID NO 44
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 44

Arg Ser Cys Ile Asp Thr Ile Pro Lys Ser Arg Cys Thr Ala Phe Gln
1               5                   10                  15

Cys Lys Ala Ser Met Lys Tyr Arg Leu Ser Phe Cys Arg Lys Thr Cys
            20                  25                  30

Gly Thr Cys
        35

<210> SEQ ID NO 45
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 45

Arg Ser Cys Ile Asp Thr Ile Pro Lys Ser Arg Cys Thr Ala Phe Gln
1               5                   10                  15

Cys Lys Lys Ser Met Lys Tyr Arg Leu Ser Phe Cys Arg Lys Thr Cys
            20                  25                  30

Gly Thr Cys
        35

<210> SEQ ID NO 46
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 46

Arg Ser Cys Ile Asp Thr Ile Pro Lys Ser Arg Cys Thr Ala Phe Gln
1               5                   10                  15

Cys Lys His Ala Met Lys Tyr Arg Leu Ser Phe Cys Arg Lys Thr Cys
            20                  25                  30

Gly Thr Cys
        35

<210> SEQ ID NO 47
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 47

Arg Ser Cys Ile Asp Thr Ile Pro Lys Ser Arg Cys Thr Ala Phe Gln
1               5                   10                  15

```
Cys Lys His Ser Ala Lys Tyr Arg Leu Ser Phe Cys Arg Lys Thr Cys
            20                  25                  30

Gly Thr Cys
        35

<210> SEQ ID NO 48
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Any nonfunctional amino acid residue

<400> SEQUENCE: 48

Arg Ser Cys Ile Asp Thr Ile Pro Lys Ser Arg Cys Thr Ala Phe Gln
1               5                   10                  15

Cys Lys His Ser Xaa Lys Tyr Arg Leu Ser Phe Cys Arg Lys Thr Cys
            20                  25                  30

Gly Thr Cys
        35

<210> SEQ ID NO 49
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Nle

<400> SEQUENCE: 49

Arg Ser Cys Ile Asp Thr Ile Pro Lys Ser Arg Cys Thr Ala Phe Gln
1               5                   10                  15

Cys Lys His Ser Xaa Lys Tyr Arg Leu Ser Phe Cys Arg Lys Thr Cys
            20                  25                  30

Gly Thr Cys
        35

<210> SEQ ID NO 50
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 50

Arg Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 51
<211> LENGTH: 35
<212> TYPE: PRT
<213> ORGANISM: Artificial Sequence
<220> FEATURE:
<223> OTHER INFORMATION: ShK-Based Peptide
```

```
<400> SEQUENCE: 51

Arg Ser Cys Ile Asp Thr Ile Pro Lys Ser Arg Cys Thr Ala Phe Gln
1               5                   10                  15

Cys Lys His Ser Met Glu Tyr Arg Leu Ser Phe Cys Arg Lys Thr Cys
            20                  25                  30

Gly Thr Cys
        35

<210> SEQ ID NO 52
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 52

Arg Ser Cys Ile Asp Thr Ile Pro Lys Ser Arg Cys Thr Ala Phe Gln
1               5                   10                  15

Cys Lys His Ser Met Arg Tyr Arg Leu Ser Phe Cys Arg Lys Thr Cys
            20                  25                  30

Gly Thr Cys
        35

<210> SEQ ID NO 53
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Any nonfunctional amino acid residue

<400> SEQUENCE: 53

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

<210> SEQ ID NO 54
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Nle

<400> SEQUENCE: 54

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

<210> SEQ ID NO 55
<211> LENGTH: 35
```

-continued

```
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Orn

<400> SEQUENCE: 55

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

<210> SEQ ID NO 56
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Homocitrulline

<400> SEQUENCE: 56

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

<210> SEQ ID NO 57
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MISC_FEATURE
<222> LOCATION: (22)..(22)
<223> OTHER INFORMATION: Diaminopropionic acid

<400> SEQUENCE: 57

Arg Ser Cys Ile Asp Thr Ile Pro Lys Ser Arg Cys Thr Ala Phe Gln
1               5                   10                  15

Cys Lys His Ser Met Xaa Tyr Arg Leu Ser Phe Cys Arg Lys Thr Cys
            20                  25                  30

Gly Thr Cys
        35

<210> SEQ ID NO 58
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 58

Arg Ser Cys Ile Asp Thr Ile Pro Lys Ser Arg Cys Thr Ala Phe Gln
1               5                   10                  15
```

Cys Lys His Ser Met Lys Ala Arg Leu Ser Phe Cys Arg Lys Thr Cys
            20                  25                  30

Gly Thr Cys
        35

<210> SEQ ID NO 59
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 59

Arg Ser Cys Ile Asp Thr Ile Pro Lys Ser Arg Cys Thr Ala Phe Gln
1               5                   10                  15

Cys Lys His Ser Met Lys Ser Arg Leu Ser Phe Cys Arg Lys Thr Cys
            20                  25                  30

Gly Thr Cys
        35

<210> SEQ ID NO 60
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 60

Arg Ser Cys Ile Asp Thr Ile Pro Lys Ser Arg Cys Thr Ala Phe Gln
1               5                   10                  15

Cys Lys His Ser Met Lys Phe Arg Leu Ser Phe Cys Arg Lys Thr Cys
            20                  25                  30

Gly Thr Cys
        35

<210> SEQ ID NO 61
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (23)..(23)
<223> OTHER INFORMATION: Any nonfunctional amino acid residue

<400> SEQUENCE: 61

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
            20                  25                  30

Gly Thr Cys
        35

<210> SEQ ID NO 62
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (23)..(23)
<223> OTHER INFORMATION: Nitrophenylalanine

```
<400> SEQUENCE: 62

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
            20                  25                  30

Gly Thr Cys
        35

<210> SEQ ID NO 63
<211> LENGTH: 36
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (23)..(23)
<223> OTHER INFORMATION: Aminophenylalanine

<400> SEQUENCE: 63

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
            20                  25                  30

Gly Thr Cys Cys
        35

<210> SEQ ID NO 64
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (23)..(23)
<223> OTHER INFORMATION: Benzylphenylalanine

<400> SEQUENCE: 64

Arg Ser Cys Ile Asp Thr Ile Pro Lys Ser Arg Cys Thr Ala Phe Gln
1               5                   10                  15

Cys Lys His Ser Met Lys Xaa Arg Leu Ser Phe Cys Arg Lys Thr Cys
            20                  25                  30

Gly Thr Cys
        35

<210> SEQ ID NO 65
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 65

Arg Ser Cys Ile Asp Thr Ile Pro Lys Ser Arg Cys Thr Ala Phe Gln
1               5                   10                  15

Cys Lys His Ser Met Lys Tyr Ala Leu Ser Phe Cys Arg Lys Thr Cys
            20                  25                  30

Gly Thr Cys
        35

<210> SEQ ID NO 66
<211> LENGTH: 35
```

```
<212> TYPE: PRT
<213> ORGANISM: Artificial Sequence
<220> FEATURE:
<223> OTHER INFORMATION: ShK-Based Peptide

<400> SEQUENCE: 66

Arg Ser Cys Ile Asp Thr Ile Pro Lys Ser Arg Cys Thr Ala Phe Gln
1               5                   10                  15

Cys Lys His Ser Met Lys Tyr Glu Leu Ser Phe Cys Arg Lys Thr Cys
            20                  25                  30

Gly Thr Cys
        35

<210> SEQ ID NO 67
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 67

Arg Ser Cys Ile Asp Thr Ile Pro Lys Ser Arg Cys Thr Ala Phe Gln
1               5                   10                  15

Cys Lys His Ser Met Lys Tyr Arg Ala Ser Phe Cys Arg Lys Thr Cys
            20                  25                  30

Gly Thr Cys
        35

<210> SEQ ID NO 68
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 68

Arg Ser Cys Ile Asp Thr Ile Pro Lys Ser Arg Cys Thr Ala Phe Gln
1               5                   10                  15

Cys Lys His Ser Met Lys Tyr Arg Leu Ala Phe Cys Arg Lys Thr Cys
            20                  25                  30

Gly Thr Cys
        35

<210> SEQ ID NO 69
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 69

Arg Ser Cys Ile Asp Thr Ile Pro Lys Ser Arg Cys Thr Ala Phe Gln
1               5                   10                  15

Cys Lys His Ser Met Lys Tyr Arg Leu Ser Ala Cys Arg Lys Thr Cys
            20                  25                  30

Gly Thr Cys
        35

<210> SEQ ID NO 70
<211> LENGTH: 35
<212> TYPE: PRT
<213> ORGANISM: Artificial Sequence
<220> FEATURE:
```

<223> OTHER INFORMATION: ShK-Based Peptide
<220> FEATURE:
<221> NAME/KEY: MOD_RES
<222> LOCATION: (27)..(27)
<223> OTHER INFORMATION: Any nonfunctional amino acid residue

<400> SEQUENCE: 70

Arg Ser Cys Ile Asp Thr Ile Pro Lys Ser Arg Cys Thr Ala Phe Gln
1               5                   10                  15

Cys Lys His Ser Met Lys Tyr Arg Leu Ser Xaa Cys Lys Thr Cys
            20                  25                  30

Gly Thr Cys
        35

<210> SEQ ID NO 71
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 71

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Ala Lys Thr Cys
            20                  25                  30

Gly Thr Cys
        35

<210> SEQ ID NO 72
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 72

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Ala Thr Cys
            20                  25                  30

Gly Thr Cys
        35

<210> SEQ ID NO 73
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 73

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Ala Cys
            20                  25                  30

Gly Thr Cys
        35

<210> SEQ ID NO 74
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 74

Arg Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Ala Cys
        35

<210> SEQ ID NO 75
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 75

Ser Cys Ala Asp Thr Ile Pro Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 76
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 76

Ser Cys Ala Asp Thr Ile Pro Lys Ser Arg Cys Thr Ala Ala Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 77
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 77

Ser Cys Ala Asp Thr Ile Pro Lys Ser Arg Cys Thr Ala Ala Gln Cys
1               5                   10                  15

Lys His Ser Met Lys Tyr Arg Ala Ser Phe Cys Arg Lys Thr Cys Gly
            20                  25                  30

Thr Cys

<210> SEQ ID NO 78
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 78

Ser Cys Ile Asp Ala Ile Pro Lys Ser Arg Cys Thr Ala Phe Gln Cys

```
                1               5                   10                  15
Lys His Ser Met Lys Tyr Arg Leu Ser Phe Cys Arg Lys Thr Cys Gly
            20                  25                  30

Thr Cys

<210> SEQ ID NO 79
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 79

Ser Cys Ile Asp Thr Ala Pro Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 80
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 80

Ser Cys Ile Asp Thr Ile Ala Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 81
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 81

Ser Cys Ile Asp Thr Ile Pro Ala Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 82
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 82

Ser Cys Ile Asp Thr Ile Pro Glu Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys
```

<210> SEQ ID NO 83
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 83

Ser Cys Ile Asp Thr Ile Pro Gln Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 84
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 84

Ser Cys Ile Asp Thr Ile Pro Lys Ala Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 85
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 85

Ser Cys Ile Asp Thr Ile Pro Lys Ser Ala Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 86
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 86

Ser Cys Ile Asp Thr Ile Pro Lys Ser Glu Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 87
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 87

Ser Cys Ile Asp Thr Ile Pro Lys Ser Gln Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 88
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 88

Ser Cys Ile Asp Thr Ile Pro Lys Ser Arg Cys Ala Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 89
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 89

Ser Cys Ile Asp Thr Ile Pro Lys Ser Arg Cys Thr Ala Ala Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 90
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 90

Ser Cys Ile Asp Thr Ile Pro Lys Ser Arg Cys Thr Ala Trp Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 91
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (14)..(14)
<223> OTHER INFORMATION: Any nonfunctional amino acid residue

<400> SEQUENCE: 91

-continued

Ser Cys Ile Asp Thr Ile Pro Lys Ser Arg Cys Thr Ala Xaa Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 92
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 92

Ser Cys Ile Asp Thr Ile Pro Lys Ser Arg Cys Thr Ala Ala Gln Cys
1               5                   10                  15

Lys His Ser Met Lys Tyr Arg Ala Ser Phe Cys Arg Lys Thr Cys Gly
            20                  25                  30

Thr Cys

<210> SEQ ID NO 93
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 93

Ser Cys Ile Asp Thr Ile Pro Lys Ser Arg Cys Thr Ala Phe Ala Cys
1               5                   10                  15

Lys His Ser Met Lys Tyr Arg Leu Ser Phe Cys Arg Lys Thr Cys Gly
            20                  25                  30

Thr Cys

<210> SEQ ID NO 94
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 94

Ser Cys Ile Asp Thr Ile Pro Lys Ser Arg Cys Thr Ala Phe Glu Cys
1               5                   10                  15

Lys His Ser Met Lys Tyr Arg Leu Ser Phe Cys Arg Lys Thr Cys Gly
            20                  25                  30

Thr Cys

<210> SEQ ID NO 95
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 95

Ser Cys Ile Asp Thr Ile Pro Lys Ser Arg Cys Thr Ala Phe Gln Cys
1               5                   10                  15

Ala His Ser Met Lys Tyr Arg Leu Ser Phe Cys Arg Lys Thr Cys Gly
            20                  25                  30

Thr Cys

<210> SEQ ID NO 96
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 96

Ser Cys Ile Asp Thr Ile Pro Lys Ser Arg Cys Thr Ala Phe Gln Cys
1               5                   10                  15

Glu His Ser Met Lys Tyr Arg Leu Ser Phe Cys Arg Lys Thr Cys Gly
            20                  25                  30

Thr Cys

<210> SEQ ID NO 97
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 97

Ser Cys Ile Asp Thr Ile Pro Lys Ser Arg Cys Thr Ala Phe Gln Cys
1               5                   10                  15

Lys Ala Ser Met Lys Tyr Arg Leu Ser Phe Cys Arg Lys Thr Cys Gly
            20                  25                  30

Thr Cys

<210> SEQ ID NO 98
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 98

Ser Cys Ile Asp Thr Ile Pro Lys Ser Arg Cys Thr Ala Phe Gln Cys
1               5                   10                  15

Lys Lys Ser Met Lys Tyr Arg Leu Ser Phe Cys Arg Lys Thr Cys Gly
            20                  25                  30

Thr Cys

<210> SEQ ID NO 99
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 99

Ser Cys Ile Asp Thr Ile Pro Lys Ser Arg Cys Thr Ala Phe Gln Cys
1               5                   10                  15

Lys His Ala Met Lys Tyr Arg Leu Ser Phe Cys Arg Lys Thr Cys Gly
            20                  25                  30

Thr Cys

<210> SEQ ID NO 100
<211> LENGTH: 34
<212> TYPE: PRT
<213> ORGANISM: Artificial Sequence
<220> FEATURE:

<223> OTHER INFORMATION: ShK-Based Peptide

<400> SEQUENCE: 100

Ser Cys Ile Asp Thr Ile Pro Lys Ser Arg Cys Thr Ala Phe Gln Cys
1               5                   10                  15

Lys His Ser Ala Lys Tyr Arg Leu Ser Phe Cys Arg Lys Thr Cys Gly
            20                  25                  30

Thr Cys

<210> SEQ ID NO 101
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (20)..(20)
<223> OTHER INFORMATION: Any nonfunctional amino acid residue

<400> SEQUENCE: 101

Ser Cys Ile Asp Thr Ile Pro Lys Ser Arg Cys Thr Ala Phe Gln Cys
1               5                   10                  15

Lys His Ser Xaa Lys Tyr Arg Leu Ser Phe Cys Arg Lys Thr Cys Gly
            20                  25                  30

Thr Cys

<210> SEQ ID NO 102
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (20)..(20)
<223> OTHER INFORMATION: Nle

<400> SEQUENCE: 102

Ser Cys Ile Asp Thr Ile Pro Lys Ser Arg Cys Thr Ala Phe Gln Cys
1               5                   10                  15

Lys His Ser Xaa Lys Tyr Arg Leu Ser Phe Cys Arg Lys Thr Cys Gly
            20                  25                  30

Thr Cys

<210> SEQ ID NO 103
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 103

Ser Cys Ile Asp Thr Ile Pro Lys Ser Arg Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 104
<211> LENGTH: 34
<212> TYPE: PRT
<213> ORGANISM: Artificial Sequence

```
<220> FEATURE:
<223> OTHER INFORMATION: ShK-Based Peptide

<400> SEQUENCE: 104

Ser Cys Ile Asp Thr Ile Pro Lys Ser Arg Cys Thr Ala Phe Gln Cys
1               5                   10                  15

Lys His Ser Met Glu Tyr Arg Leu Ser Phe Cys Arg Lys Thr Cys Gly
            20                  25                  30

Thr Cys

<210> SEQ ID NO 105
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 105

Ser Cys Ile Asp Thr Ile Pro Lys Ser Arg Cys Thr Ala Phe Gln Cys
1               5                   10                  15

Lys His Ser Met Arg Tyr Arg Leu Ser Phe Cys Arg Lys Thr Cys Gly
            20                  25                  30

Thr Cys

<210> SEQ ID NO 106
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Any nonfunctional amino acid residue

<400> SEQUENCE: 106

Ser Cys Ile Asp Thr Ile Pro Lys Ser Arg Cys Thr Ala Phe Gln Cys
1               5                   10                  15

Lys His Ser Met Xaa Tyr Arg Leu Ser Phe Cys Arg Lys Thr Cys Gly
            20                  25                  30

Thr Cys

<210> SEQ ID NO 107
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Nle

<400> SEQUENCE: 107

Ser Cys Ile Asp Thr Ile Pro Lys Ser Arg Cys Thr Ala Phe Gln Cys
1               5                   10                  15

Lys His Ser Met Xaa Tyr Arg Leu Ser Phe Cys Arg Lys Thr Cys Gly
            20                  25                  30

Thr Cys

<210> SEQ ID NO 108
<211> LENGTH: 34
<212> TYPE: PRT
```

<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Orn

<400> SEQUENCE: 108

Ser Cys Ile Asp Thr Ile Pro Lys Ser Arg Cys Thr Ala Phe Gln Cys
1               5                   10                  15

Lys His Ser Met Xaa Tyr Arg Leu Ser Phe Cys Arg Lys Thr Cys Gly
            20                  25                  30

Thr Cys

<210> SEQ ID NO 109
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Homocitrulline

<400> SEQUENCE: 109

Ser Cys Ile Asp Thr Ile Pro Lys Ser Arg Cys Thr Ala Phe Gln Cys
1               5                   10                  15

Lys His Ser Met Xaa Tyr Arg Leu Ser Phe Cys Arg Lys Thr Cys Gly
            20                  25                  30

Thr Cys

<210> SEQ ID NO 110
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MISC_FEATURE
<222> LOCATION: (21)..(21)
<223> OTHER INFORMATION: Diaminopropionic acid

<400> SEQUENCE: 110

Ser Cys Ile Asp Thr Ile Pro Lys Ser Arg Cys Thr Ala Phe Gln Cys
1               5                   10                  15

Lys His Ser Met Xaa Tyr Arg Leu Ser Phe Cys Arg Lys Thr Cys Gly
            20                  25                  30

Thr Cys

<210> SEQ ID NO 111
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 111

Ser Cys Ile Asp Thr Ile Pro Lys Ser Arg Cys Thr Ala Phe Gln Cys
1               5                   10                  15

Lys His Ser Met Lys Ala Arg Leu Ser Phe Cys Arg Lys Thr Cys Gly
            20                  25                  30

Thr Cys

<210> SEQ ID NO 112
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 112

Ser Cys Ile Asp Thr Ile Pro Lys Ser Arg Cys Thr Ala Phe Gln Cys
1               5                   10                  15

Lys His Ser Met Lys Ser Arg Leu Ser Phe Cys Arg Lys Thr Cys Gly
            20                  25                  30

Thr Cys

<210> SEQ ID NO 113
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 113

Ser Cys Ile Asp Thr Ile Pro Lys Ser Arg Cys Thr Ala Phe Gln Cys
1               5                   10                  15

Lys His Ser Met Lys Phe Arg Leu Ser Phe Cys Arg Lys Thr Cys Gly
            20                  25                  30

Thr Cys

<210> SEQ ID NO 114
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Any nonfunctional amino acid residue

<400> SEQUENCE: 114

Ser Cys Ile Asp Thr Ile Pro Lys Ser Arg Cys Thr Ala Phe Gln Cys
1               5                   10                  15

Lys His Ser Met Lys Xaa Arg Leu Ser Phe Cys Arg Lys Thr Cys Gly
            20                  25                  30

Thr Cys

<210> SEQ ID NO 115
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Nitrophenylalanine

<400> SEQUENCE: 115

Ser Cys Ile Asp Thr Ile Pro Lys Ser Arg Cys Thr Ala Phe Gln Cys
1               5                   10                  15

Lys His Ser Met Lys Xaa Arg Leu Ser Phe Cys Arg Lys Thr Cys Gly
            20                  25                  30

Thr Cys

<210> SEQ ID NO 116
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Aminophenylalanine

<400> SEQUENCE: 116

Ser Cys Ile Asp Thr Ile Pro Lys Ser Arg Cys Thr Ala Phe Gln Cys
1               5                   10                  15

Lys His Ser Met Lys Xaa Arg Leu Ser Phe Cys Arg Lys Thr Cys Gly
            20                  25                  30

Thr Cys

<210> SEQ ID NO 117
<211> LENGTH: 33
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (22)..(22)
<223> OTHER INFORMATION: Benzylphenylalanine

<400> SEQUENCE: 117

Ser Cys Ile Asp Thr Ile Pro Lys Ser Arg Cys Thr Ala Phe Gln Cys
1               5                   10                  15

Lys His Ser Met Lys Xaa Arg Leu Ser Phe Cys Arg Lys Thr Cys Gly
            20                  25                  30

Thr

<210> SEQ ID NO 118
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 118

Ser Cys Ile Asp Thr Ile Pro Lys Ser Arg Cys Thr Ala Phe Gln Cys
1               5                   10                  15

Lys His Ser Met Lys Tyr Ala Leu Ser Phe Cys Arg Lys Thr Cys Gly
            20                  25                  30

Thr Cys

<210> SEQ ID NO 119
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 119

Ser Cys Ile Asp Thr Ile Pro Lys Ser Arg Cys Thr Ala Phe Gln Cys
1               5                   10                  15

Lys His Ser Met Lys Tyr Glu Leu Ser Phe Cys Arg Lys Thr Cys Gly
            20                  25                  30

Thr Cys

<210> SEQ ID NO 120
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 120

Ser Cys Ile Asp Thr Ile Pro Lys Ser Arg Cys Thr Ala Phe Gln Cys
1               5                   10                  15

Lys His Ser Met Lys Tyr Arg Ala Ser Phe Cys Arg Lys Thr Cys Gly
            20                  25                  30

Thr Cys

<210> SEQ ID NO 121
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 121

Ser Cys Ile Asp Thr Ile Pro Lys Ser Arg Cys Thr Ala Phe Gln Cys
1               5                   10                  15

Lys His Ser Met Lys Tyr Arg Leu Ala Phe Cys Arg Lys Thr Cys Gly
            20                  25                  30

Thr Cys

<210> SEQ ID NO 122
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 122

Ser Cys Ile Asp Thr Ile Pro Lys Ser Arg Cys Thr Ala Phe Gln Cys
1               5                   10                  15

Lys His Ser Met Lys Tyr Arg Leu Ser Ala Cys Arg Lys Thr Cys Gly
            20                  25                  30

Thr Cys

<210> SEQ ID NO 123
<211> LENGTH: 34
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (26)..(26)
<223> OTHER INFORMATION: Any nonfunctional amino acid residue

<400> SEQUENCE: 123

Ser Cys Ile Asp Thr Ile Pro Lys Ser Arg Cys Thr Ala Phe Gln Cys
1               5                   10                  15

Lys His Ser Met Lys Tyr Arg Leu Ser Xaa Cys Arg Lys Thr Cys Gly
            20                  25                  30

Thr Cys

<210> SEQ ID NO 124
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 124

Ser Cys Ile Asp Thr Ile Pro Lys Ser Arg Cys Thr Ala Phe Gln Cys
1               5                   10                  15

Lys His Ser Met Lys Tyr Arg Leu Ser Phe Cys Ala Lys Thr Cys Gly
            20                  25                  30

Thr Cys

<210> SEQ ID NO 125
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 125

Ser Cys Ile Asp Thr Ile Pro Lys Ser Arg Cys Thr Ala Phe Gln Cys
1               5                   10                  15

Lys His Ser Met Lys Tyr Arg Leu Ser Phe Cys Arg Ala Thr Cys Gly
            20                  25                  30

Thr Cys

<210> SEQ ID NO 126
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 126

Ser Cys Ile Asp Thr Ile Pro Lys Ser Arg Cys Thr Ala Phe Gln Cys
1               5                   10                  15

Lys His Ser Met Lys Tyr Arg Leu Ser Phe Cys Arg Lys Ala Cys Gly
            20                  25                  30

Thr Cys

<210> SEQ ID NO 127
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 127

Ser Cys Ile Asp Thr Ile Pro Lys Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Ala Cys

<210> SEQ ID NO 128
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 128

Tyr Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 129
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 129

Lys Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 130
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 130

His Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 131
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 131

Gln Ser Cys Ile Asp Thr Ile Pro Lys Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 132
<211> LENGTH: 37
<212> TYPE: PRT
<213> ORGANISM: Artificial Sequence
<220> FEATURE:
<223> OTHER INFORMATION: ShK-Based Peptide

<400> SEQUENCE: 132

-continued

Pro Pro Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
            35

<210> SEQ ID NO 133
<211> LENGTH: 36
<212> TYPE: PRT
<213> ORGANISM: Artificial Sequence
<220> FEATURE:
<223> OTHER INFORMATION: ShK-Based Peptide

<400> SEQUENCE: 133

Met Arg Ser Cys Ile Asp Thr Ile Pro Lys Ser Arg Cys Thr Ala Phe
1               5                   10                  15

Gln Cys Lys His Ser Met Lys Tyr Arg Leu Ser Phe Cys Arg Lys Thr
            20                  25                  30

Cys Gly Thr Cys
            35

<210> SEQ ID NO 134
<211> LENGTH: 36
<212> TYPE: PRT
<213> ORGANISM: Artificial Sequence
<220> FEATURE:
<223> OTHER INFORMATION: ShK-Based Peptide

<400> SEQUENCE: 134

Gly Arg Ser Cys Ile Asp Thr Ile Pro Lys Ser Arg Cys Thr Ala Phe
1               5                   10                  15

Gln Cys Lys His Ser Met Lys Tyr Arg Leu Ser Phe Cys Arg Lys Thr
            20                  25                  30

Cys Gly Thr Cys
            35

<210> SEQ ID NO 135
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 135

Tyr Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
            35

<210> SEQ ID NO 136
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 136

Lys Ser Cys Ile Asp Thr Ile Pro Lys Ser Arg Cys Thr Ala Phe Gln
1               5                   10                  15

```
Cys Lys His Ser Met Ala Tyr Arg Leu Ser Phe Cys Lys Thr Cys
            20                  25                  30

Gly Thr Cys
        35
```

<210> SEQ ID NO 137
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 137

```
His Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Lys Thr Cys
            20                  25                  30

Gly Thr Cys
        35
```

<210> SEQ ID NO 138
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 138

```
Gln Ser Cys Ile Asp Thr Ile Pro Lys Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35
```

<210> SEQ ID NO 139
<211> LENGTH: 37
<212> TYPE: PRT
<213> ORGANISM: Artificial Sequence
<220> FEATURE:
<223> OTHER INFORMATION: ShK-Based Peptide

<400> SEQUENCE: 139

```
Pro Pro Arg Ser Cys Ile Asp Thr Ile Pro Lys Ser Arg Cys Thr Ala
1               5                   10                  15

Phe Gln Cys Lys His Ser Met Ala Tyr Arg Leu Ser Phe Cys Arg Lys
            20                  25                  30

Thr Cys Gly Thr Cys
        35
```

<210> SEQ ID NO 140
<211> LENGTH: 36
<212> TYPE: PRT
<213> ORGANISM: Artificial Sequence
<220> FEATURE:
<223> OTHER INFORMATION: ShK-Based Peptide

<400> SEQUENCE: 140

```
Met Arg Ser Cys Ile Asp Thr Ile Pro Lys Ser Arg Cys Thr Ala Phe
1               5                   10                  15

Gln Cys Lys His Ser Met Ala Tyr Arg Leu Ser Phe Cys Arg Lys Thr
            20                  25                  30
```

Cys Gly Thr Cys
        35

<210> SEQ ID NO 141
<211> LENGTH: 36
<212> TYPE: PRT
<213> ORGANISM: Artificial Sequence
<220> FEATURE:
<223> OTHER INFORMATION: ShK-Based Peptide

<400> SEQUENCE: 141

Gly Arg Ser Cys Ile Asp Thr Ile Pro Lys Ser Arg Cys Thr Ala Phe
1               5                   10                  15

Gln Cys Lys His Ser Met Ala Tyr Arg Leu Ser Phe Cys Arg Lys Thr
            20                  25                  30

Cys Gly Thr Cys
        35

<210> SEQ ID NO 142
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 142

Arg Ser Cys Ile Asp Thr Ile Pro Ala Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 143
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 143

Ser Cys Ile Asp Thr Ile Pro Ala Ser Arg Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 144
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 144

Arg Ser Cys Ile Asp Thr Ile Pro Val Ser Arg Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

```
<210> SEQ ID NO 145
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 145

Arg Ser Cys Ile Asp Thr Ile Pro Val Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 146
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 146

Ser Cys Ile Asp Thr Ile Pro Val Ser Arg Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 147
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 147

Ser Cys Ile Asp Thr Ile Pro Val Ser Arg Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 148
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 148

Arg Ser Cys Ile Asp Thr Ile Pro Glu Ser Arg Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 149
<211> LENGTH: 34
<212> TYPE: PRT
<213> ORGANISM: Artificial Sequence
<220> FEATURE:
```

<223> OTHER INFORMATION: ShK-Based Peptide

<400> SEQUENCE: 149

Ser Cys Ile Asp Thr Ile Pro Glu Ser Arg Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 150
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 150

Arg Ser Cys Ile Asp Thr Ile Pro Lys Ser Ala Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 151
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 151

Ser Cys Ile Asp Thr Ile Pro Lys Ser Ala Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 152
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 152

Arg Ser Cys Ile Asp Thr Ile Pro Lys Ser Glu Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 153
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 153

Ser Cys Ile Asp Thr Ile Pro Lys Ser Glu Cys Thr Ala Phe Gln Cys

```
                1               5                  10                  15
Lys His Ser Met Ala Tyr Arg Leu Ser Phe Cys Arg Lys Thr Cys Gly
            20                  25                  30

Thr Cys
```

<210> SEQ ID NO 154
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 154

```
Arg Ser Cys Ile Asp Thr Ile Pro Lys Ser Arg Cys Thr Asp Phe Gln
1               5                   10                  15

Cys Lys His Ser Met Lys Tyr Arg Leu Ser Phe Cys Arg Lys Thr Cys
            20                  25                  30

Gly Thr Cys
        35
```

<210> SEQ ID NO 155
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 155

```
Arg Ser Cys Ile Asp Thr Ile Pro Lys Ser Arg Cys Thr Asp Phe Gln
1               5                   10                  15

Cys Lys His Ser Met Ala Tyr Arg Leu Ser Phe Cys Arg Lys Thr Cys
            20                  25                  30

Gly Thr Cys
        35
```

<210> SEQ ID NO 156
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 156

```
Ser Cys Ile Asp Thr Ile Pro Lys Ser Arg Cys Thr Asp Phe Gln Cys
1               5                   10                  15

Lys His Ser Met Lys Tyr Arg Leu Ser Phe Cys Arg Lys Thr Cys Gly
            20                  25                  30

Thr Cys
```

<210> SEQ ID NO 157
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 157

```
Ser Cys Ile Asp Thr Ile Pro Lys Ser Arg Cys Thr Asp Phe Gln Cys
1               5                   10                  15

Lys His Ser Met Ala Tyr Arg Leu Ser Phe Cys Arg Lys Thr Cys Gly
            20                  25                  30
```

Thr Cys

<210> SEQ ID NO 158
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 158

Arg Ser Cys Ile Asp Thr Ile Pro Lys Ser Arg Cys Thr Ala Ala Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 159
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 159

Ser Cys Ile Asp Thr Ile Pro Lys Ser Arg Cys Thr Ala Ala Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 160
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 160

Arg Ser Cys Ile Asp Thr Ile Pro Lys Ser Arg Cys Thr Ala Ile Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 161
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 161

Arg Ser Cys Ile Asp Thr Ile Pro Lys Ser Arg Cys Thr Ala Ile Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 162

```
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 162

Ser Cys Ile Asp Thr Ile Pro Lys Ser Arg Cys Thr Ala Ile Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 163
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 163

Ser Cys Ile Asp Thr Ile Pro Lys Ser Arg Cys Thr Ala Ile Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 164
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 164

Arg Ser Cys Ile Asp Thr Ile Pro Lys Ser Arg Cys Thr Ala Val Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 165
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 165

Arg Ser Cys Ile Asp Thr Ile Pro Lys Ser Arg Cys Thr Ala Val Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 166
<211> LENGTH: 34
<212> TYPE: PRT
<213> ORGANISM: Artificial Sequence
<220> FEATURE:
<223> OTHER INFORMATION: ShK-Based Peptide
```

```
<400> SEQUENCE: 166

Ser Cys Ile Asp Thr Ile Pro Lys Ser Arg Cys Thr Ala Val Gln Cys
1               5                   10                  15

Lys His Ser Met Lys Tyr Arg Leu Ser Phe Cys Arg Lys Thr Cys Gly
                20                  25                  30

Thr Cys

<210> SEQ ID NO 167
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 167

Ser Cys Ile Asp Thr Ile Pro Lys Ser Arg Cys Thr Ala Val Gln Cys
1               5                   10                  15

Lys His Ser Met Ala Tyr Arg Leu Ser Phe Cys Arg Lys Thr Cys Gly
                20                  25                  30

Thr Cys

<210> SEQ ID NO 168
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 168

Arg Ser Cys Ile Asp Thr Ile Pro Lys Ser Arg Cys Thr Ala Phe Arg
1               5                   10                  15

Cys Lys His Ser Met Lys Tyr Arg Leu Ser Phe Cys Arg Lys Thr Cys
                20                  25                  30

Gly Thr Cys
        35

<210> SEQ ID NO 169
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 169

Arg Ser Cys Ile Asp Thr Ile Pro Lys Ser Arg Cys Thr Ala Phe Arg
1               5                   10                  15

Cys Lys His Ser Met Ala Tyr Arg Leu Ser Phe Cys Arg Lys Thr Cys
                20                  25                  30

Gly Thr Cys
        35

<210> SEQ ID NO 170
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 170

Ser Cys Ile Asp Thr Ile Pro Lys Ser Arg Cys Thr Ala Phe Arg Cys
1               5                   10                  15
```

Lys His Ser Met Lys Tyr Arg Leu Ser Phe Cys Arg Lys Thr Cys Gly
            20                  25                  30

Thr Cys

<210> SEQ ID NO 171
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 171

Ser Cys Ile Asp Thr Ile Pro Lys Ser Arg Cys Thr Ala Phe Arg Cys
1               5                   10                  15

Lys His Ser Met Ala Tyr Arg Leu Ser Phe Cys Arg Lys Thr Cys Gly
            20                  25                  30

Thr Cys

<210> SEQ ID NO 172
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 172

Arg Ser Cys Ile Asp Thr Ile Pro Lys Ser Arg Cys Thr Ala Phe Lys
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 173
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 173

Arg Ser Cys Ile Asp Thr Ile Pro Lys Ser Arg Cys Thr Ala Phe Lys
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 174
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 174

Ser Cys Ile Asp Thr Ile Pro Lys Ser Arg Cys Thr Ala Phe Lys Cys
1               5                   10                  15

Lys His Ser Met Lys Tyr Arg Leu Ser Phe Cys Arg Lys Thr Cys Gly
            20                  25                  30

Thr Cys

```
<210> SEQ ID NO 175
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 175

Ser Cys Ile Asp Thr Ile Pro Lys Ser Arg Cys Thr Ala Phe Lys Cys
1               5                   10                  15

Lys His Ser Met Ala Tyr Arg Leu Ser Phe Cys Arg Lys Thr Cys Gly
            20                  25                  30

Thr Cys

<210> SEQ ID NO 176
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 176

Arg Ser Cys Ile Asp Thr Ile Pro Ala Ser Glu Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 177
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 177

Arg Ser Cys Ile Asp Thr Ile Pro Ala Ser Glu Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 178
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 178

Ser Cys Ile Asp Thr Ile Pro Ala Ser Glu Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 179
<211> LENGTH: 34
<212> TYPE: PRT
```

<213> ORGANISM: Artificial Sequence
<220> FEATURE:
<223> OTHER INFORMATION: ShK-Based Peptide

<400> SEQUENCE: 179

Ser Cys Ile Asp Thr Ile Pro Ala Ser Glu Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 180
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 180

Arg Ser Cys Ile Asp Thr Ile Pro Val Ser Glu Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 181
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 181

Arg Ser Cys Ile Asp Thr Ile Pro Val Ser Glu Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 182
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 182

Ser Cys Ile Asp Thr Ile Pro Val Ser Glu Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 183
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 183

Ser Cys Ile Asp Thr Ile Pro Val Ser Glu Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys

<210> SEQ ID NO 184
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 184

Arg Ser Cys Ile Asp Thr Ile Pro Val Ser Ala Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 185
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 185

Arg Ser Cys Ile Asp Thr Ile Pro Val Ser Ala Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 186
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 186

Ser Cys Ile Asp Thr Ile Pro Val Ser Ala Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 187
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 187

Ser Cys Ile Asp Thr Ile Pro Val Ser Ala Cys Thr Ala Phe Gln Cys
1               5                   10                  15

Lys His Ser Met Ala Tyr Arg Leu Ser Phe Cys Arg Lys Thr Cys Gly

```
                    20                  25                  30

Thr Cys

<210> SEQ ID NO 188
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 188

Arg Ser Cys Ile Asp Thr Ile Pro Ala Ser Ala Cys Thr Ala Phe Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 189
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 189

Arg Ser Cys Ile Asp Thr Ile Pro Ala Ser Ala Cys Thr Ala Phe Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 190
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 190

Ser Cys Ile Asp Thr Ile Pro Ala Ser Ala Cys Thr Ala Phe Gln Cys
1               5                   10                  15

Lys His Ser Met Lys Tyr Arg Leu Ser Phe Cys Arg Lys Thr Cys Gly
            20                  25                  30

Thr Cys

<210> SEQ ID NO 191
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 191

Ser Cys Ile Asp Thr Ile Pro Ala Ser Ala Cys Thr Ala Phe Gln Cys
1               5                   10                  15

Lys His Ser Met Ala Tyr Arg Leu Ser Phe Cys Arg Lys Thr Cys Gly
            20                  25                  30

Thr Cys
```

```
<210> SEQ ID NO 192
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 192

Arg Ser Cys Ile Asp Thr Ile Pro Lys Ser Glu Cys Thr Asp Ile Arg
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 193
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 193

Arg Ser Cys Ile Asp Thr Ile Pro Lys Ser Glu Cys Thr Asp Ile Arg
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 194
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 194

Ser Cys Ile Asp Thr Ile Pro Lys Ser Glu Cys Thr Asp Ile Arg Cys
1               5                   10                  15

Lys His Ser Met Lys Tyr Arg Leu Ser Phe Cys Arg Lys Thr Cys Gly
            20                  25                  30

Thr Cys

<210> SEQ ID NO 195
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 195

Ser Cys Ile Asp Thr Ile Pro Lys Ser Glu Cys Thr Asp Ile Arg Cys
1               5                   10                  15

Lys His Ser Met Ala Tyr Arg Leu Ser Phe Cys Arg Lys Thr Cys Gly
            20                  25                  30

Thr Cys

<210> SEQ ID NO 196
<211> LENGTH: 35
<212> TYPE: PRT
<213> ORGANISM: Artificial Sequence
<220> FEATURE:
```

<223> OTHER INFORMATION: ShK-Based Peptide

<400> SEQUENCE: 196

Arg Ser Cys Ile Asp Thr Ile Pro Val Ser Glu Cys Thr Asp Ile Arg
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 197
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 197

Arg Ser Cys Ile Asp Thr Ile Pro Val Ser Glu Cys Thr Asp Ile Arg
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 198
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 198

Ser Cys Ile Asp Thr Ile Pro Val Ser Glu Cys Thr Asp Ile Arg Cys
1               5                   10                  15

Lys His Ser Met Lys Tyr Arg Leu Ser Phe Cys Arg Lys Thr Cys Gly
            20                  25                  30

Thr Cys

<210> SEQ ID NO 199
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 199

Ser Cys Ile Asp Thr Ile Pro Val Ser Glu Cys Thr Asp Ile Arg Cys
1               5                   10                  15

Lys His Ser Met Ala Tyr Arg Leu Ser Phe Cys Arg Lys Thr Cys Gly
            20                  25                  30

Thr Cys

<210> SEQ ID NO 200
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 200

Arg Ser Cys Ile Asp Thr Ile Pro Val Ser Glu Cys Thr Asp Ile Gln

```
                1               5                  10                  15
Cys Lys His Ser Met Lys Tyr Arg Leu Ser Phe Cys Arg Lys Thr Cys
                20                  25                  30

Gly Thr Cys
        35

<210> SEQ ID NO 201
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 201

Arg Ser Cys Ile Asp Thr Ile Pro Val Ser Glu Cys Thr Asp Ile Gln
1               5                  10                  15

Cys Lys His Ser Met Ala Tyr Arg Leu Ser Phe Cys Arg Lys Thr Cys
                20                  25                  30

Gly Thr Cys
        35

<210> SEQ ID NO 202
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 202

Ser Cys Ile Asp Thr Ile Pro Val Ser Glu Cys Thr Asp Ile Gln Cys
1               5                  10                  15

Lys His Ser Met Lys Tyr Arg Leu Ser Phe Cys Arg Lys Thr Cys Gly
                20                  25                  30

Thr Cys

<210> SEQ ID NO 203
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 203

Ser Cys Ile Asp Thr Ile Pro Val Ser Glu Cys Thr Asp Ile Gln Cys
1               5                  10                  15

Lys His Ser Met Ala Tyr Arg Leu Ser Phe Cys Arg Lys Thr Cys Gly
                20                  25                  30

Thr Cys

<210> SEQ ID NO 204
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 204

Arg Thr Cys Lys Asp Leu Ile Pro Val Ser Glu Cys Thr Asp Ile Arg
1               5                  10                  15

Cys Lys His Ser Met Lys Tyr Arg Leu Ser Phe Cys Arg Lys Thr Cys
                20                  25                  30
```

Gly Thr Cys
        35

<210> SEQ ID NO 205
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 205

Arg Thr Cys Lys Asp Leu Ile Pro Val Ser Glu Cys Thr Asp Ile Arg
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 206
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 206

Thr Cys Lys Asp Leu Ile Pro Val Ser Glu Cys Thr Asp Ile Arg Cys
1               5                   10                  15

Lys His Ser Met Lys Tyr Arg Leu Ser Phe Cys Arg Lys Thr Cys Gly
            20                  25                  30

Thr Cys

<210> SEQ ID NO 207
<211> LENGTH: 34
<212> TYPE: PRT
<213> ORGANISM: Artificial Sequence
<220> FEATURE:
<223> OTHER INFORMATION: ShK-Based Peptide

<400> SEQUENCE: 207

Thr Cys Lys Asp Leu Ile Pro Val Ser Glu Cys Thr Asp Ile Arg Cys
1               5                   10                  15

Lys His Ser Met Ala Tyr Arg Leu Ser Phe Cys Arg Lys Thr Cys Gly
            20                  25                  30

Thr Cys

<210> SEQ ID NO 208
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: L-Phosphotyrosine
<220> FEATURE:
<221> NAME/KEY: MISC_FEATURE
<222> LOCATION: (2)..(2)
<223> OTHER INFORMATION: Aminoethyloxyethyloxyacetic acid

<400> SEQUENCE: 208

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 209
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: L-Tyrosine
<220> FEATURE:
<221> NAME/KEY: MISC_FEATURE
<222> LOCATION: (2)..(2)
<223> OTHER INFORMATION: Aminoethyloxyethyloxyacetic acid

<400> SEQUENCE: 209

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 210
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: L-Tyrosine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (37)..(37)
<223> OTHER INFORMATION: AMIDATION

<400> SEQUENCE: 210

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 211
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 211

Gln Ser Cys Ala Asp Thr Ile Pro Lys Ser Arg Cys Thr Ala Ala Gln
1               5                   10                  15

Cys Lys His Ser Met Lys Tyr Arg Leu Ser Phe Cys Arg Lys Thr Cys
            20                  25                  30

Gly Thr Cys
        35

<210> SEQ ID NO 212
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 212

Gln Ser Cys Ala Asp Thr Ile Pro Lys Ser Arg Cys Thr Ala Ala Gln
1               5                   10                  15

Cys Lys His Ser Met Ala Tyr Arg Leu Ser Phe Cys Arg Lys Thr Cys
            20                  25                  30

Gly Thr Cys
        35

<210> SEQ ID NO 213
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MISC_FEATURE
<222> LOCATION: (22)..(22)
<223> OTHER INFORMATION: Diaminopropionic acid

<400> SEQUENCE: 213

Gln Ser Cys Ala Asp Thr Ile Pro Lys Ser Arg Cys Thr Ala Ala Gln
1               5                   10                  15

Cys Lys His Ser Met Xaa Tyr Arg Leu Ser Phe Cys Arg Lys Thr Cys
            20                  25                  30

Gly Thr Cys
        35

<210> SEQ ID NO 214
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 214

Gln Ser Cys Ala Asp Thr Ile Pro Lys Ser Arg Cys Thr Ala Ala Gln
1               5                   10                  15

Cys Lys His Ser Met Lys Tyr Arg Ala Ser Phe Cys Arg Lys Thr Cys
            20                  25                  30

Gly Thr Cys
        35

<210> SEQ ID NO 215
<211> LENGTH: 35
<212> TYPE: PRT
<213> ORGANISM: Artificial Sequence
<220> FEATURE:
<223> OTHER INFORMATION: ShK-Based Peptide

<400> SEQUENCE: 215

Gln Ser Cys Ala Asp Thr Ile Pro Lys Ser Arg Cys Thr Ala Ala Gln
1               5                   10                  15

Cys Lys His Ser Met Ala Tyr Arg Ala Ser Phe Cys Arg Lys Thr Cys

```
<210> SEQ ID NO 216
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MISC_FEATURE
<222> LOCATION: (22)..(22)
<223> OTHER INFORMATION: Diaminopropionic acid

<400> SEQUENCE: 216

Gln Ser Cys Ala Asp Thr Ile Pro Lys Ser Arg Cys Thr Ala Ala Gln
1               5                   10                  15

Cys Lys His Ser Met Xaa Tyr Arg Ala Ser Phe Cys Arg Lys Thr Cys
            20                  25                  30

Gly Thr Cys
        35

<210> SEQ ID NO 217
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: L-Phosphotyrosine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (37)..(37)
<223> OTHER INFORMATION: AMIDATION

<400> SEQUENCE: 217

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 218
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: Para-phosphono-phenylalanine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
```

<222> LOCATION: (37)..(37)
<223> OTHER INFORMATION: AMIDATION

<400> SEQUENCE: 218

Xaa Xaa Arg Ser Cys Ile Asp Thr Ile Pro Lys Ser Arg Cys Thr Ala
1               5                   10                  15

Phe Gln Cys Lys His Ser Xaa Lys Tyr Arg Leu Ser Phe Cys Arg Lys
            20                  25                  30

Thr Cys Gly Thr Cys
        35

<210> SEQ ID NO 219
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: Phosphonomethyl-phenylalanine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (37)..(37)
<223> OTHER INFORMATION: AMIDATION

<400> SEQUENCE: 219

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
            20                  25                  30

Thr Cys Gly Thr Cys
        35

<210> SEQ ID NO 220
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: Phosphonomethyl-phenylalanine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (37)..(37)
<223> OTHER INFORMATION: AMIDATION

<400> SEQUENCE: 220

Xaa Xaa Arg Ser Cys Ile Asp Thr Ile Pro Lys Ser Arg Cys Thr Ala
1               5                   10                  15

Phe Gln Cys Lys His Ser Xaa Lys Tyr Arg Leu Ser Phe Cys Arg Lys
            20                  25                  30

Thr Cys Gly Thr Cys
        35

```
<210> SEQ ID NO 221
<211> LENGTH: 39
<212> TYPE: PRT
<213> ORGANISM: Artificial Sequence
<220> FEATURE:
<223> OTHER INFORMATION: ShK-Based Peptide
<220> FEATURE:
<221> NAME/KEY: MISC_FEATURE
<222> LOCATION: (1)..(1)
<223> OTHER INFORMATION: 1,4,7,10-tetraazacyclododecane-1,4,7,
      10-tetraacetic acid
<220> FEATURE:
<221> NAME/KEY: MISC_FEATURE
<222> LOCATION: (2)..(2)
<223> OTHER INFORMATION: aminohexanoicacid
<220> FEATURE:
<221> NAME/KEY: MOD_RES
<222> LOCATION: (3)..(3)
<223> OTHER INFORMATION: L-Tyrosine
<220> FEATURE:
<221> NAME/KEY: MISC_FEATURE
<222> LOCATION: (4)..(4)
<223> OTHER INFORMATION: Aminoethyloxyethyloxyacetic acid
<220> FEATURE:
<221> NAME/KEY: MOD_RES
<222> LOCATION: (39)..(39)
<223> OTHER INFORMATION: AMIDATION

<400> SEQUENCE: 221

Xaa Xaa Xaa Xaa Arg Ser Cys Ile Asp Thr Ile Pro Lys Ser Arg Cys
1               5                   10                  15

Thr Ala Phe Gln Cys Lys His Ser Met Lys Tyr Arg Leu Ser Phe Cys
            20                  25                  30

Arg Lys Thr Cys Gly Thr Cys
        35

<210> SEQ ID NO 222
<211> LENGTH: 37
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: Para-phosphono-Phenylalanine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (23)..(23)
<223> OTHER INFORMATION: Nle
<220> FEATURE:
<221> NAME/KEY: MOD_RES
<222> LOCATION: (37)..(37)
<223> OTHER INFORMATION: AMIDATION

<400> SEQUENCE: 222

Xaa Xaa Arg Ser Cys Ile Asp Thr Ile Pro Lys Ser Arg Cys Thr Ala
1               5                   10                  15

Phe Lys Cys Lys His Ser Xaa Lys Tyr Arg Leu Ser Phe Cys Arg Lys
            20                  25                  30

Thr Cys Gly Thr Cys
        35

<210> SEQ ID NO 223
<211> LENGTH: 37
```

```
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (1)..(1)
<223> OTHER INFORMATION: Para-phosphono-Phenylalanine
<220> FEATURE:
<221> NAME/KEY: MISC_FEATURE
<222> LOCATION: (2)..(2)
<223> OTHER INFORMATION: Aminoethyloxyethyloxyacetic acid
<220> FEATURE:
<221> NAME/KEY: MOD_RES
<222> LOCATION: (37)..(37)
<223> OTHER INFORMATION: AMIDATION

<400> SEQUENCE: 223

Xaa Xaa Arg Ser Cys Ile Asp Thr Ile Pro Lys Ser Arg Cys Thr Ala
1               5                   10                  15

Phe Gln Cys Lys His Ser Met Lys Tyr Arg Leu Ser Phe Cys Arg Lys
                20                  25                  30

Thr Cys Gly Thr Cys
        35

<210> SEQ ID NO 224
<211> LENGTH: 35
<212> TYPE: PRT
<213> ORGANISM: Artificial Sequence
<220> FEATURE:
<223> OTHER INFORMATION: ShK-Based Peptide
<220> FEATURE:
<221> NAME/KEY: MOD_RES
<222> LOCATION: (21)..(21)
<223> OTHER INFORMATION: Nle
<220> FEATURE:
<221> NAME/KEY: MISC_FEATURE
<222> LOCATION: (22)..(22)
<223> OTHER INFORMATION: Diaminopropionic acid

<400> SEQUENCE: 224

Arg Ser Cys Ile Asp Thr Ile Pro Lys Ser Arg Cys Thr Ala Phe Gln
1               5                   10                  15

Cys Lys His Ser Xaa Xaa Tyr Arg Leu Ser Phe Cys Arg Lys Thr Cys
                20                  25                  30

Gly Thr Cys
        35

<210> SEQ ID NO 225
<211> LENGTH: 35
<212> TYPE: PRT
<213> ORGANISM: Pandinus imperator

<400> SEQUENCE: 225

Leu Val Lys Cys Arg Gly Thr Ser Asp Cys Gly Arg Pro Cys Gln Gln
1               5                   10                  15

Gln Thr Gly Cys Pro Asn Ser Lys Cys Ile Asn Arg Met Cys Lys Cys
                20                  25                  30

Tyr Gly Cys
        35

<210> SEQ ID NO 226
<211> LENGTH: 35
<212> TYPE: PRT
<213> ORGANISM: Pandinus imperator

<400> SEQUENCE: 226
```

-continued

```
Thr Ile Ser Cys Thr Asn Pro Lys Gln Cys Tyr Pro His Cys Lys Lys
1               5                   10                  15
Glu Thr Gly Tyr Pro Asn Ala Lys Cys Met Asn Arg Lys Cys Lys Cys
            20                  25                  30
Phe Gly Arg
        35

<210> SEQ ID NO 227
<211> LENGTH: 35
<212> TYPE: PRT
<213> ORGANISM: Pandinus imperator

<400> SEQUENCE: 227

Thr Ile Ser Cys Thr Asn Glu Lys Gln Cys Tyr Pro His Cys Lys Lys
1               5                   10                  15
Glu Thr Gly Tyr Pro Asn Ala Lys Cys Met Asn Arg Lys Cys Lys Cys
            20                  25                  30
Phe Gly Arg
        35

<210> SEQ ID NO 228
<211> LENGTH: 38
<212> TYPE: PRT
<213> ORGANISM: Pandinus imperator

<400> SEQUENCE: 228

Ile Glu Ala Ile Arg Cys Gly Gly Ser Arg Asp Cys Tyr Arg Pro Cys
1               5                   10                  15
Gln Lys Arg Thr Gly Cys Pro Asn Ala Lys Cys Ile Asn Lys Thr Cys
            20                  25                  30
Lys Cys Tyr Gly Cys Ser
        35

<210> SEQ ID NO 229
<211> LENGTH: 34
<212> TYPE: PRT
<213> ORGANISM: Heterometrus spinifer

<400> SEQUENCE: 229

Ala Ser Cys Arg Thr Pro Lys Asp Cys Ala Asp Pro Cys Arg Lys Glu
1               5                   10                  15
Thr Gly Cys Pro Tyr Gly Lys Cys Met Asn Arg Lys Cys Lys Cys Asn
            20                  25                  30
Arg Cys

<210> SEQ ID NO 230
<211> LENGTH: 38
<212> TYPE: PRT
<213> ORGANISM: Leiurus quinquestriatus hebraeus

<400> SEQUENCE: 230

Gly Val Pro Ile Asn Val Ser Cys Thr Gly Ser Pro Gln Cys Ile Lys
1               5                   10                  15
Pro Cys Lys Asp Ala Gly Met Arg Phe Gly Lys Cys Met Asn Arg Lys
            20                  25                  30
Cys His Cys Thr Pro Lys
        35

<210> SEQ ID NO 231
```

```
<211> LENGTH: 38
<212> TYPE: PRT
<213> ORGANISM: Leiurus quinquestriatus hebraeus

<400> SEQUENCE: 231

Gly Val Pro Ile Asn Val Lys Cys Thr Gly Ser Pro Gln Cys Leu Lys
1               5                   10                  15

Pro Cys Lys Asp Ala Gly Met Arg Phe Gly Lys Cys Ile Asn Gly Lys
            20                  25                  30

Cys His Cys Thr Pro Lys
            35

<210> SEQ ID NO 232
<211> LENGTH: 38
<212> TYPE: PRT
<213> ORGANISM: Orthochirus scrobiculosus

<400> SEQUENCE: 232

Gly Val Ile Ile Asn Val Lys Cys Lys Ile Ser Arg Gln Cys Leu Glu
1               5                   10                  15

Pro Cys Lys Lys Ala Gly Met Arg Phe Gly Lys Cys Met Asn Gly Lys
            20                  25                  30

Cys His Cys Thr Pro Lys
            35

<210> SEQ ID NO 233
<211> LENGTH: 35
<212> TYPE: PRT
<213> ORGANISM: Anuroctonus phaiodactylus

<400> SEQUENCE: 233

Glx Lys Glu Cys Thr Gly Pro Gln His Cys Thr Asn Phe Cys Arg Lys
1               5                   10                  15

Asn Lys Cys Thr His Gly Lys Cys Met Asn Arg Lys Cys Lys Cys Phe
            20                  25                  30

Asn Cys Lys
        35

<210> SEQ ID NO 234
<211> LENGTH: 39
<212> TYPE: PRT
<213> ORGANISM: Centruroides noxius

<400> SEQUENCE: 234

Thr Ile Ile Asn Val Lys Cys Thr Ser Pro Lys Gln Cys Ser Lys Pro
1               5                   10                  15

Cys Lys Glu Leu Tyr Gly Ser Ser Ala Gly Ala Lys Cys Met Asn Gly
            20                  25                  30

Lys Cys Lys Cys Tyr Asn Asn
            35

<210> SEQ ID NO 235
<211> LENGTH: 39
<212> TYPE: PRT
<213> ORGANISM: Centruroides limbatus

<400> SEQUENCE: 235

Thr Val Ile Asp Val Lys Cys Thr Ser Pro Lys Gln Cys Leu Pro Pro
1               5                   10                  15

Cys Lys Ala Gln Phe Gly Leu Arg Ala Gly Ala Lys Cys Met Asn Gly
            20                  25                  30
```

```
Lys Cys Lys Cys Tyr Pro His
        35

<210> SEQ ID NO 236
<211> LENGTH: 37
<212> TYPE: PRT
<213> ORGANISM: Leiurus quinquestriatus hebraeus

<400> SEQUENCE: 236

Gln Phe Thr Asn Val Ser Cys Thr Thr Ser Lys Glu Cys Trp Ser Val
1               5                   10                  15

Cys Gln Arg Leu His Asn Thr Ser Arg Gly Lys Cys Met Asn Lys Lys
            20                  25                  30

Cys Arg Cys Tyr Ser
        35

<210> SEQ ID NO 237
<211> LENGTH: 37
<212> TYPE: PRT
<213> ORGANISM: Tityus serrulatus

<400> SEQUENCE: 237

Val Phe Ile Asn Ala Lys Cys Arg Gly Ser Pro Glu Cys Leu Pro Lys
1               5                   10                  15

Cys Lys Glu Ala Ile Gly Lys Ala Ala Gly Lys Cys Met Asn Gly Lys
            20                  25                  30

Cys Lys Cys Tyr Pro
        35

<210> SEQ ID NO 238
<211> LENGTH: 37
<212> TYPE: PRT
<213> ORGANISM: Bunodosoma granuliferum

<400> SEQUENCE: 238

Val Cys Arg Asp Trp Phe Lys Glu Thr Ala Cys Arg His Ala Lys Ser
1               5                   10                  15

Leu Gly Asn Cys Arg Thr Ser Gln Lys Tyr Arg Ala Asn Cys Ala Lys
            20                  25                  30

Thr Cys Glu Leu Cys
        35

<210> SEQ ID NO 239
<211> LENGTH: 38
<212> TYPE: PRT
<213> ORGANISM: Mesobuthus martensii

<400> SEQUENCE: 239

Val Gly Ile Asn Val Lys Cys Lys His Ser Gly Gln Cys Leu Lys Pro
1               5                   10                  15

Cys Lys Asp Ala Gly Met Arg Phe Gly Lys Cys Ile Asn Gly Lys Cys
            20                  25                  30

Asp Cys Thr Pro Lys Gly
        35

<210> SEQ ID NO 240
<211> LENGTH: 37
<212> TYPE: PRT
<213> ORGANISM: Mesobuthus martensii

<400> SEQUENCE: 240
```

```
Gln Phe Thr Asp Val Lys Cys Thr Gly Ser Lys Gln Cys Trp Pro Val
1               5                   10                  15

Cys Lys Gln Met Phe Gly Lys Pro Asn Gly Lys Cys Met Asn Gly Lys
                20                  25                  30

Cys Arg Cys Tyr Ser
                35
```

<210> SEQ ID NO 241
<211> LENGTH: 37
<212> TYPE: PRT
<213> ORGANISM: Tityus cambridgei

<400> SEQUENCE: 241

```
Val Phe Ile Asn Val Lys Cys Arg Gly Ser Lys Glu Cys Leu Pro Ala
1               5                   10                  15

Cys Lys Ala Ala Val Gly Lys Ala Ala Gly Lys Cys Met Asn Gly Lys
                20                  25                  30

Cys Lys Cys Tyr Pro
                35
```

<210> SEQ ID NO 242
<211> LENGTH: 35
<212> TYPE: PRT
<213> ORGANISM: Tityus cambridgei

<400> SEQUENCE: 242

```
Thr Gly Pro Gln Thr Thr Cys Gln Ala Ala Met Cys Glu Ala Gly Cys
1               5                   10                  15

Lys Gly Leu Gly Lys Ser Met Glu Ser Cys Gln Gly Asp Thr Cys Lys
                20                  25                  30

Cys Lys Ala
        35
```

<210> SEQ ID NO 243
<211> LENGTH: 36
<212> TYPE: PRT
<213> ORGANISM: Vaejovis mexicanus smithi
<220> FEATURE:
<221> NAME/KEY: MOD_RES
<222> LOCATION: (36)..(36)
<223> OTHER INFORMATION: AMIDATION

<400> SEQUENCE: 243

```
Ala Ala Ala Ile Ser Cys Val Gly Ser Pro Glu Cys Pro Pro Lys Cys
1               5                   10                  15

Arg Ala Gln Gly Cys Lys Asn Gly Lys Cys Met Asn Arg Lys Cys Lys
                20                  25                  30

Cys Tyr Tyr Cys
            35
```

<210> SEQ ID NO 244
<211> LENGTH: 35
<212> TYPE: PRT
<213> ORGANISM: Heteractis magnifica

<400> SEQUENCE: 244

```
Arg Thr Cys Lys Asp Leu Ile Pro Val Ser Glu Cys Thr Asp Ile Arg
1               5                   10                  15

Cys Arg Thr Ser Met Lys Tyr Arg Leu Asn Leu Cys Arg Lys Thr Cys
                20                  25                  30
```

```
Gly Ser Cys
        35

<210> SEQ ID NO 245
<211> LENGTH: 36
<212> TYPE: PRT
<213> ORGANISM: Actinia equina

<400> SEQUENCE: 245

Gly Cys Lys Asp Asn Phe Ser Ala Asn Thr Cys Lys His Val Lys Ala
1               5                   10                  15

Asn Asn Asn Cys Gly Ser Gln Lys Tyr Ala Thr Asn Cys Ala Lys Thr
            20                  25                  30

Cys Gly Lys Cys
        35

<210> SEQ ID NO 246
<211> LENGTH: 36
<212> TYPE: PRT
<213> ORGANISM: Anemonia sulcata

<400> SEQUENCE: 246

Ala Cys Lys Asp Asn Phe Ala Ala Ala Thr Cys Lys His Val Lys Glu
1               5                   10                  15

Asn Lys Asn Cys Gly Ser Gln Lys Tyr Ala Thr Asn Cys Ala Lys Thr
            20                  25                  30

Cys Gly Lys Cys
        35

<210> SEQ ID NO 247
<211> LENGTH: 39
<212> TYPE: PRT
<213> ORGANISM: Centruroides margaritatus

<400> SEQUENCE: 247

Thr Ile Ile Asn Val Lys Cys Thr Ser Pro Lys Gln Cys Leu Pro Pro
1               5                   10                  15

Cys Lys Ala Gln Phe Gly Gln Ser Ala Gly Ala Lys Cys Met Asn Gly
            20                  25                  30

Lys Cys Lys Cys Tyr Pro His
        35

<210> SEQ ID NO 248
<211> LENGTH: 38
<212> TYPE: PRT
<213> ORGANISM: Androctonus mauritanicus mauritanicus

<400> SEQUENCE: 248

Gly Val Glu Ile Asn Val Lys Cys Ser Gly Ser Pro Gln Cys Leu Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 249
<211> LENGTH: 37
<212> TYPE: PRT
<213> ORGANISM: Androctonus australis

<400> SEQUENCE: 249
```

Val Arg Ile Pro Val Ser Cys Lys His Ser Gly Gln Cys Leu Lys Pro
1               5                   10                  15

Cys Lys Asp Ala Gly Met Arg Phe Gly Lys Cys Met Asn Gly Lys Cys
            20                  25                  30

Asp Cys Thr Pro Lys
        35

<210> SEQ ID NO 250
<211> LENGTH: 34
<212> TYPE: PRT
<213> ORGANISM: Scorpio maurus palmatus

<400> SEQUENCE: 250

Val Ser Cys Thr Gly Ser Lys Asp Cys Tyr Ala Pro Cys Arg Lys Gln
1               5                   10                  15

Thr Gly Cys Pro Asn Ala Lys Cys Ile Asn Lys Ser Cys Lys Cys Tyr
            20                  25                  30

Gly Cys

<210> SEQ ID NO 251
<211> LENGTH: 36
<212> TYPE: PRT
<213> ORGANISM: Mesobuthus tamulus

<400> SEQUENCE: 251

Gln Phe Thr Asp Val Asp Cys Ser Val Ser Lys Glu Cys Trp Ser Val
1               5                   10                  15

Cys Lys Asp Leu Phe Gly Val Asp Arg Gly Lys Cys Met Gly Lys Lys
            20                  25                  30

Cys Arg Cys Tyr
        35

<210> SEQ ID NO 252
<211> LENGTH: 38
<212> TYPE: PRT
<213> ORGANISM: Odontobuthus doriae

<400> SEQUENCE: 252

Gly Val Pro Thr Asp Val Lys Cys Arg Gly Ser Pro Gln Cys Ile Gln
1               5                   10                  15

Pro Cys Lys Asp Ala Gly Met Arg Phe Gly Lys Cys Met Asn Gly Lys
            20                  25                  30

Cys His Cys Thr Pro Lys
        35

<210> SEQ ID NO 253
<211> LENGTH: 38
<212> TYPE: PRT
<213> ORGANISM: Mesobuthus tamulus sindicus

<400> SEQUENCE: 253

Gly Val Pro Ile Asn Val Lys Cys Arg Gly Ser Pro Gln Cys Ile Gln
1               5                   10                  15

Pro Cys Arg Asp Ala Gly Met Arg Phe Gly Lys Cys Met Asn Gly Lys
            20                  25                  30

Cys His Cys Thr Pro Gln
        35

<210> SEQ ID NO 254
<211> LENGTH: 37

```
<212> TYPE: PRT
<213> ORGANISM: Buthus occitanus israelis

<400> SEQUENCE: 254

Gly Val Pro Ile Asn Val Lys Cys Arg Gly Ser Arg Asp Cys Leu Asp
1               5                   10                  15

Pro Cys Lys Lys Ala Gly Met Arg Phe Gly Lys Cys Ile Asn Ser Lys
            20                  25                  30

Cys His Cys Thr Pro
        35

<210> SEQ ID NO 255
<211> LENGTH: 38
<212> TYPE: PRT
<213> ORGANISM: Leiurus quinquestriatus hebraeus

<400> SEQUENCE: 255

Gly Val Pro Ile Asn Val Pro Cys Thr Gly Ser Pro Gln Cys Ile Lys
1               5                   10                  15

Pro Cys Lys Asp Ala Gly Met Arg Phe Gly Lys Cys Met Asn Arg Lys
            20                  25                  30

Cys His Cys Thr Pro Lys
        35

<210> SEQ ID NO 256
<211> LENGTH: 37
<212> TYPE: PRT
<213> ORGANISM: Buthus occitanus tunetanus

<400> SEQUENCE: 256

Val Gly Ile Pro Val Ser Cys Lys His Ser Gly Gln Cys Ile Lys Pro
1               5                   10                  15

Cys Lys Asp Ala Gly Met Arg Phe Gly Lys Cys Met Asn Arg Lys Cys
            20                  25                  30

Asp Cys Thr Pro Lys
        35
```

OPHTHALMIC USES OF TOXIN-BASED THERAPEUTIC PEPTIDES AND PHARMACEUTICAL COMPOSITIONS THEREOF

CROSS REFERENCE TO RELATED APPLICATION

This application claims priority to U.S. Provisional Patent Application Ser. No. 61/857,157, filed on Jul. 22, 2013, which is incorporated by reference herein in its entirety.

FIELD OF THE DISCLOSURE

The methods disclosed herein relate to the use of toxin-based therapeutic peptides to treat ophthalmic conditions including dry eye and uveitis, among other uses. The toxin-based therapeutic peptides can include ShK-based peptides. Pharmaceutical compositions including the toxin-based therapeutic peptides are also disclosed.

BACKGROUND OF THE DISCLOSURE

Tear secretion by the eye protects and maintains the integrity of ocular surface tissues including the cornea, corneal limbus, conjunctiva, blood vessels, and eyelids. Tear secretion is crucial to protecting the eye from infectious agents and environmental damage. The liquid film formed by tears is also essential to providing a smooth optical surface and to maintaining cellular health.

One of the most common ophthalmic conditions is dry eye syndrome (also known as keratoconjunctivitis sicca and "dry eye"). Dry eye is defined by a deficiency or lack of tears which can lead to inflammation and damage to the eye.

Dry eye can have numerous causes. For example, a temporary form of dry eye can be triggered by an inflammatory reaction to eye trauma or infection. In some, temporary dry eye can become chronic, for example, when a local ocular autoimmune condition develops.

Dry eye can also be caused by systemic conditions. For example, Sjogren's syndrome is an autoimmune disorder identified by its two most common symptoms, dry eyes and a dry mouth. Sjogren's syndrome results in immune system damage to the mucous membranes and moisture-secreting glands of the eyes and mouth. The cell and tissue damage results in decreased production of tears and saliva. Sjogren's syndrome often accompanies other immune system disorders, such as rheumatoid arthritis and lupus erythematosus.

Current treatments for dry eye caused by Sjogren's syndrome include pharmaceuticals such as Pilocarpine, cyclosporine or Cevimeline, both of which primarily increase saliva production when used orally. Pilocarpine can be administered as eye drops, but constriction of the pupil and the risk of epileptic-type effects have to be considered.

Sjogren's syndrome is just one example of a condition that leads to dry eye that lacks an effective treatment without unacceptable side effects. As another example, uveitis, inflammation of the uvea, is responsible for about 10% of visual impairment in the United States. The uveal tract includes the iris, ciliary body, and choroid. Uveitis is most commonly classified anatomically as anterior, intermediate, posterior, or diffuse. Anterior uveitis is localized primarily to the anterior segment of the eye and includes iritis and iridocyclitis. Intermediate uveitis, also called peripheral uveitis, is centered in the area immediately behind the iris and lens in the region of the ciliary body and pars plana, hence the alternate terms "cyclitis" and "pars planitis" are also used. Posterior uveitis signifies a number of forms of uveitis including retinitis, choroiditis, and optic neuritis. Diffuse uveitis implies inflammation involving all parts of the eye, including anterior, intermediate, and posterior structures. Current treatments for uveitis include principally locally applied and/or systemic steroid therapy.

Approximately 6% of uveitis cases in the United States occur in children, while 2.2-33.1% of uveitis cases in international populations occur in children and adolescents. One of the major causes of pediatric uveitis is associated with autoimmune disorders including: juvenile idiopathic arthritis, reactive arthritis, ankylosing spondylitis, ulcerative colitis, Crohns disease, childhood sarcoidosis, and Kawasaki disease. Pediatric uveitis is a major health concern in children, as complications include band keratopathy, glaucoma, phthisis, cataract formation, macular edema, and optic nerve degeneration. Chronic uveitis can result in morbidity and vision loss.

SUMMARY OF THE DISCLOSURE

The present disclosure provides methods of treating ophthalmic conditions including dry eye, uveitis, scleritis, and other inflammatory conditions of the eye. The disclosure further provides methods for treating the ocular manifestations of systemic autoimmune disease such as episcleritis, keratitis, retinal vasculitis, or other diseases that involve inflammation of the cornea, retina, sclera, and/or orbit. The methods treat ophthalmic conditions by administering a therapeutically effective amount of a pharmaceutical composition that includes a toxin-based therapeutic peptide. Methods of identifying subjects who will benefit from the described treatments are also provided.

BRIEF DESCRIPTION OF THE FIGURES

FIG. 3A shows that topically administered ShK-186 was found in significant concentrations in the anterior chamber aqueous fluid of the treated right eye (RE), but not in the left eye (LE) or plasma (P), indicating intraocular delivery of the drug. FIG. 3B shows that there was no detectable ShK-186 in samples from the untreated left eye (LE) but significant amounts of drug in the treated right eye (RE). Samples were collected after 21 days of dosing. FIG. 3C shows that topical administration of 0.1% ShK-186 or 1% ShK-186 for 7 days resulted in concentration-dependent increases in drug concentration in the anterior chamber of the eye. Systemic exposure was below the level of detection (not shown). 1-1 to 1-4: saline vehicle treated; 3-1 to 3-3: ShK-186 0.1% solution in P6N; 4-1 to 4-4: ShK-186 1% solution in P6N. Anterior chamber aqueous fluid was recovered on day 19 with a 29 gauge needle, diluted and analyzed by Standard ELISA methods. FIG. 3D shows that topical administration of 0.1% ShK-198 or 1% ShK-198 thrice daily for 7 days resulted in concentration-dependent increases in drug concentration in the eye. Systemic exposure was below the level of detection (not shown). 2-1 to 2-4: P6N vehicle treated; 5-1 to 5-4: ShK-198 0.1% solution in P6N; 6-1 to 6-4: ShK-198 1% solution in P6N. Aqueous fluid was recovered on day 19 with a 29 gauge needle, diluted and analyzed by Standard ELISA methods.

FIG. 4A: ShK-186 topical administration reduces clinical score in a rat model of experimental autoimmune anterior uveitis (EAAU). Clinical observations were made of each animal using a slit lamp on days 11, 13, 15, and 18 post induction of EAAU by immunization with an adjuvanted melanin associated antigen (MAA) emulsion. Eyes were given individual scores based on pupil function (miosis), iris structure, presence of cells in the anterior chamber, and presence of protein in the anterior chamber (flare). Scores were then converted into a composite clinical score for each day. Composite scores of animals treated three times daily with 0.1% from day 0-8 and with 1% ShK-186 from day 9-18 topically to the eye were found to be significantly lower than those treated with vehicle. N=8 rats/16 eyes. FIG. 4B: ShK-186 topical administration reduced gross pathology in a rat model of experimental autoimmune uveitis. Left Panel: Animal was dosed three times daily with vehicle (P6N). On day 18 post immunization, animal 3-2 is observed to have a composite clinical score of 13: a miotic pupil completely full of protein (score=4), engorged iris blood vessels with some damage (score=3), many infiltrating cells in the anterior chamber (score=4; not pictured), and slight flare (score=2; not pictured). Right Panel: Animal received 0.1% ShK186 from day 0 to and including day 8 and 1% ShK-186 starting on day 9 till and including day 18 after immunization for induction of EAAU. On day 18 post immunization animal 4-8 is observed to have a composite clinical score of 0: normal pupil (score=0), normal iris vessels and structure (score=0), no visible cells or protein in the anterior chamber (scores=0 for each respectively; not pictured). FIG. 4C: ShK-186 topical administration reduces histopathology in EAAU. Eyes collected into 10% formalin on day 19 post immunization with adjuvanted MAA were sectioned and stained with hematoxylin and eosin. Eye sections were observed and scored for iris and ciliary body structure and the degree of inflammatory cell infiltration to the stroma of the iris and/or ciliary body and anterior chamber (based on parameters outlined in Kim et al., Korean J. Ophthalmol. 12, 14-18, (1998)) by an independent veterinary pathologist. (1.) Control healthy eye (10×); (2.) & (4.) Eye from an animal treated with vehicle was given a histopathology score of 2 (10×, 40×); (3.) & (5.) Eye from an animal treated three times daily with 0.1% ShK-186 for 9 days followed by 1% ShK-186 for 10 days was given a histopathology score of 0 (10×, 40×). (6.) Composite clinical score based on histopathology analysis of four eyes from a vehicle treated group (P6N) or ShK-186-treated group as indicated above (1% ShK-186). FIG. 4D: ShK-198 topical administration reduces clinical score in a rat model of EAAU. Clinical observations were made of each animal using a slit lamp on days 13 post induction of EAAU by immunization with an adjuvanted MAA emulsion. Eyes were given individual scores based on presence of cells in the anterior chamber (Top Panel), and presence of protein in the anterior chamber or flare (Bottom Panel). Rats were treated three times daily with P6N vehicle or 1% ShK-198 topically to the eye. N=10 rats/20 eyes.

DETAILED DESCRIPTION

Figure 1:
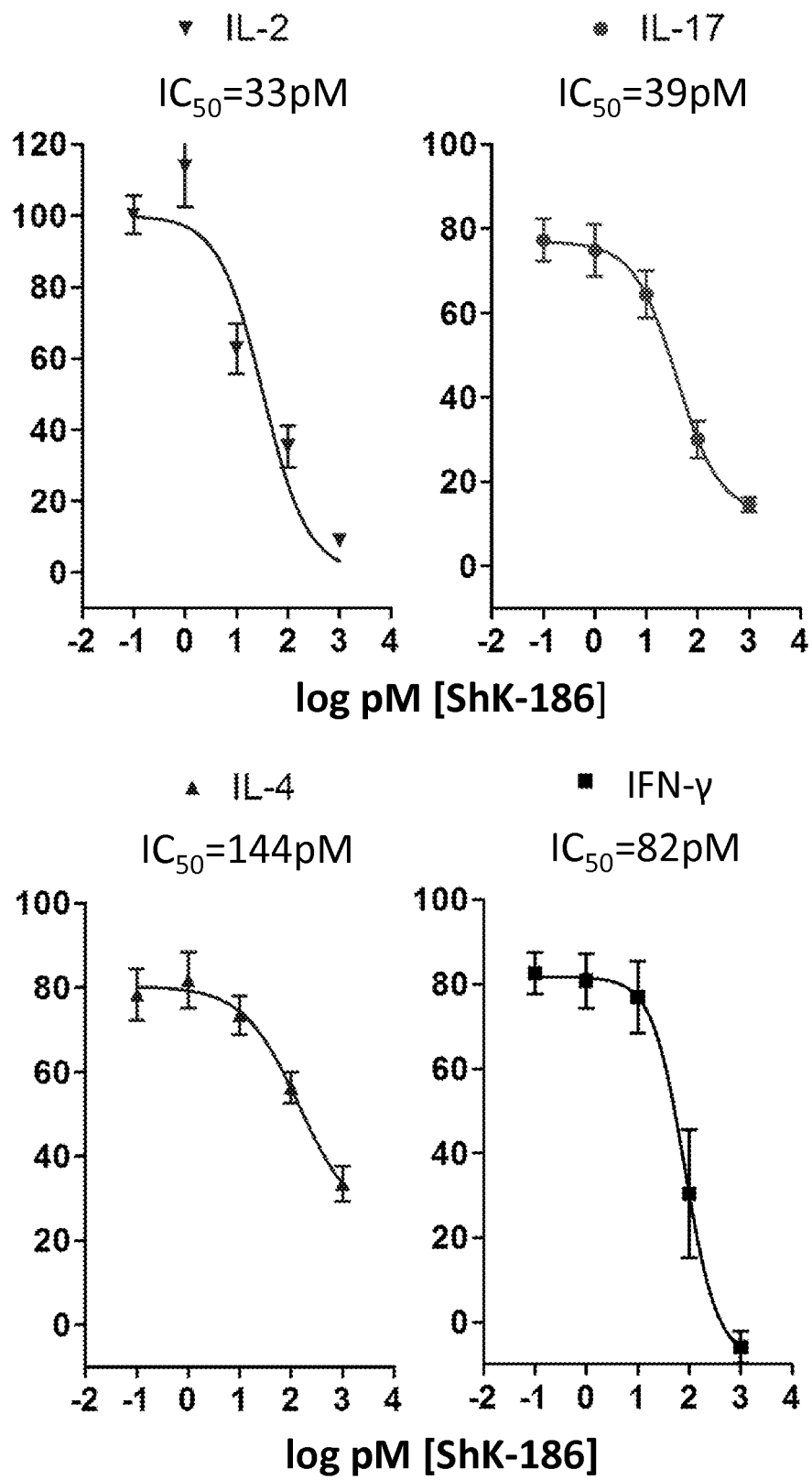
FIG. 1 provides a series of four graphs showing the effect of ShK-186 on inflammatory cytokine levels in human whole blood stimulated with thapsigargin. ShK-186 suppressed the inflammatory cytokines Interleukin (IL)-2, IL-17, IL-4, and Interferon (IFN)-γ in a dose-dependent manner.

Tear secretion is regulated by a complex system with tight neural connections, as evidenced by the rapid tear-secreting reaction to physical, environmental, microbial, and emotional stimuli. The tear-secreting tissues include the lacrimal glands, meibomian glands, conjunctival goblet cells, and epithelial cells. Disruption of the tear-forming system, in whole or in part, can lead to insufficient tear production, a condition known as dry eye.

Dry eye can be caused by localized or systemic conditions. For example, dry eye as a localized condition can result from stress to the ocular surface. This ocular stress can be caused by infection and/or disrupted regulation of inflammatory factors, such as cytokines and chemokines. Such a condition may be temporary. In other instances, however, during ocular surface disruption, antigen presenting cells (APC) can become activated and internalize auto-antigens, which are processed and presented, thereby promoting an autoimmune reaction. The resulting tissue damage can create a sustained autoimmune reaction with resulting destruction of ocular tissues including the cornea, goblet cells, and epithelial cells. This destruction can ultimately lead to sustained dry eye and other manifestations of inflammatory ocular disease.

Dry eye can also result from systemic autoimmune diseases, including Sjogren's syndrome, ocular cicatricial pemphigoid, and Stevens-Johnson syndrome. Systemic autoimmunity resulting in dry eye can also result from the allograft in stem cell transplantation, manifesting as graft versus host disease.

Localized and systemic autoimmune reactions leading to dry eye have the activation of autoreactive T- and/or B-cells in common. In dry eye generally and Sjogren's syndrome more particularly, the activation, differentiation, and homing of autoreactive T-cells to ocular surface tissues is associated with an increase in cytokines including Interferon (IFN)-γ and Interleukin (IL)-17. IFN-γ alters the mucins on corneal epithelial cells leading to tissue damage and reduced goblet cell density.

Experiments with mouse models of dry eye further support the role of T-cells in development and pathology of the condition. Stern, et al. (Int. Rev. Immunol. 32:19-41, 2013) induced dry eye in mice by exposure to conditions causing desiccating stress. Several days later the mice exhibited T-cell infiltration and increased cytokine levels (IFN-γ, IL-1β, Tumor necrosis factor (TNF)-α, and IL-17). The ocular surface exhibited apoptosis and cell death, and tear production was reduced.

CD4+ T-cells from the lymph nodes and spleen of these dry eye mice (donor mice) were removed and injected into T-cell-deficient mice (recipient mice). The recipient mice developed dry eye conditions similar to those of the donor mice, including homing of T-cells to ocular surface tissues, increased cytokine levels, decreased Goblet cell density, decreased tear production and decreased tear turnover. Stern et al. concluded that the CD4+ T-cells from the donor mice were sufficient to induce dry eye in the recipient mice. This conclusion is consistent with observations of activated CD4+ T-cells localized in the ocular surface tissues of dry eye patients.

Inflammatory eye diseases or conditions associated with T-cell infiltration and activation include acanthamoeba infection, acute retinal pigment epitheliitis, allergies, arthritis, bacterial infection, Behcet's disease, Behcet's-related retinitis, blepharitis, chemical exposure, choroiditis, chorioretinital inflammation, Crohn's disease, conjunctivitis, diabetic retinopathy, dry eye, episcleritis, eye bruises, eye trauma, food allergies, foreign body exposure, fungal infection, hives, iridocyclitis, iritis, juvenile idiopathic arthritis, keratitis, lupus, mycobacterial infection, neuroretinitis, parasite infection, post-surgical conditions, posterior cyclitis, retinal vasculitis, retinitis, rheumatoid arthritis, sarcoidosis, sarcoidosis-related retinitis, seasonal allergies, scleritis, spirochete infection, toxin exposure, ulcerative colitis, uveitis, and viral infection.

Many immune-related diseases and metabolic disorders, including T-cell mediated ophthalmic conditions, are attributed at least in part to the action of memory T-cells. Two categories of memory T-cells are known: central memory T-cells ($T_{CM}$) and effector memory T-cells ($T_{EM}$).

Expanded populations of $T_{EM}$ are commonly observed in patients with immune-related disorders, and in some cases this is a result of a disorder affecting regulatory T-cells (Treg). Treg are a type of T-cells that suppress immune responses of other cells, including $T_{EM}$. In the absence of normal levels of Treg, the body's immune responses become uncontrolled and attack healthy tissues and organs. This disruption of Treg function leads to a variety of autoimmune disorders including ophthalmic diseases.

Upon activation, $T_{EM}$ up-regulate their expression of Kv1.3 K+ ion channels. The $T_{EM}$ that initiate and contribute to damaging autoimmune processes are highly dependent upon these Kv1.3 channels to sustain intracellular calcium levels required for activation, proliferation, and cytokine production. Therefore, the proliferation of $T_{EM}$ is sensitive to Kv1.3 K+ channel blockers. Wulff et al., J. Clin. Invest., 111, 1703-1713 (2003). Other cell types that express the Kv1.3 channel and that are important for inflammation include macrophages, dendritic cells, class-switched memory B-cells, and microglial cells.

Without being bound by theory, it is believed that the toxin-based therapeutic peptides disclosed herein effectively treat dry eye and other inflammatory ophthalmic conditions, including those associated with up-regulated $T_{EM}$, by blocking Kv1.3 K+ channels. Accordingly, the present disclosure provides methods of using toxin-based therapeutic peptides for treating immune-mediated ophthalmic conditions, such as dry eye and uveitis. The toxin-based therapeutic peptides provide a new treatment option for immune-mediated ophthalmic conditions that could reduce autoimmune-related ocular damage and dry eye, with a more favorable safety profile than existing therapies.

Toxin-Based Therapeutic Peptides

Particular examples of toxin-based therapeutic peptides for use in the methods disclosed herein bind voltage gated channels. Exemplary voltage gated channels include Kv1.1, Kv1.2, Kv1.3, Kv1.4, Kv1.5, Kv1.6, Kv1.7, Kv2.1, Kv3.1, Kv3.2, Kv11.1, Kc1.1, Kc2.1, Kc3.1, Nav1.2, Nav1.4, and Cav1.2.

Toxin peptides are produced by a variety of organisms and have evolved to bind to ion channels and receptors. Native toxin peptides from snakes, scorpions, spiders, bees, snails, and sea anemone are typically 10-80 amino acids in length and contain 2 to 5 disulfide bridges that create compact molecular structures. These peptides appear to have evolved from a small number of structural frameworks. The peptides cluster into families of folding patterns that are conserved through cysteine/disulfide loop structures to maintain a three dimensional structure that contributes to potency, stability, and selectivity (Pennington, et al., Biochemistry, 38, 14549-14558 (1999); Tudor, et al., Eur. J. Biochem., 251, 133-141 (1998); and Jaravine et al., Biochemistry, 36, 1223-1232, (1997)).

As used herein, "toxin-based therapeutic peptides" include a toxin-based peptide of Table 1 (or a variant, D-substituted analog, carboxy-terminal amide, modification, derivative or pharmaceutically acceptable salt thereof) or an Shk-based peptide of Table 2 (or a variant, D-substituted analog, carboxy-terminal amide, modification, derivative or pharmaceutically acceptable salt thereof). Toxin-based therapeutic peptides can be synthetic or naturally-occurring.

"Toxin-based peptides" include any synthetic or naturally-known toxin peptide and those peptides disclosed in Table 1 as well as variants, D-substituted analogs, carboxy-terminal amides, modifications, derivatives and pharmaceutically acceptable salts thereof. Particular exemplary toxin-based therapeutic peptides for use in the methods disclosed herein include the toxin-based peptides listed in Table 1, and as shown in the sequence listing as SEQ ID NO: 225-256. In various embodiments, a method of treating ophthalmic conditions includes administering a toxin-based therapeutic peptide including a toxin-based peptide of Table 1 (SEQ ID NO: 225-256). In various embodiments, the toxin-based peptides of Table 1 (SEQ ID NO: 225-256) can be used in the production of a pharmaceutical composition (or medicament) to treat ophthalmic conditions.

TABLE 1

Exemplary Toxin-Based Peptides

| Sequence/structure | Shorthand designation | SEQ ID NO: |
|---|---|---|
| LVKCRGTSDCGRPCQQQTGCPNSKCINRMCKCYGC | Pi1 | 225 |
| TISCTNPKQCYPHCKKETGYPNAKCMNRKCKCFGR | Pi2 | 226 |
| TISCTNEKQCYPHCKKETGYPNAKCMNRKCKCFGR | Pi3 | 227 |
| IEAIRCGGSRDCYRPCQKRTGCPNAKCINKTCKCYGCS | Pi4 | 228 |
| ASCRTPKDCADPCRKETGCPYGKCMNRKCKCNRC | HsTx1 | 229 |
| GVPINVSCTGSPQCIKPCKDAGMRFGKCMNRKCHCTPK | AgTx2 | 230 |
| GVPINVKCTGSPQCLKPCKDAGMRFGKCINGKCHCTPK | AgTx1 | 231 |
| GVIINVKCKISRQCLEPCKKAGMRFGKCMNGKCHCTPK | OSK1 | 232 |
| ZKECTGPQHCTNFCRKNKCTHGKCMNRKCKCFNCK | Anuroctoxin | 232 |
| TIINVKCTSPKQCSKPCKELYGSSAGAKCMNGKCKCYNN | NTx | 234 |
| TVIDVKCTSPKQCLPPCKAQFGIRAGAKCMNGKCKCYPH | HgTx1 | 235 |
| QFTNVSCTTSKECWSVCQRLHNTSRGKCMNKKCRCYS | ChTx | 236 |
| VFINAKCRGSPECLPKCKEAIGKAAGKCMNGKCKCYP | Titystoxin-Ka | 237 |
| VCRDWFKETACRHAKSLGNCRTSQKYRANCAKTCELC | BgK | 238 |
| VGINVKCKHSGQCLKPCKDAGMRFGKCINGKCDCTPKG | BmKTx | 239 |
| QFTDVKCTGSKQCWPVCKQMFGKPNGKCMNGKCRCYS | BmTx1 | 240 |
| VFINVKCRGSKECLPACKAAVGKAAGKCMNGKCKCYP | Tc30 | 241 |
| TGPQTTCQAAMCEAGCKGLGKSMESCQGDTCKCKA | Tc32 | 242 |

TABLE 1-continued

Exemplary Toxin-Based Peptides

| Sequence/structure | Shorthand designation | SEQ ID NO: |
|---|---|---|
| AAAISCVGSPECPPKCRAQGCKNGKCMNRKCKCYYC-amide | Vm24 | 243 |
| RTCKDLIPVSECTDIRCRTSMKYRLNLCRKTCGSC | HmK | 244 |
| GCKDNFSANTCKHVKANNNCGSQKYATNCAKTCGKC | Aek | 245 |
| ACKDNFAAATCKHVKENKNCGSQKYATNCAKTCGKC | AsKS | 246 |
| TIINVKCTSPKQCLPPCKAQFGQSAGAKCMNGKCKCYPH | MgTx | 247 |
| GVEINVKCSGSPQCLKPCKDAGMRFGKCMNRKCHCTPK | KTx1 | 248 |
| VRIPVSCKHSGQCLKPCKDAGMRFGKCMNGKCDCTPK | KTx2 | 249 |
| VSCTGSKDCYAPCRKQTGCPNAKCINKSCKCYGC | MTx | 250 |
| QFTDVDCSVSKECWSVCKDLFGVDRGKCMGKKCRCY | IbTx | 251 |
| GVPTDVKCRGSPQCIQPCKDAGMRFGKCMNGKCHCTPK | ODK2 | 252 |
| GVPINVKCRGSPQCIQPCRDAGMRFGKCMNGKCHCTPQ | Bs6 | 253 |
| GVPINVKCRGSRDCLDPCKKAGMRFGKCINSKCHCTP | BoiTx1 | 254 |
| GVPINVPCTGSPQCIKPCKDAGMRFGKCMNRKCHCTPK | AgTx3 | 255 |
| VGIPVSCKHSGQCIKPCKDAGMRFGKCMNRKCDCTPK | KTx3 | 256 |

"ShK" peptides are a subtype of toxin peptides that can also be used in the methods and pharmaceutical compositions described herein. ShK peptides were originally isolated from the Caribbean sea anemone *Stichodactyla helianthus*. ShK peptides serve as inhibitors of Kv1.3 channels. By inhibiting Kv1.3 channels, ShK can suppress activation, proliferation and/or cytokine production of or by $T_{EM}$, in certain embodiments, at picomolar concentrations.

As used herein, an "inhibitor" is any toxin-based therapeutic peptide that decreases or eliminates a biological activity that normally results based on the interaction of a compound with a receptor including biosynthetic and/or catalytic activity, receptor or signal transduction pathway activity, gene transcription or translation, cellular protein transport, etc.

A native ShK peptide is described in, for example, Pennington, et al., Int. J. Pept. Protein Res., 46, 354-358 (1995). Exemplary ShK structures that are within the scope of the present disclosure are also published in Beeton, et al., Mol. Pharmacol., 67, 1369-1381 (2005); U. S. Publication No. 2008/0221024; PCT Publication No. WO/2012/170392; and in U.S. Pat. Nos. 8,080,523 and 8,440,621.

"ShK-based peptides" include any synthetic or naturally-known ShK peptides as well as variants, D-substituted analogs, carboxy-terminal amides, modifications, derivatives and pharmaceutically acceptable salts thereof.

Particular exemplary ShK-based peptides for use with the methods and pharmaceutical compositions disclosed herein can include those listed in Table 2, and as shown in the sequence listing as SEQ ID NO: 1-224. In various embodiments, a method of treating ophthalmic conditions includes administering a therapeutically-effective amount of a ShK-based peptide of Table 2 (SEQ ID NO: 1-224). In various embodiments, the ShK-based peptides of Table 2 (SEQ ID NO: 1-224) can be used in the production of a pharmaceutical composition (or medicament) to treat ophthalmic conditions. ShK-based peptides utilized in particular embodiments disclosed herein include those of SEQ ID NO: 1, SEQ ID NO: 49, SEQ ID NO: 210, SEQ ID NO: 217, and SEQ ID NO: 221.

TABLE 2

Exemplary ShK-Based Peptides

| Sequence/structure | Shorthand ID | SEQ ID NO: |
|---|---|---|
| RSCIDTIPKSRCTAFQCKHSMKYRLSFCRKTCGTC | ShK | 1 |
| RSCIDTIPKSRCTAFQSKHSMKYRLSFCRKTSGTC | ShK-S17/S32 | 2 |
| RSSIDTIPKSRCTAFQCKHSMKYRLSFCRKTCGTS | ShK-S3/S35 | 3 |
| SSCIDTIPKSRCTAFQCKHSMKYRLSFCRKTCGTC | ShK-S1 | 4 |
| (N-acetylR)SCIDTIPKSRCTAFQCKHSMKYRLSFCRKTCGTC | ShK-N-acetylarg1 | 5 |
| SCIDTIPKSRCTAFQCKHSMKYRLSFCRKTCGTC | ShK-d1 | 6 |
| CIDTIPKSRCTAFQCKHSMKYRLSFCRKTCGTC | ShK-d2 | 7 |
| ASCIDTIPKSRCTAFQCKHSMKYRLSFCRKTCGTC | ShK-A1 | 8 |
| QCIDTIPKSRCTAFQCKHSMKYRLSFCRKTCGTC | ShK-Q2 d1 | 9 |
| ACIDTIPKSRCTAFQCKHSMKYRLSFCRKTCGTC | ShK-A2 d1 | 10 |
| TCIDTIPKSRCTAFQCKHSMKYRLSFCRKTCGTC | ShK-T2 d1 | 11 |
| RQCIDTIPKSRCTAFQCKHSMKYRLSFCRKTCGTC | ShK-Q2 | 12 |
| RACIDTIPKSRCTAFQCKHSMKYRLSFCRKTCGTC | ShK-A2 | 13 |

TABLE 2-continued

Exemplary ShK-Based Peptides

| Sequence/structure | Shorthand ID | SEQ ID NO: |
|---|---|---|
| RTCIDTIPKSRCTAFQCKHSMKYRLSFCRKTCGTC | ShK-T2 | 14 |
| AQCIDTIPKSRCTAFQCKHSMKYRLSFCRKTCGTC | ShK-Q2 | 15 |
| AACIDTIPKSRCTAFQCKHSMKYRLSFCRKTCGTC | ShK-A1/A2 | 16 |
| ATCIDTIPKSRCTAFQCKHSMKYRLSFCRKTCGTC | ShK-A1/T2 | 17 |
| RSCADTIPKSRCTAFQCKHSMKYRLSFCRKTCGTC | ShK-A1/A4 | 18 |
| RSCADTIPKSRCTAAQCKHSMKYRLSFCRKTCGTC | ShK-A4/A15 | 19 |
| RSCADTIPKSRCTAAQCKHSMKYRASFCRKTCGTC | ShK-A4/A15/A25 | 20 |
| RSCIDAIPKSRCTAFQCKHSMKYRLSFCRKTCGTC | ShK-A6 | 21 |
| RSCIDTIPKSRCTAFQCKHSMKYRLSFCRKTCGTC-amide | ShK-T6 | 22 |
| RSCIDYIPKSRCTAFQCKHSMKYRLSFCRKTCGTC | ShK-Y6 | 23 |
| RSCIDLIPKSRCTAFQCKHSMKYRLSFCRKTCGTC | ShK-L6 | 24 |
| RSCIDTAPKSRCTAFQCKHSMKYRLSFCRKTCGTC | ShK-A7 | 25 |
| RSCADTIPKSRCTAFQCKHSMKYRLSFCRKTCGTC | ShK-A4 | 26 |
| RSCIDTIAKSRCTAFQCKHSMKYRLSFCRKTCGTC | ShK-A8 | 27 |
| RSCIDTIPASRCTAFQCKHSMKYRLSFCRKTCGTC | ShK-A9 | 28 |
| RSCIDTIPESRCTAFQCKHSMKYRLSFCRKTCGTC | ShK-E9 | 29 |
| RSCIDTIPQSRCTAFQCKHSMKYRLSFCRKTCGTC | ShK-Q9 | 30 |
| RSCIDTIPKARCTAFQCKHSMKYRLSFCRKTCGTC | ShK-A10 | 31 |
| RSCIDTIPKSACTAFQCKHSMKYRLSFCRKTCGTC | ShK-A11 | 32 |
| RSCIDTIPKSECTAFQCKHSMKYRLSFCRKTCGTC | ShK-E11 | 33 |
| RSCIDTIPKSQCTAFQCKHSMKYRLSFCRKTCGTC | ShK-Q11 | 34 |
| RSCIDTIPKSRCAAFQCKHSMKYRLSFCRKTCGTC | ShK-A13 | 35 |
| RSCIDTIPKSRCTAAQCKHSMKYRLSFCRKTCGTC | ShK-A15 | 36 |
| RSCIDTIPKSRCTAWQCKHSMKYRLSFCRKTCGTC | ShK-W15 | 37 |
| RSCIDTIPKSRCTA[X(s1)]QCKHSMKYRLSFCRKTCGTC | ShK-X15 | 38 |
| RSCIDTIPKSRCTAAQCKHSMKYRASFCRKTCGTC | ShK-A15/A25 | 39 |
| RSCIDTIPKSRCTAFACKHSMKYRLSFCRKTCGTC | ShK-A16 | 40 |
| RSCIDTIPKSRCTAFECKHSMKYRLSFCRKTCGTC | ShK-E16 | 41 |
| RSCIDTIPKSRCTAFQCAHSMKYRLSFCRKTCGTC | ShK-A18 | 42 |
| RSCIDTIPKSRCTAFQCEHSMKYRLSFCRKTCGTC | ShK-E18 | 43 |
| RSCIDTIPKSRCTAFQCKASMKYRLSFCRKTCGTC | ShK-A19 | 44 |
| RSCIDTIPKSRCTAFQCKKSMKYRLSFCRKTCGTC | ShK-K19 | 45 |
| RSCIDTIPKSRCTAFQCKHAMKYRLSFCRKTCGTC | ShK-A20 | 46 |
| RSCIDTIPKSRCTAFQCKHSAKYRLSFCRKTCGTC | ShK-A21 | 47 |
| RSCIDTIPKSRCTAFQCKHS[X(s2)]KYRLSFCRKTCGTC | ShK-X21 | 48 |

TABLE 2-continued

| Exemplary ShK-Based Peptides | | |
|---|---|---|
| Sequence/structure | Shorthand ID | SEQ ID NO: |
| RSCIDTIPKSRCTAFQCKHS(Nle)KYRLSFCRKTCGTC | ShK-Nle21 | 49 |
| RSCIDTIPKSRCTAFQCKHSMAYRLSFCRKTCGTC | ShK-A22 | 50 |
| RSCIDTIPKSRCTAFQCKHSMEYRLSFCRKTCGTC | ShK-E22 | 51 |
| RSCIDTIPKSRCTAFQCKHSMRYRLSFCRKTCGTC | ShK-R22 | 52 |
| RSCIDTIPKSRCTAFQCKHSM[X(s3)]YRLSFCRKTCGTC | ShK-X22 | 53 |
| RSCIDTIPKSRCTAFQCKHSM(Nle)YRLSFCRKTCGTC | ShK-Nle22 | 54 |
| RSCIDTIPKSRCTAFQCKHSM(Orn)YRLSFCRKTCGTC | ShK-Orn22 | 55 |
| RSCIDTIPKSRCTAFQCKHSM(Homocit)YRLSFCRKTCGTC | ShK-Homocit22 | 56 |
| RSCIDTIPKSRCTAFQCKHSM(Dap)YRLSFCRKTCGTC | ShK-diamino-propionic22 | 57 |
| RSCIDTIPKSRCTAFQCKHSMKARLSFCRKTCGTC | ShK-A23 | 58 |
| RSCIDTIPKSRCTAFQCKHSMKSRLSFCRKTCGTC | ShK-S23 | 59 |
| RSCIDTIPKSRCTAFQCKHSMKFRLSFCRKTCGTC | ShK-F23 | 60 |
| RSCIDTIPKSRCTAFQCKHSMK[X(s4)]RLSFCRKTCGTC | ShK-X23 | 61 |
| RSCIDTIPKSRCTAFQCKHSMK(NitroF)RLSFCRKTCGTC | ShK-Nitrophe23 | 62 |
| RSCIDTIPKSRCTAFQCKHSMK(AminoF)RLSFCRKTCGTCC | ShK-Aminophe23 | 63 |
| RSCIDTIPKSRCTAFQCKHSMK(BenzylF)RLSFCRKTCGTC | ShK-Benzylphe23 | 64 |
| RSCIDTIPKSRCTAFQCKHSMKYALSFCRKTCGTC | ShK-A24 | 65 |
| RSCIDTIPKSRCTAFQCKHSMKYELSFCRKTCGTC | ShK-E24 | 66 |
| RSCIDTIPKSRCTAFQCKHSMKYRASFCRKTCGTC | ShK-A25 | 67 |
| RSCIDTIPKSRCTAFQCKHSMKYRLAFCRKTCGTC | ShK-A26 | 68 |
| RSCIDTIPKSRCTAFQCKHSMKYRLSACRKTCGTC | ShK-A27 | 69 |
| RSCIDTIPKSRCTAFQCKHSMKYRLS[X(s27)]CRKTCGTC | ShK-X27 | 70 |
| RSCIDTIPKSRCTAFQCKHSMKYRLSFCAKTCGTC | ShK-A29 | 71 |
| RSCIDTIPKSRCTAFQCKHSMKYRLSFCRATCGTC | ShK-A30 | 72 |
| RSCIDTIPKSRCTAFQCKHSMKYRLSFCRKACGTC | ShK-A31 | 73 |
| RSCIDTIPKSRCTAFQCKHSMKYRLSFCRKTCGAC | ShK-A34 | 74 |
| SCADTIPKSRCTAFQCKHSMKYRLSFCRKTCGTC | ShK-A4d1 | 75 |
| SCADTIPKSRCTAAQCKHSMKYRLSFCRKTCGTC | ShK-A4/A15d1 | 76 |
| SCADTIPKSRCTAAQCKHSMKYRASFCRKTCGTC | ShK-A4/A15/A25d1 | 77 |
| SCIDAIPKSRCTAFQCKHSMKYRLSFCRKTCGTC | ShK-A6d1 | 78 |
| SCIDTAPKSRCTAFQCKHSMKYRLSFCRKTCGTC | ShK-A7d1 | 79 |

TABLE 2-continued

Exemplary ShK-Based Peptides

| Sequence/structure | Shorthand ID | SEQ ID NO: |
|---|---|---|
| SCIDTIAKSRCTAFQCKHSMKYRLSFCRKTCGTC | ShK-A8d1 | 80 |
| SCIDTIPASRCTAFQCKHSMKYRLSFCRKTCGTC | ShK-A9d1 | 81 |
| SCIDTIPESRCTAFQCKHSMKYRLSFCRKTCGTC | ShK-E9d1 | 82 |
| SCIDTIPQSRCTAFQCKHSMKYRLSFCRKTCGTC | ShK-Q9d1 | 83 |
| SCIDTIPKARCTAFQCKHSMKYRLSFCRKTCGTC | ShK-A10d1 | 84 |
| SCIDTIPKSACTAFQCKHSMKYRLSFCRKTCGTC | ShK-A11d1 | 85 |
| SCIDTIPKSECTAFQCKHSMKYRLSFCRKTCGTC | ShK-E11d1 | 86 |
| SCIDTIPKSQCTAFQCKHSMKYRLSFCRKTCGTC | ShK-Q11d1 | 87 |
| SCIDTIPKSRCAAFQCKHSMKYRLSFCRKTCGTC | ShK-A13d1 | 88 |
| SCIDTIPKSRCTAAQCKHSMKYRLSFCRKTCGTC | ShK-A15d1 | 89 |
| SCIDTIPKSRCTAWQCKHSMKYRLSFCRKTCGTC | ShK-W15d1 | 90 |
| SCIDTIPKSRCTA[X(s15)]QCKHSMKYRLSFCRKTCG TC | ShK-X15d1 | 91 |
| SCIDTIPKSRCTAAQCKHSMKYRASFCRKTCGTC | ShK-A15/A25d1 | 92 |
| SCIDTIPKSRCTAFACKHSMKYRLSFCRKTCGTC | ShK-A16d1 | 93 |
| SCIDTIPKSRCTAFECKHSMKYRLSFCRKTCGTC | ShK-E16d1 | 94 |
| SCIDTIPKSRCTAFQCAHSMKYRLSFCRKTCGTC | ShK-A18d1 | 95 |
| SCIDTIPKSRCTAFQCEHSMKYRLSFCRKTCGTC | ShK-E18d1 | 96 |
| SCIDTIPKSRCTAFQCKASMKYRLSFCRKTCGTC | ShK-A19d1 | 97 |
| SCIDTIPKSRCTAFQCKKSMKYRLSFCRKTCGTC | ShK-K19d1 | 98 |
| SCIDTIPKSRCTAFQCKHAMKYRLSFCRKTCGTC | ShK-A20d1 | 99 |
| SCIDTIPKSRCTAFQCKHSAKYRLSFCRKTCGTC | ShK-A21d1 | 100 |
| SCIDTIPKSRCTAFQCKHS[X(s2)]KYRLSFCRKTCGT C | ShK-X21d1 | 101 |
| SCIDTIPKSRCTAFQCKHS(Nle)KYRLSFCRKTCGTC | ShK-Nle21d1 | 102 |
| SCIDTIPKSRCTAFQCKHSMAYRLSFCRKTCGTC | ShK-A22d1 | 103 |
| SCIDTIPKSRCTAFQCKHSMEYRLSFCRKTCGTC | ShK-E22d1 | 104 |
| SCIDTIPKSRCTAFQCKHSMRYRLSFCRKTCGTC | ShK-R22d1 | 105 |
| SCIDTIPKSRCTAFQCKHSM/X(s3)/YRLSFCRKTCGT C | ShK-X22d1 | 106 |
| SCIDTIPKSRCTAFQCKHSM(Nle)YRLSFCRKTCGTC | ShK-Nle22d1 | 107 |
| SCIDTIPKSRCTAFQCKHSM(Orn)YRLSFCRKTCGTC | ShK-Orn22d1 | 108 |
| SCIDTIPKSRCTAFQCKHSM(Homocit)YRLSFCRKTC GTC | ShK-Homocit22d1 | 109 |
| SCIDTIPKSRCTAFQCKHSM(Dap)YRLSFCRKTCGT C | ShK-Dap22d1 | 110 |
| SCIDTIPKSRCTAFQCKHSMKARLSFCRKTCGTC | ShK-A23d1 | 111 |
| SCIDTIPKSRCTAFQCKHSMKSRLSFCRKTCGTC | ShK-S23d1 | 112 |
| SCIDTIPKSRCTAFQCKHSMKFRLSFCRKTCGTC | ShK-F23d1 | 113 |

TABLE 2-continued

| Exemplary ShK-Based Peptides | | |
|---|---|---|
| Sequence/structure | Shorthand ID | SEQ ID NO: |
| SCIDTIPKSRCTAFQCKHSMK[X(s4)]RLSFCRKTCGTC | ShK-X23d1 | 114 |
| SCIDTIPKSRCTAFQCKHSMK(NitroF)RLSFCRKTCGTC | ShK-Nitrophe23d1 | 115 |
| SCIDTIPKSRCTAFQCKHSMK(AminoF)RLSFCRKTCGTC | ShK-Aminophe23d1 | 116 |
| SCIDTIPKSRCTAFQCKHSMK(BenzylF)RLSFCRKTCGT | ShK-Benzylphe23d1 | 117 |
| SCIDTIPKSRCTAFQCKHSMKYALSFCRKTCGTC | ShK-A24d1 | 118 |
| SCIDTIPKSRCTAFQCKHSMKYELSFCRKTCGTC | ShK-E24d1 | 119 |
| SCIDTIPKSRCTAFQCKHSMKYRASFCRKTCGTC | ShK-A25d1 | 120 |
| SCIDTIPKSRCTAFQCKHSMKYRLAFCRKTCGTC | ShK-A26d1 | 121 |
| SCIDTIPKSRCTAFQCKHSMKYRLSACRKTCGTC | ShK-A27d1 | 122 |
| SCIDTIPKSRCTAFQCKHSMKYRLS[X(s5)]CRKTCGTC | ShK-X27d1 | 123 |
| SCIDTIPKSRCTAFQCKHSMKYRLSFCAKTCGTC | ShK-A29d1 | 124 |
| SCIDTIPKSRCTAFQCKHSMKYRLSFCRATCGTC | ShK-A30d1 | 125 |
| SCIDTIPKSRCTAFQCKHSMKYRLSFCRKACGTC | ShK-A31d1 | 126 |
| SCIDTIPKSRCTAFQCKHSMKYRLSFCRKTCGAC | ShK-A34d1 | 127 |
| YSCIDTIPKSRCTAFQCKHSMKYRLSFCRKTCGTC | ShK-Y1 | 128 |
| KSCIDTIPKSRCTAFQCKHSMKYRLSFCRKTCGTC | ShK-K1 | 129 |
| HSCIDTIPKSRCTAFQCKHSMKYRLSFCRKTCGTC | ShK-H1 | 130 |
| QSCIDTIPKSRCTAFQCKHSMKYRLSFCRKTCGTC | ShK-Q1 | 131 |
| PPRSCIDTIPKSRCTAFQCKHSMKYRLSFCRKTCGTC | PP-ShK | 132 |
| MRSCIDTIPKSRCTAFQCKHSMKYRLSFCRKTCGTC | M-ShK | 133 |
| GRSCIDTIPKSRCTAFQCKHSMKYRLSFCRKTCGTC | G-ShK | 134 |
| YSCIDTIPKSRCTAFQCKHSMAYRLSFCRKTCGTC | ShK-Y1/A22 | 135 |
| KSCIDTIPKSRCTAFQCKHSMAYRLSFCRKTCGTC | ShK-K1/A22 | 136 |
| HSCIDTIPKSRCTAFQCKHSMAYRLSFCRKTCGTC | ShK-H1/A22 | 137 |
| QSCIDTIPKSRCTAFQCKHSMAYRLSFCRKTCGTC | ShK-Q1/A22 | 138 |
| PPRSCIDTIPKSRCTAFQCKHSMAYRLSFCRKTCGTC | PP-ShK-A22 | 139 |
| MRSCIDTIPKSRCTAFQCKHSMAYRLSFCRKTCGTC | M-ShK-A22 | 140 |
| GRSCIDTIPKSRCTAFQCKHSMAYRLSFCRKTCGTC | G-ShK-A22 | 141 |
| RSCIDTIPASRCTAFQCKHSMAYRLSFCRKTCGTC | ShK-A9/A22 | 142 |
| SCIDTIPASRCTAFQCKHSMAYRLSFCRKTCGTC | ShK-A9/A22d1 | 143 |
| RSCIDTIPVSRCTAFQCKHSMKYRLSFCRKTCGTC | ShK-V9 | 144 |
| RSCIDTIPVSRCTAFQCKHSMAYRLSFCRKTCGTC | ShK-V9/A22 | 145 |
| SCIDTIPVSRCTAFQCKHSMKYRLSFCRKTCGTC | ShK-V9d1 | 146 |

TABLE 2-continued

Exemplary ShK-Based Peptides

| Sequence/structure | Shorthand ID | SEQ ID NO: |
|---|---|---|
| SCIDTIPVSRCTAFQCKHSMAYRLSFCRKTCGTC | ShK-V9/A22d1 | 147 |
| RSCIDTIPESRCTAFQCKHSMAYRLSFCRKTCGTC | ShK-E9/A22 | 148 |
| SCIDTIPESRCTAFQCKHSMAYRLSFCRKTCGTC | ShK-E9/A22d1 | 149 |
| RSCIDTIPKSACTAFQCKHSMAYRLSFCRKTCGTC | ShK-A11/A22 | 150 |
| SCIDTIPKSACTAFQCKHSMAYRLSFCRKTCGTC | ShK-A11/A22d1 | 151 |
| RSCIDTIPKSECTAFQCKHSMAYRLSFCRKTCGTC | ShK-E11/A22 | 152 |
| SCIDTIPKSECTAFQCKHSMAYRLSFCRKTCGTC | ShK-E11/A22d1 | 153 |
| RSCIDTIPKSRCTDFQCKHSMKYRLSFCRKTCGTC | ShK-D14 | 154 |
| RSCIDTIPKSRCTDFQCKHSMAYRLSFCRKTCGTC | ShK-D14/A22 | 155 |
| SCIDTIPKSRCTDFQCKHSMKYRLSFCRKTCGTC | ShK-D14d1 | 156 |
| SCIDTIPKSRCTDFQCKHSMAYRLSFCRKTCGTC | ShK-D14/A22d1 | 157 |
| RSCIDTIPKSRCTAAQCKHSMAYRLSFCRKTCGTC | ShK-A15/A22 | 158 |
| SCIDTIPKSRCTAAQCKHSMAYRLSFCRKTCGTC | ShK-A15/A22d1 | 159 |
| RSCIDTIPKSRCTAIQCKHSMKYRLSFCRKTCGTC | ShK-I15 | 160 |
| RSCIDTIPKSRCTAIQCKHSMAYRLSFCRKTCGTC | ShK-I15/A22 | 161 |
| SCIDTIPKSRCTAIQCKHSMKYRLSFCRKTCGTC | ShK-I15d1 | 162 |
| SCIDTIPKSRCTAIQCKHSMAYRLSFCRKTCGTC | ShK-I15/A22d1 | 163 |
| RSCIDTIPKSRCTAVQCKHSMKYRLSFCRKTCGTC | ShK-V15 | 164 |
| RSCIDTIPKSRCTAVQCKHSMAYRLSFCRKTCGTC | ShK-V15/A22 | 165 |
| SCIDTIPKSRCTAVQCKHSMKYRLSFCRKTCGTC | ShK-V15d1 | 166 |
| SCIDTIPKSRCTAVQCKHSMAYRLSFCRKTCGTC | ShK-V15/A22d1 | 167 |
| RSCIDTIPKSRCTAFRCKHSMKYRLSFCRKTCGTC | ShK-R16 | 168 |
| RSCIDTIPKSRCTAFRCKHSMAYRLSFCRKTCGTC | ShK-R16/A22 | 169 |
| SCIDTIPKSRCTAFRCKHSMKYRLSFCRKTCGTC | ShK-R16d1 | 170 |
| SCIDTIPKSRCTAFRCKHSMAYRLSFCRKTCGTC | ShK-R16/A22d1 | 171 |
| RSCIDTIPKSRCTAFKCKHSMKYRLSFCRKTCGTC | ShK-K16 | 172 |
| RSCIDTIPKSRCTAFKCKHSMAYRLSFCRKTCGTC | ShK-K16/A22 | 173 |
| SCIDTIPKSRCTAFKCKHSMKYRLSFCRKTCGTC | ShK-K16d1 | 174 |
| SCIDTIPKSRCTAFKCKHSMAYRLSFCRKTCGTC | ShK-K16/A22d1 | 175 |
| RSCIDTIPASECTAFQCKHSMKYRLSFCRKTCGTC | ShK-A9/E11 | 176 |
| RSCIDTIPASECTAFQCKHSMAYRLSFCRKTCGTC | ShK-A9/E11/A22 | 177 |
| SCIDTIPASECTAFQCKHSMKYRLSFCRKTCGTC | ShK-A9/E11d1 | 178 |
| SCIDTIPASECTAFQCKHSMAYRLSFCRKTCGTC | ShK-A9/E11/A22d1 | 179 |
| RSCIDTIPVSECTAFQCKHSMKYRLSFCRKTCGTC | ShK-V9/E11 | 180 |
| RSCIDTIPVSECTAFQCKHSMAYRLSFCRKTCGTC | ShK-V9/E11/A22 | 181 |
| SCIDTIPVSECTAFQCKHSMKYRLSFCRKTCGTC | ShK-V9/E11d1 | 182 |
| SCIDTIPVSECTAFQCKHSMAYRLSFCRKTCGTC | ShK-V9/E11/A22d1 | 183 |

TABLE 2-continued

Exemplary ShK-Based Peptides

| Sequence/structure | Shorthand ID | SEQ ID NO: |
|---|---|---|
| RSCIDTIPVSACTAFQCKHSMKYRLSFCRKTCGTC | ShK-V9/A11 | 184 |
| RSCIDTIPVSACTAFQCKHSMAYRLSFCRKTCGTC | ShK-V9/A11/A22 | 185 |
| SCIDTIPVSACTAFQCKHSMKYRLSFCRKTCGTC | ShK-V9/A11d1 | 186 |
| SCIDTIPVSACTAFQCKHSMAYRLSFCRKTCGTC | ShK-V9/A11/A22d1 | 187 |
| RSCIDTIPASACTAFQCKHSMKYRLSFCRKTCGTC | ShK-A9/A11 | 188 |
| RSCIDTIPASACTAFQCKHSMAYRLSFCRKTCGTC | ShK-A9/A11/A22 | 189 |
| SCIDTIPASACTAFQCKHSMKYRLSFCRKTCGTC | ShK-A9/A11 d1 | 190 |
| SCIDTIPASACTAFQCKHSMAYRLSFCRKTCGTC | ShK-A9/A11/A22d1 | 191 |
| RSCIDTIPKSECTDIRCKHSMKYRLSFCRKTCGTC | ShK-E11/D14/I15/R16 | 192 |
| RSCIDTIPKSECTDIRCKHSMAYRLSFCRKTCGTC | ShK-E11/D14/I15/R16/A22 | 193 |
| SCIDTIPKSECTDIRCKHSMKYRLSFCRKTCGTC | ShK-E11/D14/I15/R16d1 | 194 |
| SCIDTIPKSECTDIRCKHSMAYRLSFCRKTCGTC | ShK-E11/D14/I15/R16/A22d1 | 195 |
| RSCIDTIPVSECTDIRCKHSMKYRLSFCRKTCGTC | ShK-V9/E11/D14/I15/R16 | 196 |
| RSCIDTIPVSECTDIRCKHSMAYRLSFCRKTCGTC | ShK-V9/E11/D14/I15/R16/A22 | 197 |
| SCIDTIPVSECTDIRCKHSMKYRLSFCRKTCGTC | ShK-V9/E11/D14/I15/R16 d1 | 198 |
| SCIDTIPVSECTDIRCKHSMAYRLSFCRKTCGTC | ShK-V9/E11/D14/I15/R16/A22 d1 | 199 |
| RSCIDTIPVSECTDIQCKHSMKYRLSFCRKTCGTC | ShK-V9/E11/D14/I15 | 200 |
| RSCIDTIPVSECTDIQCKHSMAYRLSFCRKTCGTC | ShK-V9/E11/D14/I15/A22 | 201 |
| SCIDTIPVSECTDIQCKHSMKYRLSFCRKTCGTC | ShK-V9/E11/D14/I15 d1 | 202 |
| SCIDTIPVSECTDIQCKHSMAYRLSFCRKTCGTC | ShK-V9/E11/D14/I15/A22 d1 | 203 |
| RTCKDLIPVSECTDIRCKHSMKYRLSFCRKTCGTC | ShK-T2/K4/L6/V9/E11/D14/I15/R16 | 204 |
| RTCKDLIPVSECTDIRCKHSMAYRLSFCRKTCGTC | ShK-T2/K4/L6/V9/E11/D14/I15/R16/A22 | 205 |
| TCKDLIPVSECTDIRCKHSMKYRLSFCRKTCGTC | ShK-T2/K4/L6/V9/E11/D14/I15/R16 d1 | 206 |
| TCKDLIPVSECTDIRCKHSMAYRLSFCRKTCGTC | ShK-T2/K4/L6/V9/E11/D14/I15/R16/A22 d1 | 207 |
| (L-PhosphoTyr)-AEEAc-RSCIDTIPKSRCTAFQCKHSMKYRLSFCRKTCGTC | ShK(L5) | 208 |
| (L-Tyr)-AEEAc-RSCIDTIPKSRCTAFQCKHSMKYRLSFCRKTCGTC | ShK(L4) | 209 |

TABLE 2-continued

Exemplary ShK-Based Peptides

| Sequence/structure | Shorthand ID | SEQ ID NO: |
|---|---|---|
| (L-Tyr)-AEEAc-RSCIDTIPKSRCTAFQCKHSMKYRLSFCRKTCGTC-amide | ShK-198 | 210 |
| QSCADTIPKSRCTAAQCKHSMKYRLSFCRKTCGTC | ShK-Q1/A4/A15 | 211 |
| QSCADTIPKSRCTAAQCKHSMAYRLSFCRKTCGTC | ShK-Q1/A4/A15/A22 | 212 |
| QSCADTIPKSRCTAAQCKHSM(Dap)YRLSFCRKTCGTC | ShK-Q1/A4/A15/Dap22 | 213 |
| QSCADTIPKSRCTAAQCKHSMKYRASFCRKTCGTC | ShK-Q1/A4/A15/A25 | 214 |
| QSCADTIPKSRCTAAQCKHSMAYRASFCRKTCGTC | ShK-Q1/A4/A15/A22/A25 | 215 |
| QSCADTIPKSRCTAAQCKHSM(Dap)YRASFCRKTCGTC | ShK-Q1/A4/A15/Dap22/A25 | 216 |
| (L-PhosphoTyr)-AEEAc-RSCIDTIPKSRCTAFQCKHSMKYRLSFCRKTCGTC-amide | ShK-186 | 217 |
| (Para-phosphono-Phe)-AEEAc-RSCIDTIPKSRCTAFQCKHS(Nle)KYRLSFCRKTCGTC-amide | ShK-192 | 218 |
| (Phosphonomethyl-Phe)-AEEAc-RSCIDTIPKSRCTAFQCKHSMKYRLSFCRKTCGTC-amide | ShK-191 | 219 |
| (Phosphonomethyl-Phe)-AEEAc-RSCIDTIPKSRCTAFQCKHS(Nle)KYRLSFCRKTCGTC-amide | ShK-191/Nle21 | 220 |
| DOTA-aminohexanoicacid-(L-Tyr)-AEEAc-RSCIDTIPKSRCTAFQCKHSMKYRLSFCRKTCGTC-amide | ShK-221 | 221 |
| (Para-phosphono-Phe)-AEEAc-RSCIDTIPKSRCTAFKCKHS(Nle)KYRLSFCRKTCGTC-amide | ShK-223 | 222 |
| (Para-phosphono-Phe)-AEEAc-RSCIDTIPKSRCTAFQCKHSMKYRLSFCRKTCGTC-amide | ShK-190 | 223 |
| RSCIDTIPKSRCTAFQCKHS(Nle)(Dap)YRLSFCRKTCGTC | | 224 |

Notes:
X(s1), X(s2), X(s3), etc. each refer independently to nonfunctional amino acid residues.
N-acetylR refers to N-acetylarginine
Nle refers to Norleucine
Orn refers to Ornithine
Homocit refers to Homocitrulline
NitroF refers to Nitrophenylalanine
AminoF refers to Aminophenylalanine
BenzylF refers to Benzylphenylalanine
AEEAc refers to Aminoethyloxyethyloxyacetic acid
Dap refers to Diaminopropionic acid
DOTA refers to 1,4,7,10-tetraazacyclododecane-1,4,7,10-tetraacetic acid Those skilled in the art are aware of techniques for designing toxin-based therapeutic peptides with enhanced properties, such as alanine scanning, rational design based on alignment mediated mutagenesis using known sequences and/or molecular modeling. For example, toxin-based therapeutic peptides can be designed to remove protease cleavage sites (e.g., trypsin cleavage sites at K or R residues and/or chymotrypsin cleavage sites at F, Y, or W residues). Nonhydrolyzable phosphate substitutions also impart a stabilizing effect on the phosphate groups, as well as stability against phosphatase enzymes. Nonhydrolyzable phosphate groups include phosphonate analogs of phosphotyrosine such as 4-phosphonomethylphenylalanine (Pmp) 4-phosphonodifluoromethylphenylalanine (F2Pmp), para-phosphonophenylalanine, monofluorophosphonomethyl-phenylalanine, sulfono(difluormethyl)phenylalanine (F2Smp) and hydroxylphosphonomethylphenylalanine. In other embodiments, phosphotyrosine mimetics may be used such as for example OMT, FOMT and other analogs that utilize carboxylic acid groups to replicate phosphate functionality as described in Burke and Lee, Acc. Chem. Res., 36, 426-433 (2003). In a still further embodiment, nonhydrolyzable analogs include methyl-, aryloxy- and thio-ethyl phosphonic acids. In a still further embodiment, nonhydrolyzable phosphate derivatives include difluoromethylenephosphonic and difluoromethylenesulfonic acid.

To improve the pharmacokinetic and pharmacodynamic (PK/PD) properties of the structure of toxin-based therapeutic peptides, residues that are sensitive to degradation properties can be substituted, replaced, or modified. Modification of the C-terminal acid function with an amide can also impart stability. These changes to the primary structure of toxin-based therapeutic peptides can be combined with an anionic moiety at the N-terminus to produce a stable and selective Kv1.3 blocker. In order to produce a toxin-based therapeutic peptide with a higher half-life in vivo, variants or modifications of the peptides can be prepared wherein key proteolytic digestion sites may be substituted to reduce protease susceptibility. This may include substitution of nonessential residues with conservative isosteric replacements (e.g., Lys to Lys (acetyl) or Gln) and or neutral replacements (Ala).

"Variants" of toxin-based therapeutic peptides disclosed herein include peptides having one or more amino acid additions, deletions, stop positions, or substitutions, as compared to a toxin-based or ShK-based peptide disclosed herein.

An amino acid substitution can be a conservative or a non-conservative substitution. Variants of toxin-based therapeutic peptides disclosed herein can include those having one or more conservative amino acid substitutions. As used herein, a "conservative substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cys; acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of toxin-based therapeutic peptides disclosed herein also include peptides with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a peptide sequence disclosed herein.

Variants of toxin-based therapeutic peptides for use with the methods disclosed herein based on toxin-based peptides include peptides that share: 70% sequence identity with any of SEQ ID NO:225-256; 75% sequence identity with any of SEQ ID NO:225-256; 80% sequence identity with any of SEQ ID NO:225-256; 81% sequence identity with any of SEQ ID NO:225-256; 82% sequence identity with any of SEQ ID NO:225-256; 83% sequence identity with any of SEQ ID NO:225-256; 84% sequence identity with any of SEQ ID NO:225-256; 85% sequence identity with any of SEQ ID NO:225-256; 86% sequence identity with any of SEQ ID NO: 225-256; 87% sequence identity with any of SEQ ID NO:225-256; 88% sequence identity with any of SEQ ID NO:225-256; 89% sequence identity with any of SEQ ID NO:225-256; 90% sequence identity with any of SEQ ID NO:225-256; 91% sequence identity with any of SEQ ID NO:225-256; 92% sequence identity with any of SEQ ID NO:225-256; 93% sequence identity with any of SEQ ID NO:225-256; 94% sequence identity with any of SEQ ID NO:225-256; 95% sequence identity with any of SEQ ID NO:225-256; 96% sequence identity with any of SEQ ID NO:225-256; 97% sequence identity with any of SEQ ID NO:225-256; 98% sequence identity with any of SEQ ID NO:225-256; or 99% sequence identity with any of SEQ ID NO:225-256.

Variants of toxin-based therapeutic peptides for use with the methods disclosed herein based on ShK-based peptides include peptides that share: 80% sequence identity with any of SEQ ID NO:1-224; 81% sequence identity with any of SEQ ID NO:1-224; 82% sequence identity with any of SEQ ID NO:1-224; 83% sequence identity with any of SEQ ID NO:1-224; 84% sequence identity with any of SEQ ID NO:1-224; 85% sequence identity with any of SEQ ID NO:1-224; 86% sequence identity with any of SEQ ID NO:1-224; 87% sequence identity with any of SEQ ID NO:1-224; 88% sequence identity with any of SEQ ID NO:1-224; 89% sequence identity with any of SEQ ID NO:1-224; 90% sequence identity with any of SEQ ID NO:1-224; 91% sequence identity with any of SEQ ID NO:1-224; 92% sequence identity with any of SEQ ID NO:1-224; 93% sequence identity with any of SEQ ID NO:1-224; 94% sequence identity with any of SEQ ID NO:1-224; 95% sequence identity with any of SEQ ID NO:1-224; 96% sequence identity with any of SEQ ID NO:1-224; 97% sequence identity with any of SEQ ID NO:1-224; 98% sequence identity with any of SEQ ID NO:1-224; or 99% sequence identity with any of SEQ ID NO:1-224.

Particular exemplary embodiments include toxin-based therapeutic peptides wherein the peptides share 80% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity with the formula of SEQ ID NO:208. In another embodiment, variants for use with the methods disclosed herein include peptides sharing 80% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity with the formula of SEQ ID NO:209. In another embodiment, variants for use with the methods disclosed herein include peptides sharing 80% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity with the formula of SEQ ID NO:217. In another embodiment, variants for use with the methods disclosed herein include peptides sharing 80% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity, with the formula of SEQ ID NO:210. In another embodiment, variants for use with the methods disclosed herein include peptides sharing 80% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, or 99% sequence identity with the formula of SEQ ID NO:218.

"% sequence identity" refers to a relationship between two or more sequences, as determined by comparing the sequences. In the art, "identity" also means the degree of sequence relatedness between peptide sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, NJ (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine sequence identity are designed to give the best match between the sequences tested. Methods to determine sequence identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters which originally load with the software when first initialized.

"D-substituted analogs" include toxin-based therapeutic peptides disclosed herein having one more L-amino acids substituted with D-amino acids. The D-amino acid can be the same amino acid type as that found in the peptide sequence or can be a different amino acid. Accordingly, D-analogs are also variants.

"Modifications" include toxin-based therapeutic peptides disclosed herein wherein one or more amino acids have been replaced with a non-amino acid component, or where the amino acid has been conjugated to a functional group or a functional group has been otherwise associated with an amino acid or peptide. The modified amino acid may be, e.g., a glycosylated amino acid, a PEGylated amino acid, a farnesylated amino acid, an acetylated amino acid, a biotinylated amino acid, an amino acid conjugated to a lipid moiety, an amino acid conjugated to human serum albumin, or an amino acid conjugated to an organic derivatizing agent. The presence of modified amino acids may be advantageous in, for example, (a) increasing peptide serum half-life and/or functional in vivo half-life, (b) reducing peptide antigenicity, (c) increasing peptide storage stability, (d) increasing peptide solubility, (e) prolonging circulating time, and/or (f) increasing bioavailability, e.g. increasing the area under the curve (AUCsc). Amino acid(s) can be modified, for example, co-translationally or post-translationally during recombinant production (e.g., N-linked glycosylation at N—X—S/T motifs during expression in mammalian cells) or modified by synthetic means. The modified amino acid can be within the sequence or at the terminal end of a sequence. Modifications can include derivatives as described elsewhere herein.

The C-terminus may be a carboxylic acid or an amide group, preferably a carboxylic acid group for each of the toxin-based therapeutic peptides. The present disclosure also relates to the toxin-based therapeutic peptides further modified by (i) additions made to the C-terminus, such as Tyr, iodo-Tyr, a fluorescent tag, or (ii) additions made to the N-terminus, such as Tyr, iodo-Tyr, pyroglutamate, or a fluorescent tag.

In addition, residues or groups of residues known to the skilled artisan to improve stability can be added to the C-terminus and/or N-terminus. Also, residues or groups of residues known to the skilled artisan to improve oral availability can be added to the C-terminus and/or N-terminus.

In particular embodiments, the C-terminus is an acid (for example, COOH) or an amide (for example, $CONH_2$). "Amide" refers to the substitution of the C-terminal hydroxyl group (OH) of an acid with $NH_2$. Such substitution is designated herein using the term "amide" or as the C-terminal amino acid —$NH_2$, as in "-Cys-$NH_2$."

The safety, potency, and specificity of a variety of therapeutic peptides have been investigated, and attaching the peptide to an organic or inorganic chemical entity that has an anionic charge has been shown to improve the suitability for use in pharmaceutical compositions. The site of attachment can be the N-terminus, but modifications are not limited to attachment at this site.

Examples of appropriate chemical entities include L-Pmp($OH_2$); D-Pmp($OH_2$); D-Pmp(OHEt); Pmp(Et2); D-Pmp(Et2); L-Tyr; L-Tyr($PO_3H_2$) (p-phospho-Tyrosine); L-Phe(p-$NH_2$); L-Phe(p-$CO_2H$); L-Aspartate; D-Aspartate; L-Glutamate; and D-Glutamate. The abbreviations used are defined as follows: Pmp (p-phosphonomethylphenylalanine); and Ppa (p-phosphatityl-phenylalanine). Alternatives to PmP and Ppa include Pfp (p-Phosphono(difluoromethyl)-Phenylalanine) and Pkp (p-Phosphono-methyketo-Phenylalanine).

Exemplary chemical entities can be attached by way of a linker, such as an aminoethyloxyethyloxy-acetyl linker (referred to herein as AEEAc), or by any other suitable means. Examples of chemical entity/linker combinations include AEEAc-L-Pmp(OH$_2$); AEEAc-D-Pmp(OH$_2$); AEEAc-D-Pmp(OHEt); AEEAc-L-Pmp(Et2); AEEAc-D-Pmp(Et2); AEEAc-L-Tyr; AEEAc-L-Tyr(PO$_3$H$_2$); AEEAc-L-Phe(p-NH$_2$); AEEAc-L-Phe(p-CO$_2$H); AEEAc-L-Aspartate; AEEAc-D-Aspartate; AEEAc-L-Glutamate; and AEEAc-D-Glutamate. In the chemical entities generally, where the amino acid residue has a chiral center, the D and/or L enantiomer of the amino acid residue can be used.

All toxin-based therapeutic peptides disclosed herein can be modified by the N-terminal attachment of aminoethyloxyethyloxyacetic acid, and/or an amide attachment at the C-terminal (for example, ShK-186; SEQ ID NO: 217). AEEAc can interchangeably refer to aminoethyloxyethyloxyacetic acid and Fmoc-aminoethyloxyethyloxyacetic acid when being used to describe the linker during the formation process. When being used to refer to the linker in specific peptides in their final state, the term refers to aminoethyloxyethyloxyacetic acid.

All toxin-based therapeutic peptides disclosed herein can be modified by the addition of polyethylene glycol, human serum albumin, antibodies, fatty acids, antibody fragments including the Fab and Fc regions, hydroxyethyl starch, dextran, oligosaccharides, polysialic acids, hyaluronic acid, dextrin, poly(2-ethyl 2-oxazolone), polyglutamic acid (PGA), N-(2-hydroxypropyl)methacrylamide copolymer (HPMA), unstructured hydrophilic sequences of amino acids including in particular the amino acids Ala, Glu, Gly, Ser and Thr, and many other linkers and additions as described in Schmidt, S. R. (ed), Fusion Protein Targeting for Biopharmaceuticals: Applications and Challenges, John Wiley and Sons: Hoboken N.J., 2013. PEG groups can be attached to c amino groups of lysine using: (a) PEG succinimidyl carbonate, (b) PEG benzotriazole carbonate, (c) PEG dichlorotriazine, (d) PEG tresylate, (e) PEG p-nitrophenyl carbonate, (f) PEG trichlorophenyl carbonate, (g) PEG carbonylimidazole and (h) PEG succinimidyl succinate. PEG groups can be attached to cysteines by degradable linkers including para- or ortho-disulfide of benzyl urethane. Site specific introduction of PEG can be achieved by reductive alkylation with PEG-aldehyde or by glyceraldehyde modification of alpha-amino groups in the presence of sodium cyanoborohydride. PEGylation chemistries have been described in numerous publications including Robert, et al., Advanced Drug Delivery Reviews, 54, 459-476 (2002). Oligosaccharides can be N-linked or O-linked. N-linked oligosaccharides, including polysialic acid are added by the producing cell line by attachment to the consensus sequence of Asn-Xxx-Ser/Thr where Xxx is anything but proline. O-linked oligosaccharides are attached to Ser or Thr.

Particular embodiments include toxin-based therapeutic peptides of SEQ ID NO: 1-224 to which an organic or inorganic chemical entity that has an anionic charge is attached via an aminoethyloxyethyloxy-acetyl linker (referred to as AEEAc).

Another example of a toxin-based therapeutic peptide is an ShK-based DOTA-conjugate of ShK-186 (referred to as ShK-221). "DOTA" refers to 1,4,7,10-tetraazacyclododecane-1,4,7,10-tetraacetic acid which can be attached to the N-terminus of the therapeutic peptides disclosed herein via aminohexanoic acid. DOTA conjugation provides a site for chelating metal atoms such as Indium or Gadolinium. Other molecules that can be conjugated to therapeutic peptides disclosed herein include diethylene triamine pentaacetic acid (DTPA), Nitrilotriacetic acid (NTA), Ethylenediaminetetraacetic acid (EDTA), Iminodiacetic acid (IDA), ethylene glycol tetraacetic acid (EGTA), 1,2-bis(o-aminophenoxy)ethane-N,N,N',N'-tetraacetic acid (BAPTA), 1,4,7-triazacyclononane-N,N',N''-triacetic acid (NOTA) and related molecules.

The present disclosure is further directed to derivatives of the disclosed toxin-based therapeutic peptides. Derivatives include toxin-based therapeutic peptides having acylic permutations in which the cyclic permutants retain the native bridging pattern of the native ShK peptide. In one embodiment, the cyclized toxin-based therapeutic peptide includes a linear toxin-based therapeutic peptide and a peptide linker, wherein the N- and C-termini of the linear toxin-based therapeutic peptide are linked via the peptide linker to form the amide cyclized peptide backbone. In some embodiments, the peptide linker includes amino acids selected from Gly, Ala, and combinations thereof.

Various cyclization methods can be applied to the toxin-based therapeutic peptides described herein. The toxin-based therapeutic peptides described herein can be readily cyclized using BOC-chemistry to introduce Ala, Gly or Ala/Gly bridges, as well as combinations thereof or other residues as described by Schnolzer et al., Int J Pept Protein Res., 40, 180-193 (1992). Cyclizing toxin-based therapeutic peptides can improve their stability, oral bioavailability and reduce the susceptibility to proteolysis, without affecting the affinity of the toxin-based therapeutic peptides for their specific targets.

Each toxin-based therapeutic peptide disclosed herein may also include additions, deletions, stop positions, substitutions, replacements, conjugations, associations, or permutations at any position including positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 of a toxin-based therapeutic peptide sequence disclosed herein. Accordingly, in particular embodiments each amino acid position of each toxin-based therapeutic peptide can be an Xaa position wherein Xaa denotes an addition, deletion, stop position, substitution, replacement, conjugation, association or permutation of the amino acid at the particular position. In particular embodiments, each toxin-based therapeutic peptide has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 Xaa positions at one or more of positions 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60.

A toxin-based therapeutic peptide can have more than one change (addition, deletion, stop position, substitution, replacement, conjugation, association or permutation) and qualify as one or more of a variant, D-substituted analog, carboxy-terminal amide, modification and/or derivative. That is, inclusion of one classification of variant, D-substituted analog, carboxy-terminal amide, modification and/or derivative is not exclusive to inclusion in other classifications and all are collectively referred to as "toxin-based therapeutic peptides" herein. One example includes SEQ ID NO: 1 wherein the amino acid at position 21 is Norleucine and/or the amino acid at position 22 is replaced with diaminopropionic acid.

In any of the peptides where position 21 is a Met, the Met can be substituted to impart a stabilizing effect against oxidation. In one embodiment, a Met at position 21 is substituted with Nle. In any of SEQ ID NO: 1-256, having a Met at position 21, this Met can be substituted with Nle. In any of SEQ ID NO: 1-256, having a Lys at position 22, this Lys can be substituted with diaminopropionic acid. Accordingly, one embodiment disclosed herein includes SEQ ID NO: 1 wherein the Met at position 21 is substituted with Nle, an amide is present at the C-terminus and/or an anionic moiety is present at the N-terminus.

"Nonfunctional amino acid residue" refers to amino acid residues in D- or L-form having sidechains that lack acidic, basic, or aromatic groups. Exemplary nonfunctional amino acid residues include M, G, A, V, I, L and Nle.

Pharmaceutical Compositions

For use in the disclosed methods, toxin-based therapeutic peptides can be provided within a pharmaceutical composition. Prodrugs of toxin-based therapeutic peptides can also be used and can be made by the addition of ester groups to increase their lipophilicity, thereby enhancing, in some embodiments, their delivery across the corneal membrane. Synthetic, natural or a mixture of natural and synthetic toxin-based therapeutic peptides can be used.

Pharmaceutical compositions include a toxin-based therapeutic peptide and at least one pharmaceutically acceptable carrier. Pharmaceutically acceptable carriers include those that do not produce significantly adverse, allergic, or other untoward reactions that outweigh the benefit of administration, whether for research, prophylactic, and/or therapeutic treatments. Exemplary pharmaceutically acceptable carriers and associated formulations are disclosed in Troy, D. B. and Beringer, P. (eds) Remington: The Science and Practice of Pharmacy, Lippincott; Philadelphia, 2006. 21st Edition. Pharmaceutical compositions are prepared to meet sterility, pyrogenicity, and/or general safety and purity standards as required by U.S. Food and Drug Administration (FDA) Office of Biological Standards and/or other relevant foreign regulatory agencies.

Typically, a toxin-based therapeutic peptide will be admixed with one or more pharmaceutically acceptable carriers chosen for the selected mode of administration. For examples of delivery methods see U.S. Pat. No. 5,844,077.

Exemplary generally used pharmaceutically acceptable carriers include any and all absorption delaying agents, antioxidants, binders, buffering agents, bulking agents, chelating agents, co-solvents, coatings, coloring agents, disintegration agents, dispersion media, emulsifiers, fillers, flavoring agents, gels, isotonic agents, lubricants, perfuming agents, preservatives, releasing agents, salts, solvents, stabilizers, sweetening agents, surfactants, wetting agents, etc. . . .

Exemplary buffering agents include citrate buffers, succinate buffers, tartrate buffers, fumarate buffers, gluconate buffers, oxalate buffers, lactate buffers, acetate buffers, phosphate buffers, histidine buffers, and trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens, methyl paraben, propyl paraben, catechol, resorcinol, cyclohexanol, and 3-pentanol.

More particular examples of preservatives for ophthalmic solutions include benzalkonium chloride ($\leq 0.025\%$), sorbic acid, benzethonium chloride ($\leq 0.01\%$), chlorobutanol ($\leq 0.5\%$), phenylmercuric acetate ($\leq 0.004\%$), phenylmercuric nitrate ($\leq 0.004\%$), thimerosal ($\leq 0.01\%$), methylparaben (0.1-0.2%) and propylparabens ($\leq 0.04\%$). Other preservatives can also act as penetration enhancers through disruption of the hydrophobic barrier of the corneal epithelium and therefore serve a dual role in an ocular pharmaceutical composition. Other preservatives that can be used include mercury derivatives, alcohols, parabens, quarternary ammonium compounds, polyquarternium compounds, chlorhexidine, PURITE® (Allergan, Inc., Irvine, Calif.) and the SOFZIA® (Alcon, Inc., Hunenberg, Switzerland) preservative system. Inclusion of preservatives is especially beneficial to prevent contamination (e.g., bacterial contamination) when pharmaceutical compositions are prepared as ophthalmic solutions packaged in a multi-dose container.

Exemplary isotonic agents include polyhydric sugar alcohols, trihydric sugar alcohols, or higher sugar alcohols, such as glycerin, erythritol, arabitol, xylitol, sorbitol, and mannitol.

Exemplary stabilizers include organic sugars, polyhydric sugar alcohols, polyethylene glycol, sulfur-containing reducing agents, amino acids, low molecular weight polypeptides, proteins, immunoglobulins, hydrophilic polymers, and polysaccharides.

Exemplary antioxidants include aloha-tocopherol, ascorbic acid, ascorbyl palmitate, butylated hydroxyanisole (BHA), butylated hydroxytoluene (BHT), citric acid, cysteine hydrochloride, ethylenediamine tetraacetic acid (EDTA), lecithin, metal chelating agents, methionine, oil soluble antioxidants, phosphoric acid, propyl gallate, sodium bisulfite, sodium metabisulfite, sodium sulfite, sorbitol, tartaric acid, and vitamin E. More particular examples/amounts of antioxidants include ethylenediaminetetraacetic acid ($\leq 0.1\%$), sodium bisulfite ($\leq 0.1\%$), sodium metabisulfite ($\leq 0.1\%$), and thiourea ($\leq 0.1\%$).

Exemplary lubricants include sodium lauryl sulfate and magnesium stearate.

Exemplary pharmaceutically acceptable salts include inorganic and organic addition salts, such as acetates, benzoates, citrates, fumarates, hydrochloride, isothionates, maleates, methane-sulfonates, nitrates, phosphates, propionates, salicylates, succinates, sulphates, tartrates, theophylline acetates, and trifluoroacetates. Lower alkyl quaternary ammonium salts can also be used.

In particular embodiments, viscosity enhancers can be added to pharmaceutical compositions to allow the pharmaceutical composition to remain in the eye longer and to increase drug contact time with, and penetration of, the ocular tissues. In various embodiments, the viscosity desired in the ophthalmic solution is between 25 and 50 centipoise. Exemplary viscosity enhancers include carboxymethylcellulose ($\leq 1\%$), hydroxyethylcellulose ($\leq 0.8\%$), hydroxypropylmethylcellulose ($\leq 1\%$), methylcellulose ($\leq 2\%$), polyvinyl alcohol ($\leq 1.4\%$), polycarbophil, gellan gum, xanthan gum, carbopol, poly(styrene-divinyl benzene) sulfonic acid, and polyvinylpyrrolidine ($\leq 1.7\%$).

Penetration enhancers for use with the toxin-based therapeutic peptides described herein can include micelle formulations based upon methoxy polyethylene glycol-hexyl-substituted polylactides (MPEG-hexPLA) that can be constructed according to the methods described in Tommaso et al., Investigative Ophthalmology & Visual Science, 53(4), 2292-2299 (April 2012). Diethylene glycol monoethyl ether (Transcutol P) can also be used as a penetration enhancer.

Solubilizers can be used in pharmaceutical compositions, including Poloxamer-407, Puronic F68, Pluronic F127, polysorbates, polyethylene-35-castor oil, hydroxypropyl-beta-cyclodextrin, methyl-beta cyclodextrin, n-octenyl succinate starch, other cyclodextrins, tyloxapol, alpha-tocopherol polyethylene glycol succinate, medium chain triglycerides, sesame oil, arachis oil, safflower oil, mustard oil, soybean oil, sunflower oil, other oils, phospholipids, surfactants, rofams, and oil-in-water emulsions containing solubilizing agents.

Nanoparticle and nanoemulsion-based systems can be used for delivery of toxin-based therapeutic peptides including those based on polyepsilon caprolactone, N-isopropylacrylamide, vinyl pyrrolidone, acrylic acid, Eudragit RS 100, Eudragit RL100, poly (lactic/glycolic) acid, and Novasorb™. Cationic nanoemulsions coated with poly-L-lysine, alginate or chitosan stabilize the nanoemulsion and facilitate its interaction with the corneal membrane. Other cationic lipids and excipients appropriate for toxin-based therapeutic peptide nanoemulsions include stearlyamine, oleylamine, polyethylenimine, N-(1-(2,3-dioleoyloxy)propyl)-N,N,N trimethylammonium (DOTAP), dioleoyl phosphatidylethanolamine (DOPE), cetrimide, benzalkonium chloride, benzethonium chloride, cetalkonium chloride, benzododecinium chloride, and cetylpyridinium. Other nano- or micro-emulsion components that can be used in the pharmaceutical compositions include osmotic agents (mannitol, glycerol, sorbitol, propylene glycol, dextrose); oils (medium chain triglycerides, triacetin, mineral oil and vegetable oils); and surfactants (polysorbates, cremephores, poloxamers, tyloxapol, vitamin-E-TPGS).

Precorneal residence time of toxin-based therapeutic peptides can be enhanced by the use of ion-actived in situ gelling systems based on gellan gum or polyacrylic acid polymer. Exposure of toxin-based therapeutic peptides to the ocular surface can be further enhanced through the use of cardopol gels, cellulose derivatives, trehalose, hydroxymethylcellulose, Poloxamer 407, Polysorbate 80, propylene glycol, polyvinyl alcohol, and polyvinyl pyrrolidone as components of the pharmaceutical composition.

Polydisperse carrier solutions can be used for the pharmaceutical compositions including Sophisen™, 3A Ofteno™, and Modusik-A Ofteno™.

Liposomal formulations, including cationic liposomes, can be used as carriers for toxin-based therapeutic peptides, and include I-alpha-dimyristoylphosphatidylglycerol, phospholipid, cholesterol, Span 40, stearylamine, and deoxycholic acid.

Toxin-based therapeutic peptides can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts. Such long acting pharmaceutical compositions can be administered in any suitable manner.

Pharmaceutical compositions for ocular administration of toxin-based therapeutic peptides also include ointments to enhance drug contact and absorption into the ocular surface. Ophthalmic ointments can contain mineral oil, white petrolatum, or lanolin and can have a melting temperature near the body temperature.

Biodegradable polymers can be used for the sustained release of toxin-based therapeutic peptides. Examples include gelatin, albumin, polyorthoesters, polyanhydrides, polyvinyl alcohol, polyesters, polymers of D-, L- and DL-lactic acid, and copolymers of lactic and glycolic acid. Such polymers can be used for subconjuntival and intraocular implants.

Additionally, toxin-based therapeutic peptides can be formulated as sustained-release systems utilizing semipermeable matrices of solid polymers. Various sustained-release materials have been established and are well known by those of ordinary skill in the art. Sustained-release systems may, depending on their chemical nature, release toxin-based therapeutic peptides following administration for a few weeks up to over 100 days.

Pharmaceutical compositions disclosed herein can also utilize microencapsulation (see, e.g., U.S. Pat. Nos. 4,352,883, 4,353,888, and 5,084,350); continuous release polymer implants (see, e.g., U.S. Pat. No. 4,883,666); and macroencapsulation (see, e.g., U.S. Pat. Nos. 5,284,761, 5,158,881, 4,976,859, and 4,968,733 and published PCT patent applications WO92/19195, WO95/05452).

In particular embodiments, pharmaceutical compositions can be prepared as eye drops, subconjunctival implants, intraocular implants, intraocular injections, intravitreal injections, intravitreal implants, sub-Tenon's capsule injections and as punctual plugs.

Suitable pharmaceutical compositions for ocular administration include solutions and suspensions. Solutions are sterile and free from particulates. Suspensions are aqueous formulations that contain solid particles. The particles are generally less than 10 microns in size to prevent irritation, such as, for example 10, 9, 8, 7, 6, 5, 4, 3, 2, or 1 micron, or less than 1 micron. In various embodiments, the particles are greater than 10 microns in size. In one embodiment, the particle size is uniform. In another embodiment, all of the particles are within 1 micron of the average particle size. In another embodiment, all of the particles are within 2 microns of the average particle size. For administration directly to the eye, the pharmaceutical compositions can be eye drops.

Pharmaceutical compositions for injection can be presented in unit dosage form, e.g. in glass ampoule or multi dose containers, e.g. glass vials. The pharmaceutical compositions for injection can take such forms as suspensions, solutions or emulsions in oily or aqueous vehicles, and can contain formulatory agents such as suspending, stabilising, preserving, and/or dispersing agents.

The toxin-based therapeutic peptides and/or pharmaceutical compositions can be in powder form for reconstitution at the time of delivery. In another embodiment, the unit dosage form of the toxin-based therapeutic peptide can be a solution of the toxin-based therapeutic peptide in a suitable diluent in sterile, hermetically sealed ampoules or sterile syringes.

In another embodiment, a lyophilized pharmaceutical composition includes less than 5% water content. In another embodiment, the lyophilized pharmaceutical composition includes less than 4.0% water content. In another embodiment, the lyophilized pharmaceutical composition includes less than 2% water content. In one embodiment, the lyophilized pharmaceutical composition includes 8-12% acetate content by weight. In another embodiment, the lyophilized pharmaceutical composition includes 10-11% acetate content by weight.

For parenteral administration, the toxin-based therapeutic peptides may be dissolved in a pharmaceutically acceptable carrier and administered as either a solution or a suspension. Exemplary pharmaceutically acceptable carriers include water, saline, dextrose solutions, fructose solutions, ethanol, or oils of animal, vegetative, or synthetic origin. The carrier may also contain other ingredients, for example, preservatives, suspending agents, solubilizing agents, buffers, and the like.

For oral administration, the toxin-based therapeutic peptides can be formulated into solid or liquid preparations such as capsules, pills, tablets, lozenges, granules, melts, powders, suspensions, or emulsions. In preparing the compositions in oral dosage form, any of the usual pharmaceutically acceptable carriers may be employed, such as, for example, carriers such as starches, sugars, diluents (such as sucrose, lactose, or starch), granulating agents, lubricants (such as magnesium stearate), binders, disintegrating agents, buffering agents, and the like in the case of oral solid preparations (such as, for example, powders, capsules and tablets); or water, glycols, oils, alcohols, preservatives, coloring agents, suspending agents, and the like in the case of oral liquid preparations (such as, for example, emulsions, syrups, suspensions, elixirs, and solutions). Such compositions can also include adjuvants, such as wetting, sweetening, flavoring, and perfuming agents. Because of their ease in administration, tablets and capsules can represent an advantageous oral dosage unit form, in which case solid pharmaceutical carriers are obviously employed. If desired, tablets may be sugar-coated or enteric-coated by standard techniques.

Preparations for oral administration can be suitably formulated to give controlled release of the toxin-based therapeutic peptides. For example the toxin-based therapeutic peptides can be encapsulated to make them stable to passage through the gastrointestinal tract while at the same time, in certain embodiments, allowing for passage across the blood brain barrier. See for example, WO96/11698.

For buccal administration the compositions can take the form of tablets or lozenges formulated in conventional manners.

For nasal or pulmonary administration or any other administration by inhalation, the toxin-based therapeutic peptides can be conveniently delivered in the form of an aerosol spray presentation for pressurized packs or a nebulizer, with the use of suitable propellant, e.g. dichlorodifluoromethane, trichlorofluoromethane, dichlorotetra-fluoroethane, carbon dioxide, or other suitable gas or mixture of gases.

When the toxin-based therapeutic peptides are administered intrathecally, they may also be dissolved in cerebrospinal fluid. Naked or unencapsulated cell grafts to the CNS can also be used. See, e.g., U.S. Pat. Nos. 5,082,670 and 5,618,531.

Pharmaceutical composition attributes like pH, osmolality, and viscosity can be adjusted to stabilize the toxin-based therapeutic peptides; to provide for efficient delivery to the eye and its structures; and to increase subject comfort. Buffers can be added to pharmaceutical compositions to adjust the pH to a range of between 4.5 and 11.5, and generally within the range of 6.5 to 8.5.

An exemplary pharmaceutical composition including a toxin-based therapeutic peptide in an ocular solution contains phosphate as the buffering agent with the pH adjusted to 6.0, 6.1, 6.2, 6.3, 6.4, or 6.5. The osmolality of the solution can be made iso-osmotic or isotonic with tears by the addition of 0.9% sodium chloride, with a range of acceptable concentration from 0.6-1.8% sodium chloride.

"Pharmaceutical composition in dosage unit form" means physically discrete coherent units suitable for medical administration, each containing a therapeutically effective amount, or a multiple (up to four times) or sub-multiple (down to a fortieth) of a therapeutically effective amount of a toxin-based therapeutic peptide with a pharmaceutically acceptable carrier. Whether the pharmaceutical composition contains a daily dose, or for example, a half, a third or a quarter of a daily dose, will depend on whether the pharmaceutical composition is to be administered once or, for example, twice, three times or four times a day, respectively.

The amount and concentration of a toxin-based therapeutic peptide in a pharmaceutical composition can be selected based on clinically relevant factors, the solubility of the toxin-based therapeutic peptide in the carrier, the potency and activity of the toxin-based therapeutic peptide, and the manner of administration of the pharmaceutical composition. It is only necessary that the toxin-based therapeutic peptide constitute a therapeutically effective amount, i.e., such that a suitable effective dosage will be consistent with the dosage form employed in single or multiple unit doses.

The pharmaceutical compositions will generally contain from 0.0001 to 99 wt. %, preferably 0.001 to 50 wt. %, more preferably 0.01 to 10 wt. % of the toxin-based therapeutic peptide by weight of the total composition.

In various embodiments, the toxin-based therapeutic peptide can be present at an amount from 0.001 mg/ml to 500 mg/ml. In additional embodiments, the toxin-based therapeutic peptide can be provided in an amount of 0.001, 0.01, 0.1, 0.5, 0.75, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 150, 200, 250, 300, 350, 400, 450 or 500 mg/ml.

One exemplary pharmaceutical composition with optimal stability and solubility for use in the methods disclosed herein includes the components shown in Table 3:

TABLE 3

Example Pharmaceutical Composition

| Component | Concentration | Purpose |
|---|---|---|
| Toxin-based therapeutic peptide (e.g., ShK186, 198 or 192) | Up to 500 mg/mL | Active agent |
| Sodium phosphate | 10 mM | Buffering agent |
| NaCl | 0.8% w/v | Tonicity modifier |
| Polysorbate 20 | 0.05% (w/v) | Surfactant | pH of 6.0

Other toxin-based therapeutic peptides can be used with the same, or similar, formulations.

In addition to the toxin-based therapeutic peptide, the pharmaceutical compositions can also contain other drug(s) or biologically-active agent(s). Examples of other drugs or biologically-active agents include analgesic agents, cytokines, and therapeutic agents in all of the major areas of clinical medicine. A cocktail is a mixture of any one of the toxin-based therapeutic peptides with another drug or biologically-active agent. In this embodiment, a common administration vehicle (e.g., pill, tablet, implant, pump, injectable solution, etc.) could contain both the toxin-based therapeutic peptides in combination with the other drugs or biologically-active agent(s).

Methods of Use

The pharmaceutical compositions of the present disclosure are useful in methods of treating ophthalmic conditions. Such methods include administering to a subject in need thereof a therapeutically effective amount of a pharmaceutical composition that includes a toxin-based therapeutic peptide. In a particular embodiment, the pharmaceutically acceptable salt can be an acetate, such as potassium acetate or sodium acetate, and the pharmaceutical composition is provided in an aqueous carrier.

Ophthalmic conditions that can be treated according to the methods disclosed herein include dry eye, uveitis, scleritis, and other inflammatory conditions of the eye such as endophthalmitis, cicatricial pemphigoid, Mooren's ulcer, cytomegalovirus-mediated retinitis and other virally-mediated inflammatory eye diseases. The present disclosure further provides methods for treating the ocular manifestations of systemic autoimmune disease such as episcleritis, keratitis, retinal vasculitis, or other diseases that involve inflammation of the cornea, retina, sclera, and orbit. Examples of systemic autoimmune diseases with ocular manifestations include systemic lupus erythematous, microscopic polyangiitis, polyarteritis nodosa, Wegener's granulomatosis (granulomatosis with polyangitis), sarcoidosis, Behçet's syndrome, Vogt-Koyanagi-Harada disease, Takayasu's arteritis, rheumatoid arthritis, Sjorgen's syndrome, relapsing polychondritis, ankylosing spondylitis, psoriasis, and Churg-Strauss syndrome. The dry eye being treated can be the result of a local or systemic immune reaction, or can have other causes.

Without limiting the foregoing, inflammatory ophthalmic conditions that can be treated according to the methods disclosed herein include eye diseases or ocular conditions associated with T-cell infiltration and activation and also include ocular conditions associated with local and/or systemic autoimmune diseases. Inflammatory ophthalmic conditions are a subset of ophthalmic conditions. Exemplary inflammatory ophthalmic conditions include and/or are associated with (e.g., caused by) acanthamoeba infection, acute retinal pigment epitheliitis, allergies, allograft in stem cell transplantation manifesting as graft vs. host disease, ankylosing spondylitis, arthritis, bacterial infection, Behcet's disease, Behcet's-related retinitis, blepharitis, cicatricial pemphigoid, chemical exposure, choroiditis, chorioretinital inflammation, Churg-Strauss syndrome, Crohn's disease, conjunctivitis, cytomegalovirus-mediated retinitis, diabetic retinopathy, dry eye, endophthalmitis, episcleritis, eye bruises, eye trauma, food allergies, foreign body exposure, fungal infection, hives, iridocyclitis, iritis, juvenile idiopathic arthritis, Kawasaki disease, keratitis, keratoconjunctivitis sicca, lupus, microscopic polyangiitis, Mooren's ulcer, mycobacterial infection, neuroretinitis, parasite infection, pediatric uveitis, polyarteritis nodosa, post-surgical conditions, posterior cyclitis, psoriasis, reactive arthritis, relapsing polychondritis, retinal vasculitis, retinitis, rheumatoid arthritis, sarcoidosis, sarcoidosis-related retinitis, seasonal allergies, scleritis, Sjorgen's syndrome, spirochete infection, Stevens-Johnson syndrome, systemic lupus erythematous, Takayasu's arteritis, toxin exposure, ulcerative colitis, uveitis, viral infection, Vogt-Koyanagi-Harada disease, and Wegener's granulomatosis (granulomatosis with polyangitis).

Methods disclosed herein include treating subjects (humans, veterinary animals (dogs, cats, reptiles, birds, etc.), livestock (horses, cattle, goats, pigs, chickens, etc.), and research animals (monkeys, rats, mice, fish, etc.) with pharmaceutical compositions disclosed herein. Treating subjects includes delivering therapeutically effective amounts of the pharmaceutical compositions. Therapeutically effective amounts include those that provide effective amounts, prophylactic treatments, and/or therapeutic treatments.

An "effective amount" is the amount of a pharmaceutical composition necessary to result in a desired physiological change in the subject. Effective amounts are often administered for research purposes. Effective amounts disclosed herein result in a desired physiological change in a research assay intended to study the effectiveness of a pharmaceutical composition in the treatment of ophthalmic conditions. Effective amounts may reduce the population of $T_{EM}$ (i.e., reduce proliferation); reduce activation of $T_{EM}$ as measured by cytokine production (e.g., IFN-γ; IL-2; IL-4; IL-10; IL-17 and IL-21) and/or perforin production; and/or reduce expression of Kv1.3 channels. Reductions can be seen based on comparisons to a reference level from a previous measure from the same subject or as compared to a reference level obtained from a dataset from a population.

A "prophylactic treatment" includes a treatment administered to a subject who does not display signs or symptoms of ophthalmic condition(s) or displays only early signs or symptoms of ophthalmic condition(s) such that treatment is administered for the purpose of diminishing, preventing, or decreasing the risk of developing the ophthalmic condition(s) further. Thus, a prophylactic treatment functions as a preventative treatment against ophthalmic condition(s). As one example, a prophylactic treatment for an inflammatory ophthalmic condition such as dry eye can diminish, prevent, or decrease the risk of developing the symptoms that can lead to a diagnosis of dry eye, such as stinging or burning of the eye; a sandy or gritty feeling as if something is in the eye; episodes of excess tears following very dry eye periods; a stringy discharge from the eye; pain and redness of the eye; episodes of blurred vision: and/or heavy eyelids, as is understood by one of ordinary skill in the art. A subject is at risk for developing the symptoms that can lead to a diagnosis of dye eye if they are likely to be exposed to a condition that can lead to dry eye, such as seasonal changes, development or flare-up of an autoimmune disorder, exposure to or infection by a virus, exposure to pollen or other irritants leading to seasonal allergies, and the like. As another example, a prophylactic treatment for an inflammatory ophthalmic condition such as uveitis can diminish, prevent, or decrease the risk of developing symptoms that can lead to a diagnosis of uveitis, such as eye redness; eye pain; light sensitivity; blurred vision; dark, floating spots in the field of vision (floaters); decreased vision; and/or whitish areas (hypopyon) inside the eye in front of the lower part of the colored area of the eye (iris), as is understood by one of ordinary skill in the art. As is understood by one of ordinary skill in the art, each of these described parameters can be evaluated with well-known objective and/or subjective measures.

A "therapeutic treatment" includes a treatment administered to a subject who displays symptoms or signs of ophthalmic condition(s) and is administered to the subject for the purpose of diminishing or eliminating those signs or symptoms of the ophthalmic condition(s). The therapeutic treatment can reduce, control, or eliminate the presence or activity of ophthalmic condition(s) and/or reduce, control or eliminate side effects of ophthalmic condition(s). As one example, a therapeutic treatment for an inflammatory ophthalmic condition such as dry eye can reduce, control, or eliminate the symptoms that can lead to a diagnosis of dry eye, such as stinging or burning of the eye; a sandy or gritty feeling as if something is in the eye; episodes of excess tears following very dry eye periods; a stringy discharge from the eye; pain and redness of the eye; episodes of blurred vision; and/or heavy eyelids, as is understood by one of ordinary skill in the art. As another example, a therapeutic treatment for an inflammatory ophthalmic condition such as uveitis can reduce, control, or eliminate the symptoms that can lead to a diagnosis of uveitis, such as eye redness; eye pain; light sensitivity; blurred vision; floaters; decreased vision; and/or hypopyon inside the eye in front of the lower part of the iris, as is understood by one of ordinary skill in the art. As is understood by one of ordinary skill in the art, each of these described parameters can be evaluated with well-known objective and/or subjective measures.

For administration, effective amounts and therapeutically effective amounts (also referred to herein as doses) can be initially estimated based on results from in vitro assays and/or animal model studies. For example, a dose can be formulated in animal models to achieve a circulating concentration range that includes an IC50 as determined in cell culture against activation, proliferation, cytokine production, and/or perforin production by $T_{EM}$. Such information can be used to more accurately determine useful doses in subjects of interest.

The actual amount administered to a particular subject as a therapeutically effective amount can be determined by a physician, veterinarian, or researcher taking into account parameters such as physical and physiological factors including target, body weight, severity of condition, type of ophthalmic condition, previous or concurrent therapeutic interventions, idiopathy of the subject, and route of administration.

Dosage may be adjusted appropriately to achieve desired toxin-based therapeutic peptide levels, locally or systemically. Typically the toxin-based therapeutic peptides of the present disclosure exhibit their effect at a dosage range from 0.001 mg/kg to 250 mg/kg, preferably from 0.01 mg/kg to 100 mg/kg of the toxin-based therapeutic peptide, more preferably from 0.05 mg/kg to 75 mg/kg. A suitable dose can be administered in multiple sub-doses per day. Typically, a dose or sub-dose may contain from 0.1 mg to 500 mg of the toxin-based therapeutic peptide per unit dosage form. A more preferred dosage will contain from 0.5 mg to 100 mg of toxin-based therapeutic peptide per unit dosage form.

Additional useful doses often range of 0.001 to 10,000 micrograms (μg) of the toxin-based therapeutic peptide per kilogram (kg) of body mass, in the range of 1 to 5,000 μg/kg of body mass, in the range of 1 to 1,000 μg/kg of body mass or in the range of 1 to 100 μg/kg of body mass. Often, doses may range from 0.1 to 5 μg/kg or from 0.5 to 1 μg/kg. In other examples, a dose can include 1 μg/kg, 5 μg/kg, 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 μg/kg, 100 μg/kg, 150 μg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1,000 μg/kg, 1,500 μg/kg, 2,000 μg/kg, 2,500 μg/kg, 3,000 μg/kg, 3,500 μg/kg, 4,000 μg/kg, 5,000 μg/kg, 6,000 μg/kg, 7,000 μg/kg, 8,000 μg/kg, 9,000 μg/kg, 10,000 μg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, or 50 mg/kg.

When cocktails are used, a common administration vehicle (e.g., pill, tablet, implant, pump, injectable solution, etc.) can contain both the toxin-based therapeutic peptides in combination with the other drugs or agents. The individual components of the cocktail can each be administered in therapeutically effective amounts or their administration in combination can create a therapeutically effective amount.

In particular embodiments, dosages can be initiated at lower levels and increased until desired effects are achieved. In the event that the response in a subject is insufficient at such doses, even higher doses (or effective higher doses by a different, more localized delivery route) may be employed to the extent that subject tolerance permits. Continuous dosing over, for example, 24 hours or multiple doses per day are contemplated to achieve appropriate systemic or tissue-specific levels of toxin-based therapeutic peptide.

Therapeutically effective amounts can be achieved by administering single or multiple doses during the course of a treatment regimen (e.g., daily, twice-daily, thrice-daily, four times daily, five times daily, six times daily, seven times daily, eight times daily, nine times daily, ten times daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 month, or yearly.

The pharmaceutical composition may be administered in conjunction with one or more systemic or topical products that alleviate symptoms of ophthalmic conditions such as artificial tears, antibiotics, cyclosporine, or corticosteroids.

A variety of administration routes are available. The particular mode selected can depend upon the particular pharmaceutical composition delivered, the severity of the ophthalmic condition being treated, and the dosage required to provide a therapeutically effective amount. Any mode of administration that is medically acceptable, meaning any mode that provides a therapeutically effective amount of the toxin-based therapeutic peptide without causing clinically unacceptable adverse effects that outweigh the benefits of administration according to sound medical judgment can be used. Exemplary routes of administration include intraarterial, intradermal, intralesional, intralymphatic, intramuscular, intranasal, intranodal, intraocular, intraparenteral, intraperitoneal, intraprostatic, intrarectal, intrathecal, intratumoral, intravaginal, intravenous, intravesicular, intravitreal, oral, subcutaneous, sublingual, and/or topical, administration and more particularly by intraarterial, intradermal, intralesional, intralymphatic, intramuscular, intranasal, intranodal, intraocular, intraparenteral, intraperitoneal, intraprostatic, intrarectal, intrathecal, intratumoral, intravaginal, intravenous, intravesicular, intravitreal, oral, subcutaneous, and/or sublingual injection.

Pharmaceutical compositions can be delivered topically to the eye and adnexa, as eye drops, subconjunctival implants, intraocular implants, intraocular injections, intravitreal injections, intravitreal implants, sub-Tenon's capsule injections and in punctual plugs. Delivery of the pharmaceutical compositions can also be facilitated by ultrasound or iontophoresis.

For administration of the pharmaceutical composition, a suitable route is injection. A medical practitioner will be familiar with methods of administration through injection depending on the subject and the type of injection, such as subcutaneous, intravenous, etc. U.S. Pat. No. 7,918,824 discloses syringes suitable for subject use.

Administration of the toxin-based therapeutic peptides can also be achieved using pumps (see, e.g., Luer et al., The Annals of Pharmacotherapy, 27, 912 (1993), Zimm et al., Cancer Research, 44, 1698 (1984) and Ettinger et al., Cancer, 41, 1270 (1978)).

Alternatively, targeting therapies may be used to deliver the toxin-based therapeutic peptide more specifically to certain types of cell, by the use of targeting systems such as antibodies or cell specific ligands.

Pharmaceutical compositions can also be administered in a cell based delivery system in which a nucleotide sequence encoding the toxin-based therapeutic peptide is introduced into cells designed for implantation in the body of the subject, for example, in the eye. In other embodiments, the nucleotide sequence can be administered and transfected into a subject's cells.

Suitable nucleotide sequences can be prepared synthetically for each toxin-based therapeutic peptide on the basis of the disclosed sequences and the known genetic code. Briefly, the term "gene" refers to a nucleic acid sequence that encodes a toxin-based therapeutic peptide. This definition includes various sequence polymorphisms, mutations, and/or sequence variants wherein such alterations do not affect the function of the encoded toxin-based therapeutic peptide. The term "gene" may include not only coding sequences but also regulatory regions such as promoters, enhancers, and termination regions. The term further can include all introns and other DNA sequences spliced from the mRNA transcript, along with variants resulting from alternative splice sites. Nucleic acid sequences encoding the toxin-based therapeutic peptide can be DNA or RNA that directs the expression of the toxin-based therapeutic peptide. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Gene sequences to encode toxin-based therapeutic peptide disclosed herein are available in publicly available databases and publications.

In some embodiments, the polynucleotide includes a plasmid, a cDNA, or an mRNA that can include, e.g., a sequence (e.g., a gene) for expressing a toxin-based therapeutic peptide. Suitable plasmids include standard plasmid vectors and minicircle plasmids that can be used to transfer a gene to a cell. The polynucleotides (e.g., minicircle plasmids) can further include any additional sequence information to facilitate transfer of the genetic material (e.g., a sequence encoding a toxin-based therapeutic peptide) to a cell. For example, the polynucleotides can include promoters, such as general promoters, tissue-specific promoters, cell-specific promoters, and/or promoters specific for the nucleus or cytoplasm. Promoters and plasmids (e.g., minicircle plasmids) are generally well known in the art and can be prepared using conventional techniques. As described further herein, the polynucleotides can be used to transfect cells. Unless otherwise specified, the terms transfect, transfected, or transfecting can be used to indicate the presence of exogenous polynucleotides or the expressed peptide therefrom in a cell. A number of vectors are known to be capable of mediating transfer of genes to cells, as is known in the art.

In particular embodiments, this delivery method can be used in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959, and WO 97/12635.

The present disclosure also provides methods of screening subjects with dry eye or other ophthalmic conditions to assess the potential therapeutic benefit of the methods disclosed herein in the screened subjects. In one embodiment, levels of expression of Kv1.3 channels in the subject's T-cell populations are assessed using an antibody that detects surface expression of the channel. An anti-potassium channel Kv1.3 (extracellular) antibody to practice these methods is available from Alomone (Israel); antibodies are also available from LifeSpan Biosciences, Inc. (Seattle, Wash., USA). Kv1.3 channel levels can be indicative of an ophthalmic condition that can be effectively treated with the toxin-based therapeutic peptides disclosed herein.

To identify subjects that will benefit from the methods disclosed herein, the subject's Kv1.3 channel levels are compared to a reference level obtained from a dataset. A reference level from a dataset can be derived from previous measures in the same subject or can be derived from a population. A "population" is any grouping of subjects of like specified characteristics. The grouping could be according to, for example, clinical parameters, clinical assessments, therapeutic regimens, disease status (healthy or having an ophthalmic condition disclosed herein), severity of ophthalmic condition, etc.

A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual datapoints; e.g., mean, median, median of the mean, etc. Alternatively, a reference level or dataset to create a reference level can be obtained from a service provider such as a laboratory, or from a database or a server on which the dataset has been stored.

In particular embodiments, a subject can be selected as one who will benefit from the treatments disclosed herein based on Kv1.3 channel levels that are not statistically significantly different from a reference level from a population that previously benefited from the disclosed treatments. In additional embodiments, a subject can be selected as one who will benefit from the treatments disclosed herein based on Kv1.3 channel levels that are not statistically significantly different from a reference level from population having an ophthalmic condition disclosed herein. In further particular embodiments, a subject can be selected as one who will benefit from the treatments disclosed herein based on Kv1.3 channel levels that are statistically significantly higher over a reference level from a healthy population.

Kv1.3 channel levels are not significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered significant (not random chance) at a p-value less than or equal to 0.05.

The described screening methods can be used to direct a subject's treatment. For example, if the subject's Kv1.3 channel levels identify the subject as one who would benefit from the methods disclosed herein, the subject can be prescribed or given a therapeutically effective amount of a pharmaceutical composition disclosed herein. The results of the screening methods can also be used to, for example, provide clinical decision support, such as determining whether to defer intervention or treatment, to recommend preventive check-ups for at-risk patients, to recommend increased visit frequency, to recommend increased testing, and/or to recommend intervention. The results of the methods can also be useful for therapeutic selection, determining response to treatment, adjustment and dosing of treatment, monitoring ongoing therapeutic efficiency, and indication for change in therapeutic regimens.

Methods of Manufacture

The toxin-based therapeutic peptides can be prepared using recombinant DNA technology. Toxin-based therapeutic peptides may also be prepared using the Merrifield solid-phase synthesis, although other equivalent chemical syntheses known in the art can also be used. Solid-phase synthesis is commenced from the C-terminus of the toxin-based therapeutic peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or para-methylbenzhydrylamine (MBNA) resin. Preparation of the hydroxymethyl resin is described by Bodansky et al., Chem. Ind. (London) 38, 1597 (1966). Chloromethylated resins are commercially available from Bio Rad Laboratories (Richmond, Calif.) and from Lab. Systems, Inc. The preparation of such a resin is described by Stewart & Young, Solid phase peptide synthesis. W.H. Freeman, Kent, England (1969). BHA and MBHA resin supports are commercially available, and are generally used when the desired toxin-based therapeutic peptide being synthesized has an unsubstituted amide at the C-terminus. Thus, solid resin supports may be any of those known in the art, such as one having the formulae —O—CH$_2$-resin support, —NH BHA resin support, or —NH-MBHA resin support. When the unsubstituted amide is desired, use of a BHA or MBHA resin can be advantageous because cleavage directly gives the amide. In case the N-methyl amide is desired, it can be generated from an N-methyl BHA resin. Should other substituted amides be desired, the teaching of U.S. Pat. No. 4,569,967 can be used, or should still other groups than the free acid be desired at the C-terminus, it may be preferable to synthesize the toxin-based therapeutic peptide using classical methods as set forth in Houben & Weyl, Methoden der organischen Chemie, Georg Theime, Stuttgart (1974).

The C-terminal amino acid, protected by Boc or Fmoc and by a side-chain protecting group, if appropriate, can be first coupled to a chloromethylated resin according to the procedure set forth in Horiki et al., Chem. Lett., 165-168, (1978) using KF in dimethylformamide (DMF) at about 60° C. for 24 hours with stirring, when a toxin-based therapeutic peptide having free acid at the C-terminus is to be synthesized. Following the coupling of the BOC-protected amino acid to the resin support, the α-amino protecting group can be removed, as by using trifluoroacetic acid (TFA) in methylene chloride or TFA alone. The deprotection can be carried out at a temperature between 0° C. and room temperature. Other standard cleaving reagents, such as HCl in dioxane, and conditions for removal of specific α-amino protecting groups may be used as described in Schroeder & Lubke, The Peptides, Academic Press: New York (1965).

After removal of the α-amino-protecting group, the remaining α-amino- and side chain-protected amino acids can be coupled step-wise in the desired order to obtain an intermediate compound or as an alternative to adding each amino acid separately in the synthesis, some of them may be coupled to one another prior to addition to the solid phase reactor. Selection of an appropriate coupling reagent is within the skill of the art. Exemplary coupling reagents include N,N'-dicyclohexylcarbodiimide (DCC, DIC, HBTU, HATU, TBTU in the presence of HoBt or HoAt).

The activating reagents used in the solid phase synthesis of peptides including toxin-based therapeutic peptides are well known in the art. Examples of suitable activating reagents include carbodiimides, such as N,N'-diisopropylcarbodiimide and N-ethyl-N'-(3-dimethylaminopropyl)carbodiimide. Other activating reagents and their use in peptide coupling are described by Schroeder & Lubke, The Peptides, Academic Press: New York (1965) and Kapoor, J. Pharm. Sci., 59(1), 1-27 (1970).

Each protected amino acid or amino acid sequence can be introduced into the solid-phase reactor in a twofold or more excess, and the coupling may be carried out in a medium of DMF:CH$_2$Cl$_2$ (1:1) or in DMF or CH$_2$Cl$_2$ alone. In cases where intermediate coupling occurs, the coupling procedure can be repeated before removal of the α-amino protecting group prior to the coupling of the next amino acid. The success of the coupling reaction at each stage of the synthesis, if performed manually, can be monitored by the ninhydrin reaction, as described by Kaiser et al., Anal. Biochem. Vol 34(2), 595-8 (1970).

Coupling reactions can be performed automatically, as on a Beckman 990 automatic synthesizer, using a program such as that reported in Rivier et al., Biopolymers, 17(8), 1927-1938 (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group can be first removed using TFA/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide can be included in the reaction vessel.

Cyclization of the linear toxin-based therapeutic peptide can be affected, as opposed to cyclizing the toxin-based therapeutic peptide while a part of the peptido-resin, to create bonds between Cys residues. To effect such a disulfide cyclizing linkage, a fully protected toxin-based therapeutic peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the toxin-based therapeutic peptide from the above resins or a benzhydrylamine (BHA) resin or a methylbenzhydrylamine (MBHA), can take place at 0° C. with hydrofluoric acid (HF) or TFA, followed by oxidation as described above.

The toxin-based therapeutic peptides can also be synthesized using an automatic synthesizer. In these embodiments, amino acids can be sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluorophosphate (HBTU) and diethylisopropylethylamine (DIEA). The Fmoc protecting group can be removed by treatment with a 20% solution of piperidine in dimethylformamide (DMF). Resins are subsequently washed with DMF (twice), followed by methanol and NMP.

Exemplary Embodiments

1. A method of treating an ophthalmic condition in a subject in need thereof including administering to the subject a therapeutically effective amount of a pharmaceutical composition including a toxin-based therapeutic peptide having at least 80% sequence identity to any of SEQ ID NOs:1-256.
2. A method of embodiment 1, wherein the toxin-based therapeutic peptide has at least 85% sequence identity to any of SEQ ID NOs:1-256.
3. A method of embodiments 1 or 2, wherein the toxin-based therapeutic peptide has at least 90% sequence identity to any of SEQ ID NOs:1-256.
4. A method of any of embodiments 1-3, wherein the toxin-based therapeutic peptide has at least 95% sequence identity to any of SEQ ID NOs:1-256.
5. A method of any of embodiments 1-4, wherein the toxin-based therapeutic peptide has at least 96% sequence identity to any of SEQ ID NOs:1-256.
6. A method of any of embodiments 1-5, wherein the toxin-based therapeutic peptide has at least 97% sequence identity to any of SEQ ID NOs:1-256.
7. A method of any of embodiments 1-6, wherein the toxin-based therapeutic peptide has at least 98% sequence identity to any of SEQ ID NOs:1-256.
8. A method of any of embodiments 1-7, wherein the toxin-based therapeutic peptide has at least 99% sequence identity to any of SEQ ID NOs:1-256.
9. A method of embodiment 1, wherein the toxin-based therapeutic peptide is a toxin-based peptide having at least 80% sequence identity to any of SEQ ID NOs:225-256.
10. A method of embodiment 9, wherein the toxin-based peptide has at least 85% sequence identity to any of SEQ ID NOs:225-256.
11. A method of embodiments 9 or 10, wherein the toxin-based peptide has at least 90% sequence identity to any of SEQ ID NOs:225-256.
12. A method of any of embodiments 9-11, wherein the toxin-based peptide has at least 95% sequence identity to any of SEQ ID NOs:225-256.
13. A method of any of embodiments 9-12, wherein the toxin-based peptide has at least 96% sequence identity to any of SEQ ID NOs:225-256.
14. A method of any of embodiments 9-13, wherein the toxin-based peptide has at least 97% sequence identity to any of SEQ ID NOs:225-256.
15. A method of any of embodiments 9-14, wherein the toxin-based peptide has at least 98% sequence identity to any of SEQ ID NOs:225-256.
16. A method of any of embodiments 9-15, wherein the toxin-based peptide has at least 99% sequence identity to any of SEQ ID NOs:225-256.
17. A method of embodiment 1, wherein the toxin-based therapeutic peptide is an ShK-based peptide having at least 80% sequence identity to any of SEQ ID NOs:1-224.
18. A method of embodiment 17, wherein the ShK-based peptide has at least 85% sequence identity to any one of SEQ ID NOs:1-224.
19. A method of embodiments 17 or 18, wherein the ShK-based peptide has at least 90% sequence identity to any one of SEQ ID NOs:1-224.
20. A method of any one of embodiments 17-19, wherein the ShK-based peptide has at least 95% sequence identity to any one of SEQ ID NOs:1-224.
21. A method of any one of embodiments 17-20, wherein the ShK-based peptide has at least 96% sequence identity to any one of SEQ ID NOs:1-224.
22. A method of any one of embodiments 17-21, wherein the ShK-based peptide has at least 97% sequence identity to any one of SEQ ID NOs:1-224.
23. A method of any one of embodiments 17-22, wherein the ShK-based peptide has at least 98% sequence identity to any one of SEQ ID NOs:1-224.
24. A method of any one of embodiments 17-23, wherein the ShK-based peptide has at least 99% sequence identity to any one of SEQ ID NOs:1-224.
25. A method of any one of embodiments 1 and 17-20, wherein the ShK-based peptide has at least 95% sequence identity to SEQ ID NO:1.
26. A method of any one of embodiments 1 and 17-20, wherein the ShK-based peptide has at least 95% sequence identity to SEQ ID NO:2.
27. A method of any one of embodiments 1 and 17-20, wherein the ShK-based peptide has at least 95% sequence identity to SEQ ID NO:208, SEQ ID NO:209, SEQ ID NO:210, SEQ ID NO:217, and/or SEQ ID NO:218.
28. A method of any one of embodiments 1, 17-20, and 27, wherein the ShK-based peptide has at least 96% sequence identity to SEQ ID NO:208, SEQ ID NO:209, SEQ ID NO:210, SEQ ID NO:217, and/or SEQ ID NO:218.
29. A method of any one of embodiments 1, 17-20, 27, and 28, wherein the ShK-based peptide has at least 97% sequence identity to SEQ ID NO:208, SEQ ID NO:209, SEQ ID NO:210, SEQ ID NO:217, and/or SEQ ID NO:218.
30. A method of any one of embodiments 1, 17-20, and 27-29, wherein the ShK-based peptide has at least 98% sequence identity to SEQ ID NO:208, SEQ ID NO:209, SEQ ID NO:210, SEQ ID NO:217, and/or SEQ ID NO:218.
31. A method of any one of embodiments 1, 17-20, and 27-30, wherein the ShK-based peptide has at least 99% sequence identity to SEQ ID NO:208, SEQ ID NO:209, SEQ ID NO:210, SEQ ID NO:217, and/or SEQ ID NO:218.
32. A method of any one of embodiments 1-31, wherein the toxin-based therapeutic peptide is natural or synthetic.
33. A method of any one of embodiments 1-32, wherein the toxin-based therapeutic peptide is attached to an organic or inorganic chemical entity that has an anionic charge.
34. A method of any one of embodiments 1-33, wherein the C-terminus of the toxin-based therapeutic peptide is an acid or an amide.
35. A method of any one of embodiments 1-34, wherein the pharmaceutical composition is administered topically to the eye.
36. A method of any one of embodiments 1-35, wherein the pharmaceutical composition is administered by a parenteral and/or enteral route.
37. A method of any one of embodiments 1-36, wherein the pharmaceutical composition is administered topically and by a parenteral and/or enteral route.
38. A method of any one of embodiments 1-37, wherein the pharmaceutical composition is administered through intravitreal injection.
39. A method of any one of embodiments 1-38, wherein the pharmaceutical composition is administered six times daily, five times daily, four times daily, three times daily, twice daily, daily, weekly, monthly, every two months, every three months, or every six months.
40. A method of any one of embodiments 1-39, wherein the ophthalmic condition is dry eye, uveitis, pediatric uveitis, keratoconjunctivitis sicca, episcleritis, keratitis, retinal vasculitis, scleritis, endophthalmitis, cicatricial pemphigoid, Mooren's ulcer, and/or cytomegalovirus-mediated retinitis.

41. A method of any one of embodiments 1-40, wherein the ophthalmic condition is caused by systemic lupus erythematous, microscopic polyangiitis, polyarteritis nodosa, Wegener's granulomatosis (granulomatosis with polyangitis), sarcoidosis, Behçet's syndrome, Vogt-Koyanagi-Harada disease, Takayasu's arteritis, rheumatoid arthritis, Sjorgen's syndrome, relapsing polychondritis, ankylosing spondylitis, psoriasis, and/or Churg-Strauss syndrome.

42. A method of any one of embodiments 1-41, wherein the subject is a human adult, child or adolescent.

43. A method of any one of embodiments 1-42, wherein the pharmaceutical composition includes a preservative.

44. A method of embodiment 43, wherein the preservative is benzalkonium chloride (≤0.025%), scorbic acid, benzethonium chloride (≤0.01%), chlorobutanol (≤0.5%), phenylmercuric acetate (≤0.004%), phenylmercuric nitrate (≤0.004%), thimerosal (≤0.01%), methylparaben (0.1-0.2%), and/or propylparabens (≤0.04%).

45. A method of any one of embodiments 1-44, wherein the pharmaceutical composition includes a viscosity enhancer.

46. A method of embodiment 45, wherein the viscosity enhancer is carboxymethylcellulose (≤1%), hydroxyethylcellulose (≤0.8%), hydroxypropylmethylcellulose (≤1%), methylcellulose (≤2%), polyvinyl alcohol (≤1.4%), polycarbophil, gellan gum, xanthan gum, carbopol, poly(styrene-divinyl benzene) sulfonic acid, and/or polyvinylpyrrolidine (≤1.7%).

47. A method of any one of embodiments 1-46, wherein the pharmaceutical composition includes an antioxidant.

48. A method of embodiment 47, wherein the antioxidant is ethylenediaminetetraacetic acid (≤0.1%), sodium bisulfite (≤0.1%), sodium metabisulfite (≤0.1%), and/or thiourea (≤0.1%).

49. A method of any one of embodiments 1-48, wherein the pharmaceutical composition includes a buffering agent, a tonicity modifier, and a surfactant.

50. A method of any one of embodiments 1-49, wherein the pharmaceutical composition includes 10 mM sodium phosphate; 0.8% w/v NaCl; and Polysorbate 20 at 0.01, 0.05, 0.1, 0.2, 0.4, 0.6, 0.8, 1, 2, 3, or 4 w/v %, wherein the composition has a pH of 5.0, 5.5, 6.0, 6.5, 7, 7.5, or 8.

51. A method of any one of embodiments 1-50, wherein the pharmaceutical composition includes Polysorbate 20 at 0.05 w/v %, and wherein the composition has a pH of 6.0.

52. A method of any one of embodiments 1-49, wherein the pharmaceutical composition includes 10 mM sodium phosphate; 0.8% w/v NaCl; and Polysorbate 80 at 0.01, 0.05, 0.1, 0.2, 0.4, 0.6, 0.8, 1, 2, 3, or 4 w/v %, wherein the composition has a pH of 5.0, 5.5, 6.0, 6.5, 7, 7.5, or 8.

53. A method of any one of embodiments 1-49 or 52, wherein the pharmaceutical composition includes Polysorbate 80 at 0.05 w/v %, and wherein the composition has a pH of 6.0.

54. A method of any one of embodiments 1-53, wherein the therapeutically effective amount increases tear formation; decreases the sensation of stinging or burning of the eye; decreases the production of a stringy discharge from the eye; reduces pain in the eye; reduces redness of the eye; reduces the frequency and/or duration of episodes of blurred vision; decreases light sensitivity; decreases the frequency and/or duration of episodes of dark, floating spots in the subject's field of vision; increases the subject's vision; decreases the sensation of grittiness in the eye; decreases the sensation of heavy eyelids; decreases episodes of excess tears following very dry eye periods; and/or decreases whitish area(s) inside the eye in the front of the iris.

55. A method of evaluating a subject to predict the outcome of treatment with a method of any one of embodiments 1-54 including: analyzing Kv1.3 channel expression levels of T-cells from a biological sample of the subject; wherein increased levels of Kv1.3 channel expression relative to a healthy control or reference population is indicative of a patient receptive to treatment with an ShK-based peptide having at least 80% sequence identity to any one of SEQ ID NOs:1-224.

56. A method of screening for subjects who may benefit from treatment with a method of any one of embodiments 1-54 including: measuring Kv1.3 channel expression levels of T-cells and/or macrophages from a biological sample of the subject; comparing Kv1.3 channel expression levels of the subject to that of a healthy control or reference population; and determining that the subject will benefit from treatment with a method of any one of embodiments 1-54 if the level of Kv1.3 channel expression in the subject is increased compared to the healthy control or reference population.

57. A method of selecting subjects for a clinical trial including: measuring Kv1.3 channel expression levels of T-cells and/or macrophages from a biological sample of the subject; comparing Kv1.3 channel expression levels of the subject to that of a healthy control or reference population; and selecting the subject for the clinical trial if the subject has increased Kv1.3 channel expression levels compared to the healthy control or reference population, or excluding the subject from the clinical trial if the subject has decreased or unchanged Kv1.3 channel expression levels compared to the healthy control or reference population.

58. A method for screening potential treatments for ophthalmic conditions in a subject including: measuring Kv1.3 channel expression levels of T-cells and/or macrophages from a biological sample of the subject; comparing Kv1.3 channel expression levels of the subject to that of a healthy control or reference population; and identifying any one of the methods of embodiments 1-54 as a treatment for the subject if the subject has increased Kv1.3 channel expression levels compared to the healthy control or reference population.

59. A method of any one of embodiments 56-58, wherein the Kv1.3 channel expression level is measured using an assay.

60. A method of embodiment 55, wherein the Kv1.3 channel expression level is analyzed using an assay.

61. A method of any one of embodiments 55-60, further including challenging the T-cells with a proinflammatory immune stimulator or T-cell activating agent in the presence of a toxin-based therapeutic peptide.

62. A method of embodiment 61, wherein the toxin-based therapeutic peptide is an ShK-based peptide.

63. A method of embodiment 62, wherein the ShK-based peptide has at least 95% sequence identity to SEQ ID NO: 1, SEQ ID NO:2, SEQ ID NO:208, SEQ ID NO:209, SEQ ID NO:210, SEQ ID NO:217, and/or SEQ ID NO:218.

64. A method of any one of embodiments 55-63, further including measuring proinflammatory cytokine production.

65. A method of embodiment 64, wherein the measured cytokine is Interferon (IFN)-γ, Interleukin (IL)-1a, IL-1b, IL-2, IL-4, IL-6, IL-7, IL-8, IL-10, IL-15, IL-17A, IL-17F, IL-17A/F, IL-21, IL-22, IL-23, Granulocyte macrophage colony-stimulating factor (GM-CSF), Tumor necrosis factor (TNF)-α, metalloprotease (MMP)3, and/or MMP9.

66. A method of any one of embodiments 55-65, further including challenging the T-cells with ocular antigens in the presence or absence of a toxin-based therapeutic peptide.
67. A method of embodiment 66, wherein the toxin-based therapeutic peptide is an ShK-based peptide.
68. A method of embodiment 67, wherein the ShK-based peptide has at least 95% sequence identity to SEQ ID NO: 1, SEQ ID NO:2, SEQ ID NO:208, SEQ ID NO:209, SEQ ID NO:210, SEQ ID NO:217, and/or SEQ ID NO:218.
69. A method of embodiment 68, wherein the ShK-based peptide has the formula SEQ ID NO:217.
70. An exemplary embodiment of any one of embodiments 1-69, wherein the ophthalmic condition is an inflammatory ophthalmic condition.

The Examples below describe the optimization of the methods disclosed herein. These Examples are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

EXAMPLES

Example 1. Suppression of Inflammatory Cytokine Production by Toxin-Based Therapeutic Peptides This Example describes the assessment of whether a toxin-based therapeutic peptide as disclosed herein would modulate the level of cytokines that contribute to tissue damage and inflammation related to ophthalmic conditions.

Th17 cells, which produce the cytokines IL-17-A, -F, -A/F, IL-21, and IL22, as well as Th1/Th17 cells, which produce IL-17-A, -F, -NF, and IFN-γ are increasingly implicated in the pathogenesis of various autoimmune disorders including autoimmune disorders affecting the eyes, such as various forms of uveitis, as well as dry eye disease. Similar to IFN-γ, by increasing chemokine production, IL-17 leads to recruitment of monocytes/macrophages and neutrophils to the site of inflammation. Early sources of IL-17 include γδ T cells, which are resident in ocular surface tissues, and natural killer (NK) T-cells, which accumulate in the ocular surface tissues, such as the conjunctiva during early stages of desiccating stress-induced dry eye. NK T-cells are also an early source of the IFN-γ that is associated with reduced goblet density, altered corneal epithelial mucins, and cornea epithelial barrier dysfunction.

CD4+ Th1, Th17, and Th1/Th17 T-cells play a primary role in the tissue damage during the antigen-specific chronic stages of dry eye and other ophthalmic conditions. Activated CD4+ T-cells are localized on the ocular surface of dry eye patients and are responsible for progression of the disease. Together, Th1 and Th17-derived cytokines are responsible for much of the tissue damage in dry eye and other ophthalmic conditions and are suitable targets for treating the symptoms and the underlying pathological processes of these conditions in humans. This includes various forms of uveitis including chronic uveitis such as that seen in Juvenile Idiopathic Arthritis, Sjogren's syndrome, and Behcet's syndrome, in which IFN-γ and IL-17 are both associated with increased inflammation and glandular dysfunction. Thus, a common mechanism in localized and systemic causes of dry eye and uveitis can be targeted for therapy using the methods and pharmaceutical compositions disclosed herein.

This Example explores the ability of pharmaceutical compositions including toxin-based therapeutic peptides disclosed herein to reduce pro-inflammatory cytokine secretion caused by thapsigargin (Sigma-Aldrich, St. Louis, Mo., USA). Thapsigargin stimulates proinflammatory cytokine release by inhibiting the Ca2+ ion pump proteins of intracellular membranes in the sarcoplasmic reticulum and endoplasmic reticulum of microsomes. This inhibition results in a rapid release of Ca2+ stores and subsequent activation of plasma membrane calcium channels.

Preparation of primary blood cells. Whole blood and peripheral blood mononuclear cells (PBMCs) were used to test the suitability of an ShK-based therapeutic peptide as disclosed herein for treating a subject with an ophthalmic condition including dry eye. Whole blood was directly aliquoted to cell culture for experimental assays without any additional processing.

PBMCs were isolated from donor blood by density gradient centrifugation as follows. Blood was collected in collection tubes containing sodium heparin as an anticoagulant and a cell separation medium including a polyester gel and a density gradient liquid (BD Vacutainer CPT). The samples were centrifuged at 1500 RCF for 20 minutes at room temperature. The cell layer containing mononuclear cells and platelets lies just below the plasma layer and was collected into a separate 15 mL conical tube using a Pasteur Pipette. The cells were washed twice with PBS and pelleted by centrifugation to remove the supernatant. The purified PBMCs were resuspended in complete RPMI (cRPMI) cell culture media and plated to the appropriate density for the assay.

Other cells from which cytokine secretion could be measured include human macrophages/monocytes, rat blood cells, lymph nodes, and splenocytes.

Treatment of primary blood cells. ShK-186 was serially diluted in cRPMI to 4× final concentration working stock. 50 µL of working stock was added to 6 wells of a 96-well cell culture plate per concentration of ShK-based peptide. 50 µL of cRPMI without ShK-based peptide was used as control treatment in positive control (no ShK-based peptide, thapsigargin stimulus) and in negative control (no ShK-based peptide, no thapsigargin stimulus) wells. 100 µL whole blood or 200,000 PBMCs in complete RPMI was added to each well of the 96-well cell culture plate. Cells with ShK-based peptide or media control were incubated at 37° C. and 5% $CO_2$ for one hour. After one hour, 50 µL of 40 uM thapsigargin stimulus was added to all wells except for negative control wells which received 50 µL 0.4% DMSO to 0.1% final concentration. Cells were incubated for 48 hours.

Analysis of ShK-based peptide treated and thapsigargin stimulated cells. 48 hours after stimulation by thapsigargin, 96-well plates were centrifuged at 2000 RPM for 5 minutes. The supernatant was carefully transferred to a sterile 96-well plate for sample analysis. Cytokines were detected using specific antibodies conjugated to magnetic beads and a secondary antibody that reacts with Streptavidin/Phycoerythrin to produce a fluorescent signal. The bound beads were detected and quantified using the Magpix instrument (Luminex Corp., Austin, Tex., USA), although similar techniques as are known in the art may be used to measure protein production, such as for example an ELISA, using methods of detection including fluorescent and colorimetric methods.

Using the methods described above, ShK-186 (SEQ ID NO:217) was demonstrated to suppress inflammatory cytokines that have been shown to contribute to dry eye, including IL-17, and IFN-γ. ShK-186 suppressed the levels of inflammatory cytokines IL-2, IL-17, IL-4, and IFN-γ in whole blood treated with ShK-186 prior to stimulation with thapsigargin. The IC50 values were in the picomolar range, as shown in FIG. 1.

Figure 2:
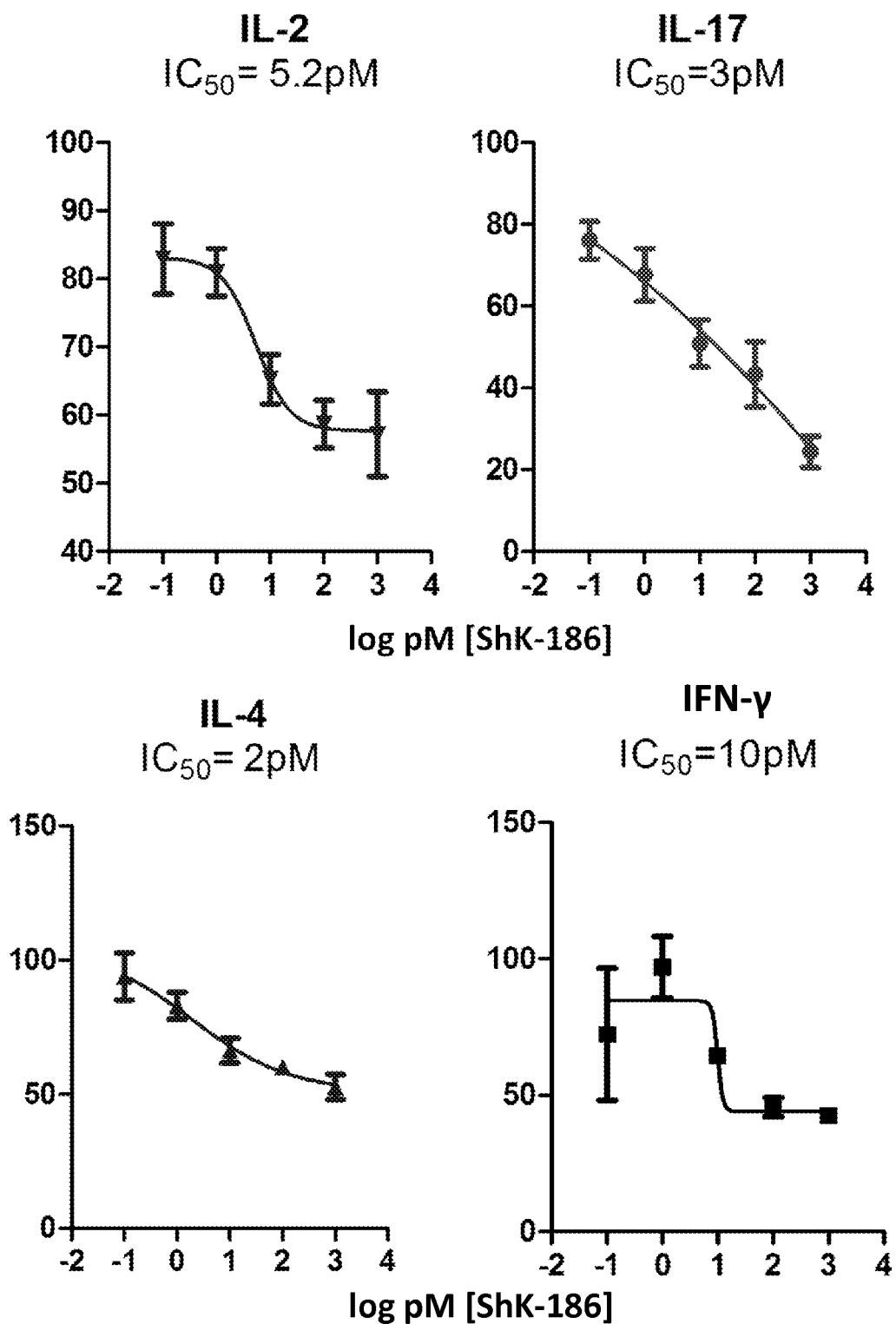
FIG. 2 provides a series of four graphs showing the effect of ShK-186 on inflammatory cytokine levels in human peripheral blood mononuclear cells (PBMCs) stimulated with thapsigargin. ShK-186 suppressed the inflammatory cytokines IL-2, IL-17, IL-4, and IFN-γ in a dose-dependent manner.

ShK-186 also suppressed the levels of inflammatory cytokines IL-2, IL-17, IL-4, and IFN-γ in PBMCs treated with ShK-186 prior to stimulation with thapsigargin. The 1050 values were in the picomolar range, as shown in FIG. 2.

These results demonstrate that the pharmaceutical compositions including ShK-based therapeutic peptides disclosed herein can reduce the secretion of proinflammatory cytokines associated with ophthalmic conditions such as autoimmune eye disease including uveitis and dry eye.

Example 2. Expression of Kv1.3 Channels by $T_{EM}$ in Dry Eye and Control Patients This example describes the evaluation of Kv1.3 channel expression by $T_{EM}$ found in dry eye patients compared to those from healthy patient controls, and to characterize the responsiveness of dry eye patient samples to treatment with a toxin-based therapeutic peptide of the disclosure, such as ShK-186.

In order to carry out functional assays, PBMCs from uveitis or dry eye patients and healthy controls are isolated. In the first phase of the example, the cells are either tested shortly after activation without ex vivo stimulation or activated ex vivo with anti-CD3 and anti-CD28 antibodies or mitogens and then subjected to immunostaining and multicolor flow cytometry to study expression levels of Kv1.3 channel on the surface of $T_{EM}$ within the CD4 and CD8+ T-cell subsets. Cells isolated from patients are expected to be high in expression of Kv1.3 without stimulation ex vivo, but this expression could increase upon activation ex vivo. To validate Kv1.3 as a therapeutic target, conjunctival biopsy specimens from dry eye or uveitis patients are subjected to immunohistochemistry by staining with anti-CD3+, -CD4+, and -Kv1.3 antibodies in order to identify CD3+/CD4+ T-cell populations that express elevated levels of Kv1.3. Similarly, antibodies to CD40, CD68, CD163, iNOS and others and in combination with anti-Kv1.3 antibody can be used to identify activated macrophages. Samples from patients suffering from dry eye or other autoimmune eye diseases such as chronic uveitis are expected to be positive for activation markers and Kv1.3 high T cells and macrophages. In the third phase, matching cell aliquots are used to study the ability of a ShK-based peptide to block the proinflammatory and proliferative potential of $T_{EM}$ from dry-eye patients or uveitis patients versus controls. Cytokines including IFN-γ, IL-2, IL-4, IL-10, IL-17, IL-21, and IL-22, perforin, and granzyme B are detected by intracellular staining and flow cytometry in resting or activated cells in the presence or absence of toxin-based therapeutic peptide. Additionally, they can be quantitated by an assay such as multiplexing ELISA of collected supernatants. In these experiments, ex vivo addition of ShK-186 significantly reduces expression of the aforementioned cytokines as determined by one or any of the methods described in both unstimulated or activated T cells or macrophages. Addition of ShK-186 likewise significantly reduces the ex vivo proliferation of T cells or macrophages during ex vivo activation. This reduction can be measured by quantification of [$^3$H] thymidine incorporation or the fluorescent dye CFSE, among other standard immunological methods.

Example 3. Localized Delivery of Toxin-Based Therapeutic Peptides by Topical Administration This example describes the evaluation of localized and systemic drug levels after administration of a toxin-based therapeutic peptide of the disclosure, such as ShK-186 or ShK-198.

Three female 6-8 week old Sprague-Dawley rats (Indianapolis, Ind., USA) were dosed three times per day with topically administered 10 μL of P6N (sodium phosphate (10 mM), sodium chloride (0.8%), and Polysorbate 20 (0.05%) at pH 6.0) on the left eye (LE) and 10 μL of 0.5% ShK-186 in P6N on the right eye (RE) for 21 days. Blood was collected at 3, 7, 12, 14, 17, and 21 days and processed to plasma. At 21 days, the vitreous fluid was collected from each eye in addition to plasma. ShK-186 levels in collected samples were measured using a standard direct ELISA method.

Figure 3:
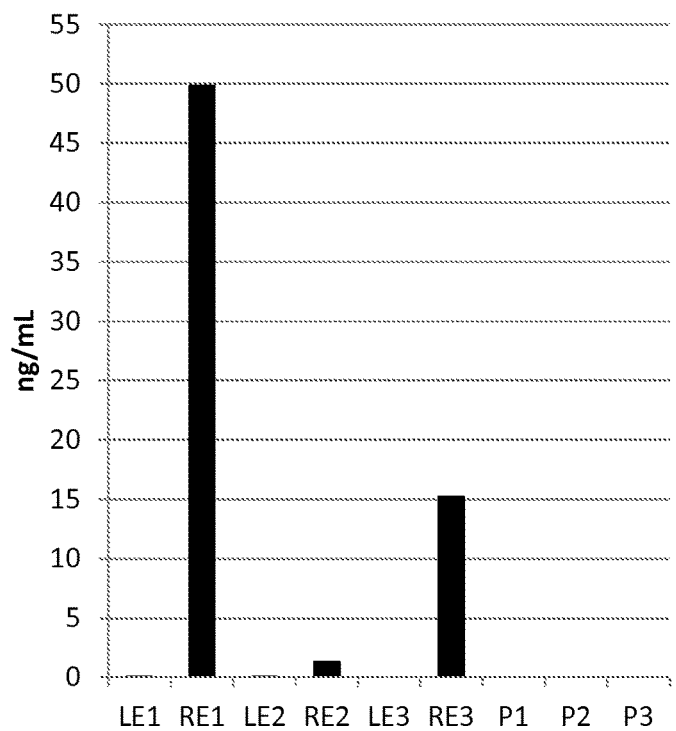
FIGS. 3A-3D show quantitation of ShK-186 and ShK-198 in the local (eye) and systemic (plasma) fluids after topical administration of ShK-186 or ShK-198 three times daily as indicated.
Figure 3:
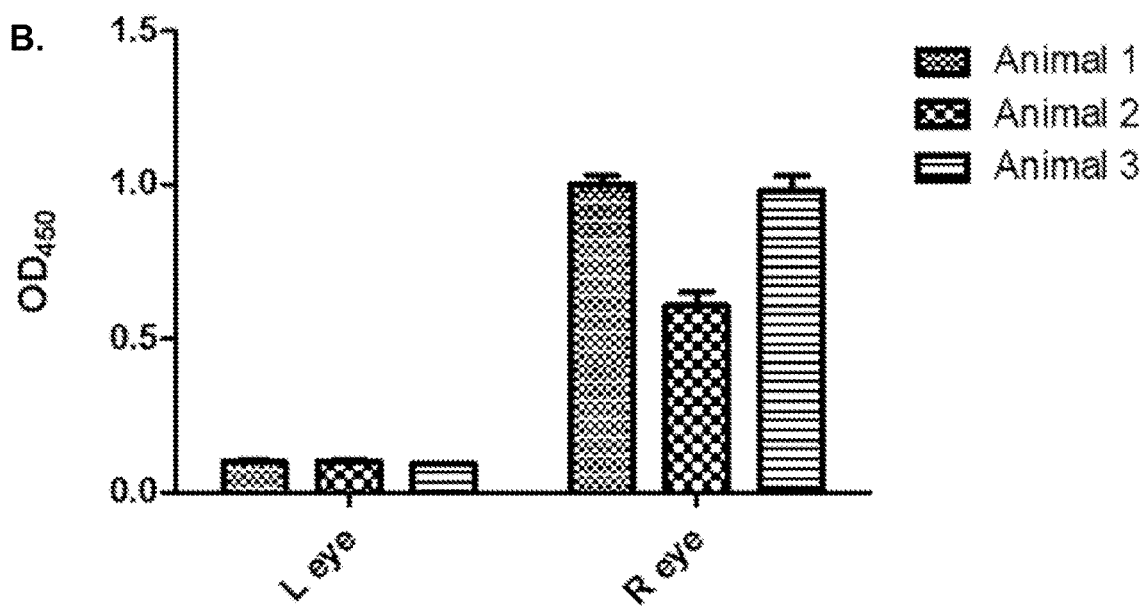
Figure 3:
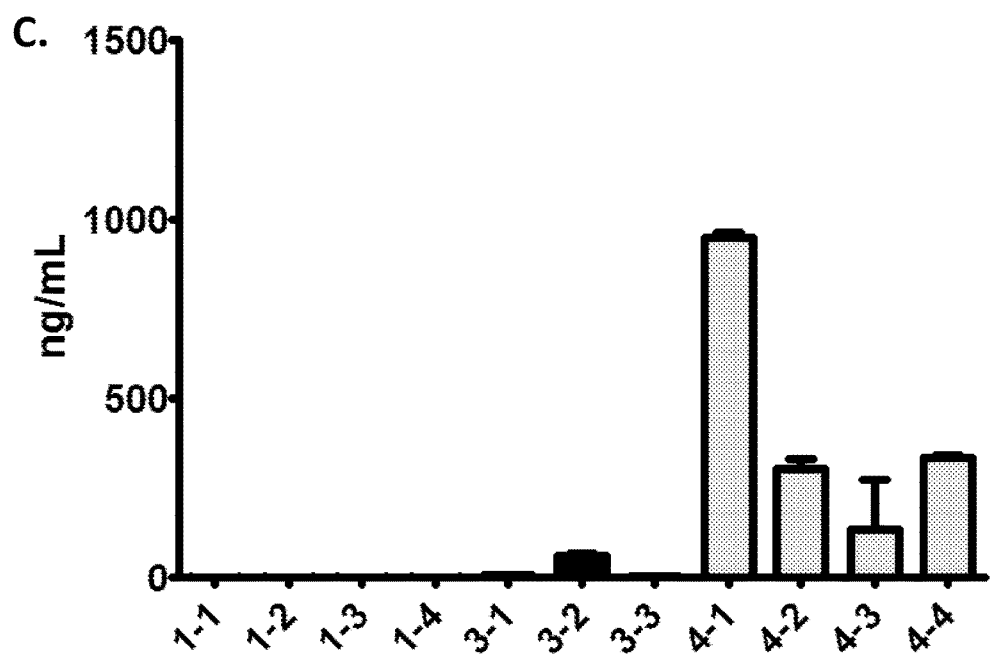
Figure 3:
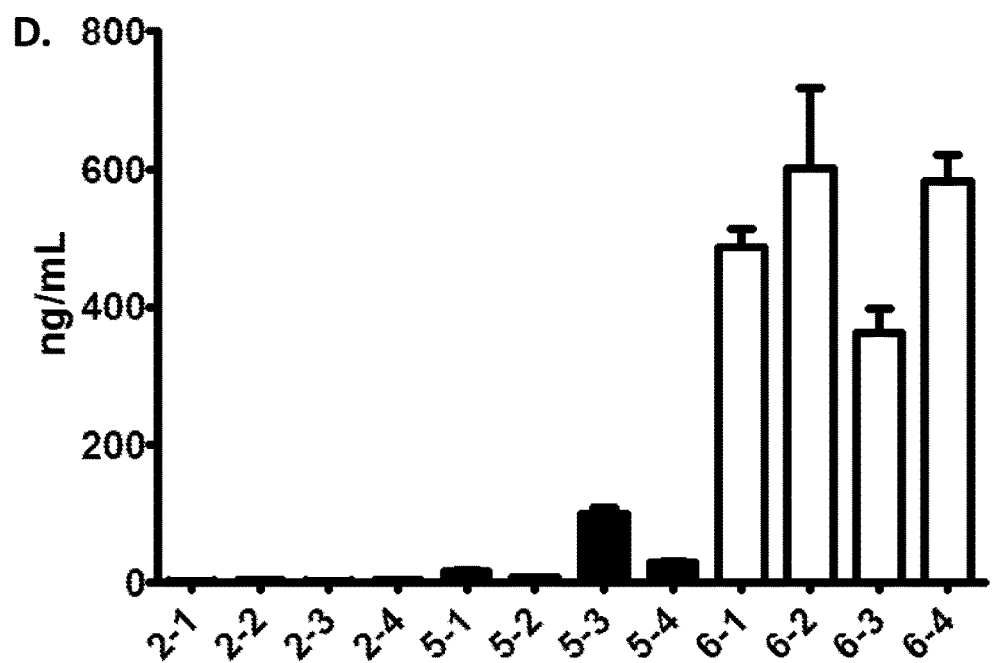

FIGS. 3A and 3B provide quantitation of ShK-186 in local aqueous fluid (FIG. 3A and FIG. 3B) and plasma (FIG. 3A) samples harvested 21 days after topical administration of ShK-186 to the right eye (RE), compared to the left eye (LE), which was dosed with vehicle. Topically administered ShK-186 was found in significant concentrations in the aqueous fluid of the RE, indicating intraocular delivery of the drug (FIGS. 3A, 3B). There was no detectable ShK-186 in samples from the untreated LE or in the plasma, indicating that there was minimal systemic exposure to the drug (FIGS. 3A & B).

Additionally, female 8-14 week LEWIS rats (Charles River) were dosed three times per day (10 μL) with topically administered saline or ShK-186 at 0.1% (animals 3-1 to 3-3) or 1% (animals 4-1 to 4-4) (FIG. 3C). ShK-198 was given at 0.1% (animals 5-1 to 5-4) or 1% as indicated in FIG. D; Animals 2-1 to 2-4 received vehicle P6N (FIG. 3D). FIG. 3C provides quantitation of ShK-186 in local aqueous fluid harvested 7 days after topical administration of ShK-186. Topically administered ShK-186 was found in significant concentrations in the anterior chamber aqueous fluid, indicating intraocular delivery of the drug. There was no detectable ShK-186 in plasma samples indicating that there was minimal systemic exposure to the drug (not shown). FIG. 3D provides quantitation of ShK-198 in anterior chamber aqueous fluid or in plasma harvested 7 days after topical administration of ShK-198. Topically administered ShK-198 was found in significant concentrations in the aqueous fluid, indicating intraocular delivery of the drug. There was no detectable ShK-198 in plasma samples, indicating that there was minimal systemic exposure to the drug (not shown).

Example 4. Evaluation of Therapeutic Effects of ShK-186 and ShK-198 in Autoimmune Eye Disease This example describes the evaluation of the therapeutic effects of localized delivery of a toxin-based therapeutic peptide of the disclosure, such as ShK-186.

One model used to evaluate the therapeutic potential of ShK-186 in autoimmune eye diseases such as uveitis was the melanin associated antigen (MAA) induced experimental autoimmune anterior uveitis (EAAU). In this model, male Lewis rats 5-10 week old (Charles River) are immunized with MAA emulsified in complete Freund's adjuvant (CFA) subcutaneously and also receive a single intraperitoneal injection of pertussis toxin (0.2 to 1 mcg/animal). Symptoms of disease begin to appear by day 10 and peak by day 18 post immunization. The animals typically recover by day 25.

Preparation of the MAA. MAA was prepared following the procedure outlined by Simpsom et al., Eye 11, 206-208, (1997) with some modifications. The iris and ciliary body structure were dissected from 25 fresh pigmented cow eyes. The tissue was cut into small pieces and then homogenized in cold PBS. The homogenate was spun at 4000 g for 10 minutes, washed three times with PBS and then put through a detergent extraction with 2% Triton X-100, rotating for 3 hours at room temperature. The resulting material was again spun and washed three times with PBS and subject to another detergent extraction this time using 2% SDS, rotating for 3 hours at 37° C. This material was washed three times with PBS followed by three washes with $H_2O$ and a final wash with 70% ethanol. The MAA pellet was placed under a vacuum for approximately 15 min, resulting in dried antigen material stored frozen at −20° C.

Figure 4:
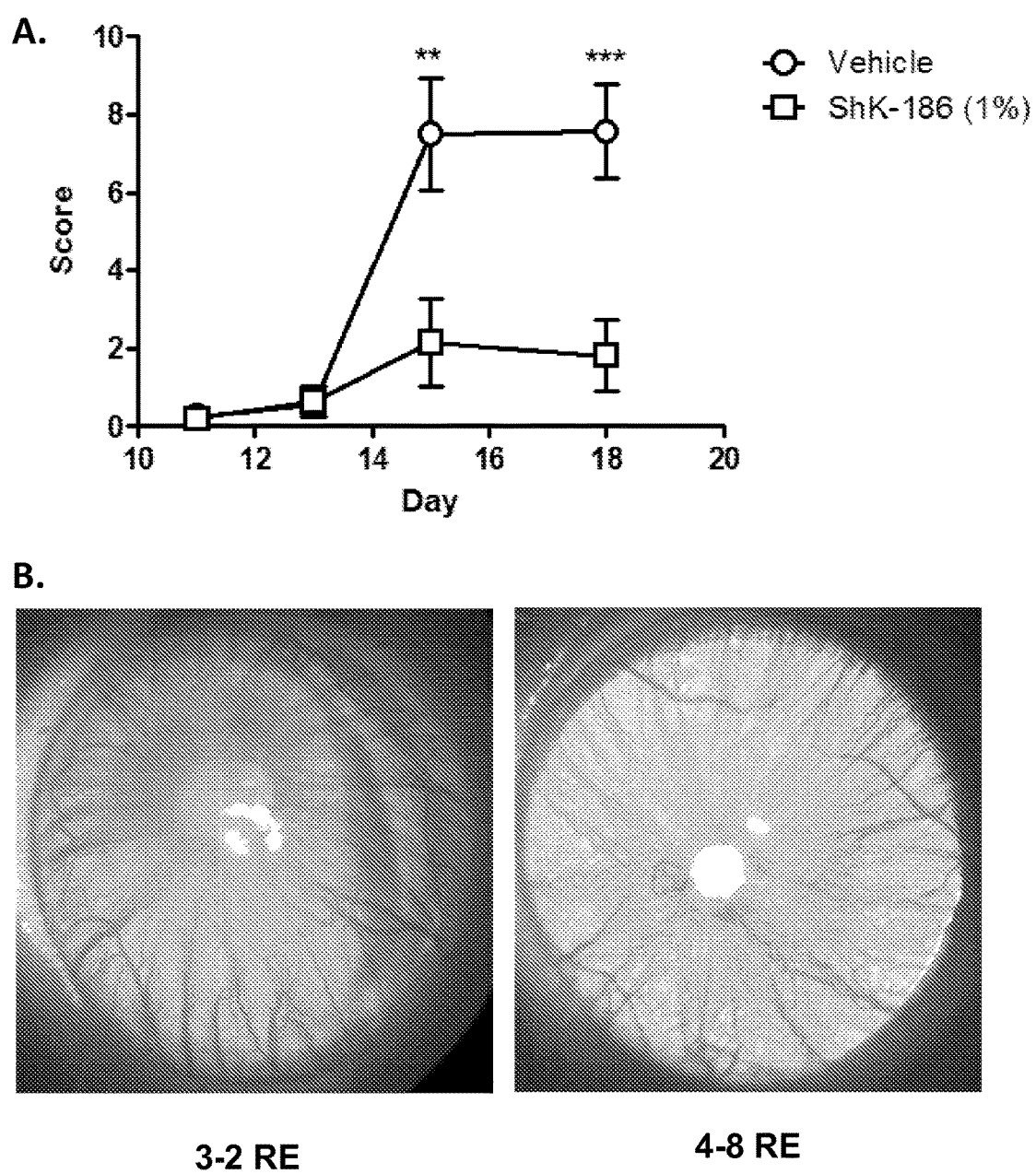
FIGS. 4A-4D show therapeutic efficacy of topical administration of ShK-186 in an experimental anterior uveitis model.
Figure 4:
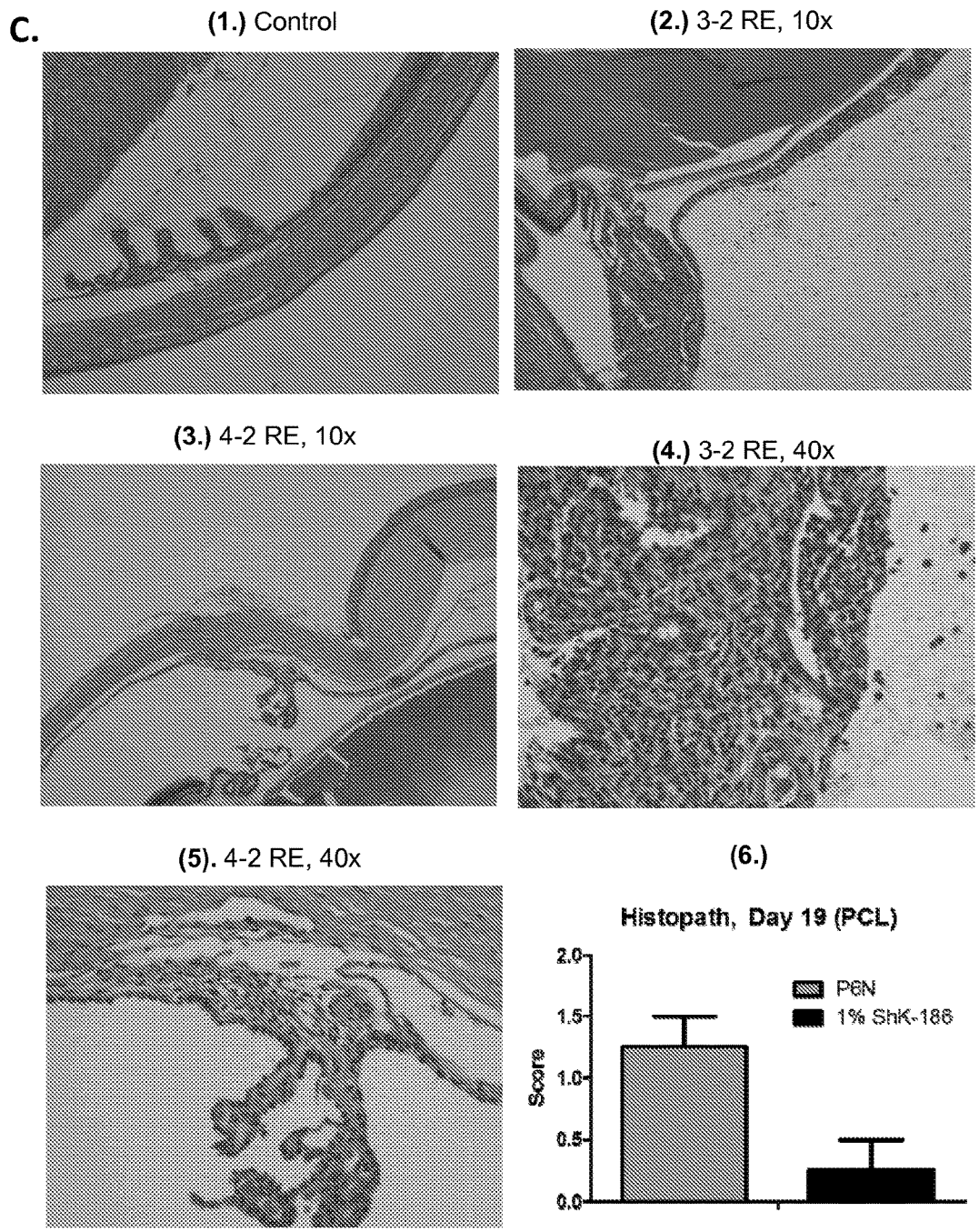
Figure 4:
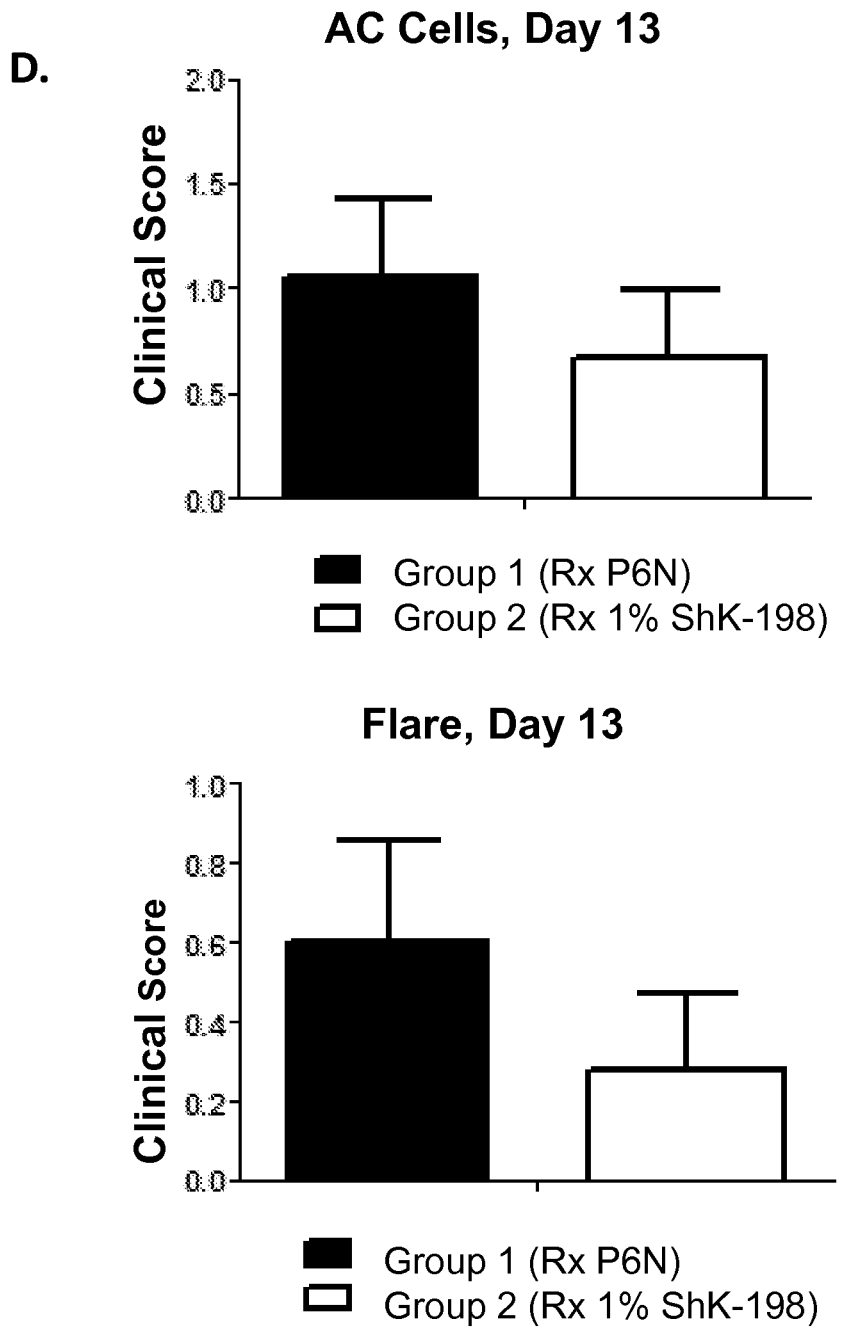

Preparation of MAA:CFA emulsions. For the emulsion used for the experiment whose results are shown in FIG. 4, 50 milligrams of MAA were resuspended in 3.8 mL of PBS, and after vortexing briefly the suspension, was sonicated for 30 seconds three times incubating on ice for 30 seconds in between. This slurry was passed through a 100 µm cell strainer, thicker material was pressed through using a syringe plunger. The protein content of the suspension was determined to be 3.27 mg/mL using a commercially available BCA kit (Pierce 23225), and was stored frozen at −20° C. until use. On the day of immunization (day 0), the stock MAA was thawed at room temperature and vortexed briefly before a working dilution of 600 µg/mL was made. This solution was then mixed drop wise 1:1 with CFA while vortexing, for a final antigen concentration of 300 µg/mL (or 30 µg per animal). Emulsions were allowed to vortex an additional 5 minutes before being loaded into syringes and passed through an 18 G emulsifying bridge until very thick. Emulsions were injected the same day, 50 µL subcutaneous to each footpad, 100 µL total per animal, according to group. FIGS. 4A-D show the pathology associated with this disease model and the effects of ShK-186 topical administration on the occurrence and severity of disease.

FIG. 4A shows data on the clinical observations made of each animal using a slit lamp on days 11, 13, 15, and 18 post induction of EAAU. Eyes were given individual scores based on pupil function (miosis), iris structure, presence of cells in the anterior chamber, and presence of protein in the anterior chamber (flare). Scores were then converted into a composite clinical score for each day. Composite scores of animals treated three times daily with 0.1% from day 0-8 and with 1% ShK-186 from day 9-18 topically to the eye were found to be significantly lower than those treated with vehicle.

As can be seen in FIG. 4B, ShK-186 topical administration reduced gross pathology in this model. (Left panel (3-2 RE)) Animal was dosed three times daily with vehicle (P6N). On day 18 post immunization, animal 3-2 is observed to have a composite clinical score of 13: a miotic pupil completely full of protein (score=4), engorged iris blood vessels with some damage (score=3), many infiltrating cells in the anterior chamber (score=4; not pictured), and slight flare (score=2; not pictured). The animal depicted in (Right panel, 4-8 RE) received topical administration of 0.1% ShK-186 for 9 days and 1% ShK-186 for an additional 10 days, post immunization for induction of EAAU. On day 18 post immunization, animal 4-8 is observed to have a composite clinical score of 0: normal pupil (score=0), normal iris vessels and structure (score=0), no visible cells or protein in the anterior chamber (score=0 for each; not pictured).

As expected from the gross pathology observations, ShK-186 topical administration also reduced histopathology as shown in FIG. 4C. For this analysis, sections of eyes previously fixed in 10% formalin were scored for iris and ciliary body structure and the degree of inflammatory cell infiltration to the stroma of the iris and/or ciliary body and anterior chamber according to disease parameters outlined by Kim et al., supra (1997); this was done by an independent veterinary pathologist. In FIG. 4C (1.) a control healthy eye (10×) is shown; (2.) & (4.) show the eye from an animal treated with vehicle that was scored a 2 (10×, 40×); (3.) & (5.) show the eye from an animal treated three times daily with 0.1% ShK-186 for 8 days followed by 1% ShK-186 for 10 days which was given a histopathology score of 0 (10×, 40×). FIG. 4C (6.) shows the composite clinical score based on histopathology analysis of four eyes from a vehicle treated group (P6N) or ShK-186-treated group as indicated (1% ShK-186).

FIG. 4D shows data demonstrating that ShK-198 topical administration reduces clinical symptoms in a rat model of EAAU. Clinical observations were made of each animal using a slit lamp on day 13 post induction of EAAU by immunization with an adjuvanted MAA emulsion. Clinical observations were made of each animal using a slit lamp on day 13 post induction of EAAU by immunization with an adjuvanted MAA emulsion. Eyes were given individual scores based on presence of cells in the anterior chamber (Top Panel), or the presence of protein in the anterior chamber or flare (Bottom Panel). Rats were treated three times daily with P6N vehicle or 1% ShK-198 topically to the eye. N=10 rats/20 eyes.

Other models used to evaluate the preventive and therapeutic potential of ShK-186, ShK-198, or related peptides on uveitis disease include those induced by retinal antigens. These experimental autoimmune uveitis or uveoretinitis models (EAU) are also organ-specific T-cell mediated disorders in which effector memory CD4+ and CD8+ T-cells, typically Th1 (IFN-γ producing), Th17 (IL-17 producing), or Th1/Th17 (IFN-γ/IL-17) co-producing cells are thought to play a key pathogenic role. In these models, either bovine, rodent, or human retinal soluble antigen (S—Ag, also known as arrestin) from a photoreceptor protein, or antigens from the interphotoreceptor retinoid-binding protein, including R14 and R16 peptides from this protein, which is found in the interphotoreceptor matrix involved in Vitamin A derivatives transport, are emulsified in CFA. Emulsions are used to immunize susceptible strains of mice (B10.RIII; C57.BL/6), rats (Lewis, F344, CAR, BN, PVG), or guinea pigs with or without the addition of purified pertussis toxin, given concurrently. Other sources of antigen that can be used include rhodopsin, recoverin, and phosducin. (Reviewed in Agarwal et al., (2012); Andras Perl (ed.), Autoimmunity: Methods and Protocols, Methods in Molecular Biology, vol. 900. Springer Science+Business Media New York).

Example 5. Evaluation of Therapeutic Effects of ShK-186 and ShK Analogs in Dry Eye Disease Models Evaluation of the prophylactic and therapeutic effects of ShK-186 and other peptides of the disclosure can be conducted by analyzing keratoconjunctivitis sicca (KCS). KCS can be induced bilaterally in animals after removal of orbital and nictitans lacrimal glands (Moore et al., Invest Ophthalmol Vis Sci., 42(3), 653-659 (2001)). Lacrimal gland removal results in induction of disease in animals including rats, rabbits, and dogs about 2-3 weeks post-surgery as determined by a significant reduction in Schirmer tear test (STT) values. Intracellular mucin stores are also quantified and are reduced in conjunctival samples from diseased animals. After induction of KCS, ShK-186, ShK-198, or any of the toxin-based or ShK-based peptides listed in Tables 1 and 2 respectively can be applied in concentrations ranging from 0.05 to 5% in P6N or in another vehicle, once, twice, thrice, or more times/day. Incisional biopsy specimens of ventral fornix conjunctiva can be collected before gland removal (baseline) and at 2, 4, and 6 weeks after induction. At each sampling time, eyes are photographed and color graded subsequently for degree of conjunctivitis and characteristics of ocular discharge.

Evaluation of the prophylactic and therapeutic effects of ShK-186 and other peptides of the disclosure can be conducted in an Experimental Autoimmune Dry Eye Disease model of Sjogren's syndrome. One such model is described in the teachings of Jiang et al., Invest. Ophthalmol. Vis. Sci., 50, 2245-2254 (2009). In this model, Lewis rats are immunized subcutaneously with 0.2 mL of an emulsion containing 500 µg of lacrimal and salivary gland extract or 200 µg of recombinant mouse Klk1b22 and 500 µg of *Mycobacterium tuberculosis* H37Ra (Difco, Detroit, Mich.) in incomplete Freund's adjuvant (Sigma, St. Louis, Mo.), distributed over 4 spots on the tail base and flank. A single dose of 200, 500, 750, or 1000 nanograms of pertussis toxin is injected intraperitoneally on the same day as the antigen emulsion.

Another model used to evaluate ShK-186 efficacy is the antigen-specific T-cell adoptive transfer model. In this model, purified T-cells are prepared from the draining lymph nodes or spleen of previously immunized rats. These cells are then mixed with lacrimal gland extracts (or fraction VII purified from the extract; or Klk1b22) and cultured together. After 2, 3, 4, 5, or 7 days, the T-cells are injected intraperitoneally in 0.5 mL of PBS into naïve Lewis recipients (5 million cells/rat).

Other models of experimental dry eye disease include topical administration of preservative benzlkonium chloride (Xiong et al., Invest Ophthalmol Vis Sci, 49, 1850-1856 (2008)).

In the above described models, toxin-based therapeutic peptides such as ShK-186 or vehicle treatment can be started at different times prior or after immunization or T-cell transfer in order to assess either prophylactic or therapeutic effects of the peptides.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., Molecular Cloning (Cold Spring Harbor Laboratory Press, Cold Spring Harbor, N.Y., 1982); Sambrook et al., Molecular Cloning, 2nd Ed. (Cold Spring Harbor Laboratory Press, Cold Spring Harbor, N.Y., 1989); Sambrook and Russell, Molecular Cloning, 3rd Ed. (Cold Spring Harbor Laboratory Press, Cold Spring Harbor, N.Y., 2001); Ausubel et al., Current Protocols in Molecular Biology (John Wiley & Sons, updated through 2005); Glover, DNA Cloning (IRL Press, Oxford, 1985); Anand, Techniques for the Analysis of Complex Genomes, (Academic Press, New York, 1992); Guthrie and Fink, Guide to Yeast Genetics and Molecular Biology (Academic Press, New York, 1991); Harlow and Lane, Antibodies, (Cold Spring Harbor Laboratory Press, Cold Spring Harbor, N.Y., 1998); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, (Blackwell Scientific Publications, Oxford, 1988); Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), 4th Ed., (Univ. of Oregon Press, Eugene, Oreg., 2000).

As will be understood by one of ordinary skill in the art, each embodiment disclosed herein can comprise, consist essentially of, or consist of its particular stated element, step, ingredient, or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. As used herein, a material effect would cause a statistically significant reduction in the ability of a toxin-based therapeutic peptide disclosed herein to treat an inflammatory ophthalmic condition.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents, and/or patent applications (collectively "references") throughout this specification. Each of the cited references is individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

---

What is claimed is:

1. A method of treating an inflammatory ophthalmic condition comprising administering to a subject a therapeutically effective amount of a pharmaceutical composition comprising a peptide and a pharmaceutically acceptable carrier, wherein the peptide has a sequence that is at least 95% identical to (a) any one of SEQ ID NOs: 2-207, 211-216, and 224, wherein said peptide is attached by an aminoethyloxyethyloxy-acetyl linker (AEEAc) to an organic or inorganic chemical entity that has an anionic charge, or (b) any one of SEQ ID NO:208-210, 217-220, 222, and 223, wherein the inflammatory ophthalmic condition is keratoconjunctivitis sicca (dry eye), uveitis, episcleritis, keratitis, retinal vasculitis, scleritis, endophthalmitis, cicatricial pemphigoid, Mooren's ulcer, cytomegalovirus-mediated retinitis and/or pediatric uveitis, or wherein the inflammatory ophthalmic condition is caused by systemic lupus erythematosus, microscopic polyangitis, polyarteritis nodosa, Wegener's granulomatosis (granulomatosis with polyangitis), sarcoidosis, Behcet's syndrome, Vogt-Koyanagi-Harada disease, Takayasu's arteritis, rheumatoid arthritis, relapsing polychondritis, ankulosing spondylitis, and/or Churg-Strauss syndrome, and wherein said subject is a human with said inflammatory ophthalmic condition.

2. The method according to claim 1, wherein said organic or inorganic chemical entity is L-Pmp(OH$_2$) (p-phosphonomethyl-phenylalanine), D-Pmp(OH$_2$), D-Pmp(OHEt), Pmp(Et$_2$), D-Pmp(Et$_2$), L-Tyr, L-Tyr(PO$_3$H$_2$), L-Phe(p-NH$_2$), Phe(p-CO$_2$H), L-Aspartate, D-Aspartate, L-Glutamate, D-Glutamate, Ppa p-phosphatidyl-phenylalanine), Pfp (p-Phosphono(difluoro-methyl)-Phenylalanine) or Pkp (p-Phosphono-methylketo-Phenylalanine).

3. The method according to claim 1, wherein said peptide has the sequence of SEQ ID NO:210.

4. The method according to claim 1, wherein said peptide has the sequence of SEQ ID NO:217.

5. The method according to claim 2, wherein the C-terminus of the peptide is an acid or an amide.

6. The method according to claim 1, wherein the pharmaceutically effective carrier comprises one or more of a preservative, a viscosity enhancer, an antioxidant, a buffering agent, a tonicity modifier, and/or a surfactant.

7. The method according to claim 6, wherein the buffering agent is a citrate buffer, a succinate buffer, a tartrate buffer, a fumarate buffer, a gluconate buffer, an oxalate buffer, a lactate buffer, an acetate buffer, a phosphate buffer, a histidine buffer, or a trimethylamine salt; the preservative is a phenol, an octadecyldimethylbenzyl ammonium chloride, a benzalkonium halide, hexmethonium chloride, an alkyl paraben, a catechol, a resorcinol, a cyclohexanol, 3-pentanol, bebzalkonium chloride, ascorbic acid, benzethonium chloride, chlorobutanol, phenylmercuric acetate, phenylmercuric nitrate, thimerosal, methylparaben, and/or a propylparabens; the viscosity enhancer is carboxymethylcellulose, hydroxymethylcellulose, hydroxypropylmethylcellulose, methylcellulose, polyvinyl alcohol, polycarbophil, gellan gum, xanthan gum, carbopol, poly(styrene-divinyl benzene)sulfonic acid, and/or polyvinylpyrrolidine; the antioxidant is alpha-tocopherol, ascorbic acid, ascorbyl palmitate, butylated hydroxyanisole, butylated hydroxytoluene, citric acid, cysteine hydrochloride, ethylenediamine tetraacetic acid (EDTA), lecithin, metal chelating agents, methionine, phosphoric acid, propyl gallate, sodium bisulfite, sodium metabisulfite, sodium sulfite, sorbitol, tartaric acid, vitamin E, and/or thiaurea; and the solubilizer is poly(ethyleneglycol-block-poly(propylene glycol)-block-poly(ethylene glycol) (Poloxamer-407), a polyoxyethylene-polyoxypropylene block copolymer, a polysorbate, polyethylene-35-castor oil, hydroxypropyl-beta-cyclodextrin, methyl-beta-cyclodextrin, n-octenyl succinate starch, tyloxapol, alpha-tocopherol, polyethylene glycol succinate, a medium triglyceride, sesame oil, *arachis* oil, safflower oil, mustard oil, soybean oil, sunflower oil, a phospholipid, oil-in-water emulsions, and/or a surfactant.

8. The method according to claim 1, wherein the administering is topically to the eye, parenteral and/or enteral, or the administering is by intravitreal injection.

9. The method according to claim 1, wherein the administering is six times daily, five times daily, four times daily, three times daily, twice daily, daily, weekly, monthly, every two months, every three months, or every six months.

10. The method according to claim 1, wherein the subject is a human child, adolescent, or adult.

11. The method according to claim 6, wherein the pharmaceutical composition comprises 10 mM sodium phosphate, 0.8% w/v NaCl; and polysorbate 20 or polysorbate 80 at 0.01, 0.05, 0.1, 0.2, 0.4, 0.6, or 0.8 w/v %, wherein the composition has a pH of 5.0, 5.5, 6.0, 6.5, 7, 7.5, or 8.

12. The method according to claim 11, wherein the pharmaceutical composition comprises polysorbate 20 at 0.05 w/v %, and wherein the composition has a pH of 6.0, or wherein the pharmaceutical composition comprises polysorbate 80 at 0.05 w/v %, and wherein the composition has a pH of 6.0.

* * * * *